US009850290B2

(12) United States Patent
Deisseroth et al.

(10) Patent No.: US 9,850,290 B2
(45) Date of Patent: *Dec. 26, 2017

(54) LIGHT-ACTIVATED CHIMERIC OPSINS AND METHODS OF USING THE SAME

(71) Applicant: The Board of Trustees of the Leland Stanford Junior University, Stanford, CA (US)

(72) Inventors: Karl Deisseroth, Stanford, CA (US); Ofer Yizhar, Palo Alto, CA (US); Lief Fenno, San Francisco, CA (US); Peter Hegemann, Falkensee (DE); Matthias Prigge, Berlin (DE)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/147,772

(22) Filed: May 5, 2016

(65) Prior Publication Data

US 2016/0237126 A1 Aug. 18, 2016

Related U.S. Application Data

(60) Continuation of application No. 14/862,926, filed on Sep. 23, 2015, now Pat. No. 9,340,589, which is a division of application No. 13/875,966, filed on May 2, 2013, now Pat. No. 9,175,095, which is a continuation of application No. PCT/US2011/059276, filed on Nov. 4, 2011.

(60) Provisional application No. 61/511,912, filed on Jul. 26, 2011, provisional application No. 61/410,736, filed on Nov. 5, 2010, provisional application No. 61/410,744, filed on Nov. 5, 2010.

(51) Int. Cl.
| | |
|---|---|
| *C07K 14/705* | (2006.01) |
| *C07K 19/00* | (2006.01) |
| *G01N 3/50* | (2006.01) |
| *C07K 14/405* | (2006.01) |
| *G01N 33/50* | (2006.01) |
| *C12N 13/00* | (2006.01) |
| *A61N 5/06* | (2006.01) |
| *A01K 67/027* | (2006.01) |
| *A61K 38/00* | (2006.01) |

(52) U.S. Cl.
CPC ........ *C07K 14/405* (2013.01); *A01K 67/0275* (2013.01); *A61N 5/06* (2013.01); *C07K 19/00* (2013.01); *C12N 13/00* (2013.01); *G01N 33/5058* (2013.01); *A01K 2217/052* (2013.01); *A01K 2227/105* (2013.01); *A01K 2267/0393* (2013.01); *A61K 38/00* (2013.01); *A61N 2005/0663* (2013.01); *C07K 2319/00* (2013.01); *C07K 2319/60* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 2,968,302 | A | 1/1961 | Fry et al. |
| 3,131,690 | A | 5/1964 | Innis et al. |
| 3,499,437 | A | 3/1970 | Balamuth et al. |
| 3,567,847 | A | 3/1971 | Price |
| 4,343,301 | A | 8/1982 | Indech |
| 4,559,951 | A | 12/1985 | Dahl et al. |
| 4,616,231 | A | 10/1986 | Autrey et al. |
| 4,865,042 | A | 9/1989 | Umemura et al. |
| 4,879,284 | A | 11/1989 | Lang et al. |
| 5,032,123 | A | 7/1991 | Katz et al. |
| 5,041,224 | A | 8/1991 | Ohyama et al. |
| 5,082,670 | A | 1/1992 | Gage et al. |
| 5,249,575 | A | 10/1993 | Di Mino et al. |
| 5,267,152 | A | 11/1993 | Yang et al. |
| 5,290,280 | A | 3/1994 | Daikuzono et al. |
| 5,330,515 | A | 7/1994 | Rutecki et al. |
| 5,382,516 | A | 1/1995 | Bush |
| 5,411,540 | A | 5/1995 | Edell et al. |
| 5,445,608 | A | 8/1995 | Chen et al. |
| 5,460,950 | A | 10/1995 | Barr et al. |
| 5,460,954 | A | 10/1995 | Lee et al. |
| 5,470,307 | A | 11/1995 | Lindall |
| 5,495,541 | A | 2/1996 | Murray et al. |
| 5,520,188 | A | 5/1996 | Hennige et al. |
| 5,527,695 | A | 6/1996 | Hodges et al. |
| 5,550,316 | A | 8/1996 | Mintz |
| 5,641,650 | A | 6/1997 | Turner et al. |
| 5,703,985 | A | 12/1997 | Owyang et al. |

(Continued)

FOREIGN PATENT DOCUMENTS

| | | |
|---|---|---|
| CN | 1079464 A | 12/1993 |
| CN | 102076866 A | 5/2011 |

(Continued)

OTHER PUBLICATIONS

Chinta, et al.; "Dopaminergic neurons"; The International Journal of Biochemistry & Cell Biology; vol. 37, pp. 942-946 (2005).

Grady, et al.; "Age-Related Reductions in Human Recognition Memory Due to Impaired Encoding"; Science; vol. 269, No. 5221, pp. 218-221 (Jul. 14, 1995).

Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].

(Continued)

*Primary Examiner* — John Ulm
(74) *Attorney, Agent, or Firm* — Bozicevic, Field & Francis LLP; Paula A. Borden

(57) ABSTRACT

Provided herein are compositions comprising light-activated chimeric proteins expressed on plasma membranes and methods of using the same to selectively depolarize excitatory or inhibitory neurons.

21 Claims, 36 Drawing Sheets

(56) References Cited

U.S. PATENT DOCUMENTS

| | | |
|---|---|---|
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Schneider et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,284,353 B2 | 3/2016 | Deisseroth et al. |
| 9,359,449 B2 | 6/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarakis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0267118 A1 | 12/2004 | Dawson |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |

(56) References Cited

U.S. PATENT DOCUMENTS

| | | |
|---|---|---|
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0234273 A1 | 9/2010 | Deisseroth et al. |
| 2011/0021970 A1 | 1/2011 | Vo-Dinh et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0253261 A1 | 10/2012 | Poletto et al. |
| 2013/0030275 A1 | 1/2013 | Seymour et al. |
| 2013/0089503 A1 | 4/2013 | Deisseroth et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0072394 A1 | 3/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2015/0297719 A1 | 10/2015 | Deisseroth et al. |
| 2016/0002302 A1 | 1/2016 | Deisseroth et al. |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |
| 2016/0096036 A1 | 4/2016 | Deisseroth et al. |

FOREIGN PATENT DOCUMENTS

| | | |
|---|---|---|
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2007530027 A | 11/2007 |
| JP | 2008010422 A | 1/2008 |
| JP | 2010227537 A | 10/2010 |
| JP | 2012508581 | 4/2012 |
| WO | WO 95/05214 | 2/1995 |
| WO | WO 96/32076 | 10/1996 |
| WO | WO 00/27293 | 5/2000 |
| WO | WO 01/25466 | 4/2001 |
| WO | WO 03/016486 | 2/2003 |

(56) References Cited

FOREIGN PATENT DOCUMENTS

| WO | WO 03/040323 | 5/2003 |
|---|---|---|
| WO | WO 03/046141 | 6/2003 |
| WO | WO 03/084994 | 10/2003 |
| WO | WO 03/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Jones, et al.; "Animal Models of Schizophrenia"; British Journal of Pharmacology; vol. 164, pp. 1162-1194 (2011).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Co-pending U.S. Appl. No. 14/886,763, filed Oct. 19, 2015.
Co-pending U.S. Appl. No. 14/911,405, filed Feb. 26, 2016.
Co-pending U.S. Appl. No. 15/008,214, filed Jan. 27, 2016.
Co-pending U.S. Appl. No. 15/059,159, filed Mar. 2, 2016.
Co-pending U.S. Appl. No. 15/095,519, filed Apr. 11, 2016.
Co-pending U.S. Appl. No. 15/097,925, filed Apr. 13, 2016.
Co-pending U.S. Appl. No. 15/063,296, filed Mar. 7, 2016.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila rhodopsin* cytoplasmic tail domain is required for maintenance of rhabdomere structure." The FASEB Journal, 2007, vol. 21, p. 449-455.
Airan, et al.; "Integration of light-controlled neuronal firing and fast circuit imaging"; Current Opinion in Neurobiology; vol. 17, pp. 587-592 (2007).
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.

(56) References Cited

OTHER PUBLICATIONS

Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.

(56) References Cited

OTHER PUBLICATIONS

Date, et al. "Grafting of Encapsulated Dopamine-Secreting Cells in Parkinson's Disease: Long-Term Primate Study", Cell Transplant, 2000, vol. 9, pp. 705-709.
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Deonarain; "Ligand-targeted receptor-mediated vectors for gene delivery"; Exp. Opin. Ther. Patents; vol. 8, No. 1, pp. 53-69 (1998).
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: BOR5N9; "Subname: Full= Bacteriorhodopsin"; (Apr. 8, 2008).
EBI accession No. UNIPROT: B4YI03; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).

Edelstein, et al.; "Gene therapy clinical trials worldwide 1989-2004—an overview"; The Journal of Gene Medicine; vol. 6, pp. 597-602 (2004).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain" , Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine D2 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.

(56) References Cited

OTHER PUBLICATIONS

Glick et al. "Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation-a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431-439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage TBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.

Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.

(56) References Cited

OTHER PUBLICATIONS

Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnson-Saliba, et al.; "Gene Therapy: Optimising DNA Delivery to the Nucleus"; Current Drug Targets; vol. 2, pp. 371-399 (2001).
Johnston et al. "Isolation of the yeast regulatory gene GAL4 and analysis of its dosage effects on the galactose/melibiose regulon," PNAS, 1982, vol. 79, pp. 6971-6975.
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-10.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lord., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. at at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif', J. Bioi. Chem. (2000), 275(16)11597-11602.
Lim et al., "A Novel Targeting Signal for Proximal Clustering of the Kv2.1K+ Channel in Hippocampal Neurons", Neuron, 2000, vol. 25: pp. 385-397.

(56) References Cited

OTHER PUBLICATIONS

Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases" , Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

(56) References Cited

OTHER PUBLICATIONS

Palmer et al., "The Adult Rat Hippocampus Contains Primordial Neural Stem Cells", Molecular and Cellular Neuroscience, 1997, vol. 8, pp. 389-404.
Palu, et al.; "In pursuit of new developments for gene therapy of human diseases"; Journal of Biotechnology; vol. 68, pp. 1-13 (1999).
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1.I-9.1 1 .I 8.
Peralvarez-Marin et al., "Inter-helical hydrogen bonds are essential elements for intra-protein signal transduction: the role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pfeifer, et al.; "Gene Therapy: Promises and Problems"; Annu. Rev. Genomics Hum. Genet.; vol. 2, pp. 177-211 (2001).
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Powell, et al.; "Schizophrenia-Relevant Behavioral Testing in Rodent Models: A Uniquely Human Disorder?"; Biol. Psychiatry; vol. 59, pp. 1198-1207 (2006).
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.

Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl− cotransporter KCC2 and Impairs Neuronal Cl− Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Schroll et al., "Light-induced activation of distinct modulatory neurons triggers appetitive or aversive learning in *Drosophila* larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.

(56) References Cited

OTHER PUBLICATIONS

Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Shoji, et al.; "Current Status of Delivery Systems to Improve Target Efficacy of Oligonucleotides"; Current Pharmaceutical Design; vol. 10, pp. 785-796 (2004).
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al. "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al. "Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biot Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al., "Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (MINI) Probe System," Proceedings of the 2005 IEEE,

(56) References Cited

OTHER PUBLICATIONS

Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.I-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42)13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No. 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl. Med., 2013, 5(177):177.
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330: 17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.

Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Definition of integral. Merriam-Webster Dictionary, retrieved on Mar. 20 2017; Retrieved from the internet: <http://www.merriam-webster.com/dictionary/integral>, 1 page.
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012), pp. 1-9.
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).

(56) References Cited

OTHER PUBLICATIONS

Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages. (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages. (2010).

```
ChR1    MSRRPWLLAL ALAVALAAGS AGASTGSDAT VPVATQDGPD YVFHRAHERM  60
ChR2    .......... .....MDYGG ALSAVG.... .......... .......REL  14
VChR1   .......... .......... .......... .......... ..MDYPVARS   8

ChR1    LFQTSYTLEN NGSVICIPNN GQCFCLAWLK SNGTNAEKLA ANILQWITFA 100
ChR2    LFVTNPVVVN .GSVLVP..E DQCYCAGWIE SRGTNGAQTA SNVLQWLAAG  61
VChR1   LIVRYPTDLG NGTVCMP..R GQCYCEGWLR SRGTSIEKTI AITLQWVVFA  56
                                                   [    TM1    ]

ChR1    LSALCLMFYG YQTWKSTCGW EEIYVATIEM IKFIIEYFHE FDEPAVIYSS 150
ChR2    FSILLLMFYA YQTWKSTCGW EEIYVCAIEM VKVILEFFFE FKNPSMLYLA 111
VChR1   LSVACLGWYA YQAWRATCGW EEVYVALIEM MKSIIEAFHE FDSPATLWLS 106
        [              ] [        TM2         ]         └Splice 1

Splice 2┐
ChR1    NGNKTVWLRY AEWLLTCRVI LIHLSNLTGL ANDYNKRTMG LLVSDIGTIV 200
ChR2    TGHRVQWLRY AEWLLTCPVI LIHLSNLTGL SNDYSRRTMG LLVSDIGTIV 161
VChR1   SGNGVVWMRY GEWLLTCPVL LIHLSNLTGL KDDYSKRTMG LLVSDVGCIV 156
              [        TM3        ]       [       TM4       ]

ChR1    WGTTAALSKG YVRVIFFLMG LCYGIYTFFN AAKVYIEAYH TVPKGICRDL 250
ChR2    WGATSAMATG YVKVIFFCLG LCYGANTFFH AAKAYIEGYH TVPKGRCRQV 211
VChR1   WGATSAMCTG WTKILFFLIS LSYGMYTYFH AAKVYIEAFH TVPKGICREL 206
        [   ][        TM5        ]                    [

ChR1    VRYLAWLYFC SWAMFPVLFL LGPEGFGHIN QFNSAIAHAI LDLASKNAWS 300
ChR2    VTGMAWLFFV SWGMFPILFI LGPEGFGVLS VYGSTVGHTI IDLMSKNCWG 261
VChR1   VRVMAWTFFV AWGMFPVLFL LGTEGFGHIS PYGSAIGHSI LDLIAKNMWG 256
             [     TM6     ]            [       TM7        ]

ChR1    MMGHFLRVKI HEHILLYGDI RKKQKVNVAG QEMEVETMVH EEDD       344
ChR2    LLGHYLRVLI HEHILIHGDI RKTTKLNIGG TEIEVETLVE DEAEAGAVP  310
VChR1   VLGNYLRVKI HEHILLYGDI RKKQKITIAG QEMEVETLVA EEED       300
        [         ]
```

FIG. 3

LIGHT-ACTIVATED CHIMERIC OPSINS AND METHODS OF USING THE SAME

CROSS-REFERENCE TO RELATED APPLICATIONS

This application is a continuation of U.S. patent application Ser. No. 14/862,926, filed Sep. 23, 2015, now U.S. Pat. No. 9,340,589, which is a divisional of U.S. patent application Ser. No. 13/875,966, filed May 2, 2013, now U.S. Pat. No. 9,175,095, which is a continuation of International Patent Application No. PCT/US2011/059276, filed Nov. 4, 2011, which claims benefit to U.S. Provisional Patent Application Nos. 61/511,912, filed on Jul. 26, 2011; 61/410,736, filed on Nov. 5, 2010; and 61/410,744, filed on Nov. 5, 2010, the disclosures of each of which are incorporated herein by reference in their entireties.

TECHNICAL FIELD

This application pertains to compositions comprising animal cells expressing light-activated chimeric proteins on their plasma membranes and methods of using the same to selectively depolarize excitatory or inhibitory neurons residing in the same microcircuit in the pre-frontal cortex.

BACKGROUND

The neurophysiological substrates of most psychiatric disorders are poorly understood, despite rapidly emerging information on genetic factors that are associated with complex behavioral phenotypes such as those observed in autism and schizophrenia (Cichon et al., *The American Journal of Psychiatry* 166(5):540 (2009); O'Donovan et al., *Human Genetics* 126(1): 3 (2009)). One remarkable emerging principle is that a very broad range of seemingly unrelated genetic abnormalities can give rise to the same class of psychiatric phenotype (such as social behavior dysfunction; Folstein & Rosen-Sheidley, *Nature Reviews* 2(12):943 (2001)). This surprising pattern has pointed to the need to identify simplifying circuit-level insights that could unify diverse genetic factors under a common pathophysiological principle.

One such circuit-level hypothesis is that elevation in the ratio of cortical cellular excitation and inhibition (cellular E/I balance) could give rise to the social and cognitive deficits of autism (Rubenstein, *Current Opinion in Neurology* 23 (2):118; Rubenstein & Merzenich, *Genes, Brain, and Behavior* 2(5):255 (2003)). This hypothesis could potentially unify diverse streams of pathophysiological evidence, including the observation that many autism-related genes are linked to gain-of-function phenotypes in ion channels and synaptic proteins (Bourgeron, *Current Opinion in Neurobiology* 19 (2), 231 (2009)) and that ~30% of autistic patients also show clinically apparent seizures (Gillberg & Billstedt, *Acta Psychiatrica Scandinavica*, 102(5):321 (2000)). However, it has not been clear if such an imbalance (to be relevant to disease symptoms) would be operative on the chronic (e.g. during development) or the acute timescale. Furthermore, this hypothesis is by no means universally accepted, in part because it has not yet been susceptible to direct testing. Pharmacological and electrical interventions lack the necessary specificity to selectively favor activity (in a manner fundamentally distinct from receptor modulation) of neocortical excitatory cells over inhibitory cells, whether in the clinical setting or in freely behaving experimental mammals during social and cognitive tasks. It is perhaps related to challenges such as this that the social and cognitive deficits of autism and schizophrenia have proven largely unresponsive to conventional psychopharmacology treatments in the clinic.

Optogenetics is the combination of genetic and optical methods used to control specific events in targeted cells of living tissue, even within freely moving mammals and other animals, with the temporal precision (millisecond-timescale) needed to keep pace with functioning intact biological systems. The hallmark of optogenetics is the introduction of fast light-activated channel proteins to the plasma membranes of target neuronal cells that allow temporally precise manipulation of neuronal membrane potential while maintaining cell-type resolution through the use of specific targeting mechanisms. Among the microbial opsins which can be used to investigate the function of neural systems are the channelrhodopsins (ChR2, ChR1, VChR1, and SFOs) used to promote depolarization in response to light. In just a few short years, the field of optogenetics has furthered the fundamental scientific understanding of how specific cell types contribute to the function of biological tissues such as neural circuits in vivo. Moreover, on the clinical side, optogenetics-driven research has led to insights into Parkinson's disease and other neurological and psychiatric disorders.

However, there are limitations to existing optogenetic tools for exploring the hypothesis that elevation in the ratio of cortical E/I balance might be associated with the social and cognitive deficits of autism and other disorders such as schizophrenia. Conventional channelrhodopsin photocurrents display significant desensitization which precludes the generation of step-like changes in E/I balance (instead requiring ramping or pulsing, which would not be suitable for investigation of stable changes in cellular E/I balance); moreover, both SFOs and conventional ChRs are driven by blue light, which precludes within-preparation comparison of the effects of driving different populations of circuit elements (such as excitatory and inhibitory neurons). Therefore, what is needed is a tool that would allow the manipulation of cortical E/I balances and the monitoring of gamma oscillations in cortical slices to permit the investigation of how these manipulations affect downstream neurons residing in the same microcircuit in the pre-frontal cortex.

BRIEF SUMMARY OF THE INVENTION

Provided herein are compositions comprising chimeric light-activated protein cation channels which are capable of mediating a depolarizing current in the cell when the cell is illuminated with light.

Provided herein are animal cells comprising a light-activated protein expressed on the cell membrane, wherein the protein is (a) a chimeric protein derived from VChR1 from *Volvox carteri* and ChR1 from *Chlamydomonas reinhardti*, wherein the protein comprises the amino acid sequence of VChR1 having at least the first and second transmembrane helices replaced by the first and second transmembrane helices of ChR1; (b) is responsive to light; and (c) is capable of mediating a depolarizing current in the cell when the cell is illuminated with light. In some embodiments, the cells are isolated or in a cell culture medium.

Also provided herein is a population of cells comprising the cell expressing the chimeric protein described herein on the cell membrane. Also provided herein are non-human animals and brain tissue slices comprising a cell expressing the chimeric protein described herein on the cell membrane.

Provided herein are polynucleotide comprising a nucleotide sequence encoding a light activated protein expressed on the cell membrane, wherein the protein is a chimeric protein derived from VChR1 from *Volvox carteri* and ChR1 from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. Vectors (such as expressing vectors) comprising the polynucleotides are also provided. In some embodiments, the expression vector is a viral vector (e.g., an AAV vector, a retroviral vector, an adenoviral vector, a HSV vector, or a lentiviral vector).

Also provided herein are methods of using the animal cells expressing the chimeric protein described herein on the cell membrane, the methods comprise activating the chimeric protein with light.

Also provided herein are methods of selectively depolarizing excitatory or inhibitory neurons residing in the same microcircuit, the methods comprising: selectively depolarizing an excitatory neuron comprising a first light-activated protein, wherein the first light activated protein is depolarized when exposed to light having a first wavelength; or selectively depolarizing an inhibitory neuron comprising a second light-activated protein, wherein the second light activated protein is depolarized when exposed to light having a second wavelength. In some embodiments, the first or the second light activated protein is a chimeric protein derived from VChR1 from *Volvox carteri* and ChR1 from *Chlamydomonas reinhardti*, wherein the protein comprises the amino acid sequence of VChR1 having at least the first and second transmembrane helices replaced by the first and second transmembrane helices of ChR1. In some embodiments, wherein the first light-activated protein comprises an amino acid sequence at least 95% identical to the sequence shown in SEQ ID NO: 1, 3, 5, or 7, and wherein the second light-activated protein comprises an amino acid sequence at least 95% identical to the sequence shown in SEQ ID NO:11, 12, 13, or 14.

A method of selectively depolarizing excitatory or inhibitory neurons residing in the same microcircuit, the method comprising: expressing a first light-activated protein in an excitatory neuron; and expressing a second light activated protein in an inhibitory neuron, wherein the first light activated protein is independently depolarized when exposed to light having a first wavelength and wherein the second light activated protein is independently depolarized when exposed to light having a second wavelength. In some embodiments, the first or the second light activated protein is a chimeric protein derived from VChR1 from *Volvox carteri* and ChR1 from *Chlamydomonas reinhardti*, wherein the protein comprises the amino acid sequence of VChR1 having at least the first and second transmembrane helices replaced by the first and second transmembrane helices of ChR1. In some embodiments, the first light-activated protein comprises an amino acid sequence at least 95% identical to the sequence shown in SEQ ID NO: 1, 3, 5, or 7, and wherein the second light-activated protein comprises an amino acid sequence at least 95% identical to the sequence shown in SEQ ID NO:11, 12, 13, or 14.

Also provided herein are methods for identifying a chemical compound that selectively inhibits the depolarization of excitatory or inhibitory neurons residing in the same microcircuit, the method comprising: (a) selectively depolarizing an excitatory neuron comprising a first light-activated protein with light having a first wavelength or selectively depolarizing an inhibitory neuron comprising a second light-activated protein with light having a second wavelength; (b) measuring an excitatory post synaptic potential (EPSP) in response to selectively depolarizing the excitatory neuron comprising a first light-activated protein or measuring an inhibitory post synaptic current (IPSC) in response to selectively depolarizing an inhibitory neuron comprising a second light-activated protein; (c) contacting the excitatory neuron or the inhibitory neuron with a chemical compound; (d) measuring the excitatory post synaptic potential (EPSP) or measuring the inhibitory post synaptic current (IPSC) to determine if contacting either the excitatory neuron or the inhibitory neuron with the chemical compound selectively inhibits the depolarization of either neuron. In some embodiments, the first or the second light activated protein is a chimeric protein derived from VChR1 from *Volvox carteri* and ChR1 from *Chlamydomonas reinhardti*, wherein the protein comprises the amino acid sequence of VChR1 having at least the first and second transmembrane helices replaced by the first and second transmembrane helices of ChR1. In some embodiments, the first light-activated protein comprises an amino acid sequence at least 95% identical to the sequence shown in SEQ ID NO: 1, 3, 5, or 7, and wherein the second light-activated protein comprises an amino acid sequence at least 95% identical to the sequence shown in SEQ ID NO:11, 12, 13, or 14.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1-8 depict engineering of an improved red-shifted channelrhodopsin for combinatorial optogenetics.

FIG. 1 depicts confocal images of cultured hippocampal neurons transfected with VChR 1-eYFP or C1V1-eYFP under the control of the CaMKIIa promoter. Box denotes region expanded in the last panel, showing dendritic membrane localization of C1V1-tsYFP. Scale bars: 20 µm (left), 4 µm (right).

FIG. 2 depicts peak photocurrents from whole-cell patch clamp recordings in-cultured hippocampal neurons expressing indicated opsins.

FIG. 3 depicts sequence alignment of ChR1 (SEQ ID NO:16), ChR2 (SEQ ID NO:11) and VChR1 (SEQ ID NO:17). Splice sites for two C1V1 variants are indicated. Putative transmembrane helices 1-7 are indicated with bars (TM1-7); mutated amino acids indicated in grey.

FIG. 4 depicts photocurrent amplitudes recorded in HEK cells expressing C1V1 splice variants 1 and 2.

FIG. 5 depicts single confocal plane images of cultured hippocampal neurons transfected with indicated opsins, fused to EYFP. DNA concentration was matched across constructs.

FIG. 6 depicts action spectra of ChR2, VChR1, C1V1 wt, C1V (E122T), C1V1 (E162T), and C1V1 (E122T/E162T). Photocurrents were collected with 2 ms light pulses in HEK293 cells.

FIG. 7 depicts ion permeance of C1V1 splice variant 1 as measured by photocurrent magnitude at −40 mV in HEK cells by whole cell patch clamp using cation-isolating external solutions. Data were normalized to the maximum peak Na current.

FIG. 8 depicts a schematic of the C1V1 chimera with point mutation positions indicated in white. ChR1 sequence indicated with black; VChR1 sequence with grey.

FIG. 9 depicts representative traces and summary plot of channel closure time constant ($\tau_{off}$) in cultured neurons expressing the indicated opsins; traces are normalized to peak current.

FIG. 10 depicts C1V1-E122T inactivation compared to deactivation of ChR2.

FIG. 11 depicts inactivation of current in C1V1 double mutant E122T/E162T versus other C1V1 variants.

FIG. 12 depicts mean peak photocurrents recorded in cultured neurons expressing the indicated opsins in response to a 2 ms 542 nm light pulse.

FIG. 13 depicts that peak photocurrents show consistent correlation with integrated fluorescence intensity.

FIG. 14 depicts fluorescence-photocurrent relationship in ChR2(H134R) and C1V1(E122T/E162T). Black lines are linear fits to the data.

FIG. 15 depicts acute slice recordings in prefrontal pyramidal neurons stimulated with 560 nm light pulse trains or current injections at the indicated frequencies Summary graph shows population data (n=6).

FIG. 16 depicts fraction of successful spikes to current injections (200 pA, 10 ms pulses; top left) or 2 ms light pulses at the indicated wavelengths and light power densities. All pulse trains consisted of 20×2 ms pulses delivered through the microscope objective using a Sutter DG-4 light source, filtered using 20 nm bandpass filters and additional neutral density filters to attenuate light power (n=6 cells in 2 slices).

FIG. 17 depicts voltage-clamp responses to 542 nm and 630 nm light pulses in cells expressing C1V1-E122T or C1V1-E 122T/E 162T (top). Current-clamp recording in a C1V1-E 122T expressing cell shows spiking in response to a 5 Hz train of 50 ms 630 nm light at 3.2 mW mm$^{-2}$ (bottom).

FIG. 18 depicts kinetics of red light response in C1V1 (E122T). Activation time constants ($\tau_{on}$) of photocurrents recorded from cultured neurons expressing C1V1(E122T) at 540 nm and 630 nm. Note that light powers were 3.2 mW mm-2 at 630 nm and 7.7 mW mm$^{-2}$ at 540 nm (n=5 cells, p=0.0006 paired t-test).

FIG. 19 depicts that voltage clamp traces show responses in a neuron expressing C1V1(E122T) to 630 nm light pulses. Pulse lengths are indicated above traces. $\tau_{on}$ calculated from the 150 ms trace is 67 ms.

FIG. 20 depicts current clamp recording from a neuron expressing C1V1(E122T) showing spikes elicited by 50 ms pulses at 630 nm (power density 3.2 mW mm$^{-2}$).

FIG. 21 depicts current clamp recordings from cultured hippocampal neurons expressing C1V1(E1 22T/E162T) or ChR2(H134R) in response to 2 ms light pulses at 560 nm or 405 nm (5 Hz; 7.6 mW/mm$^2$ at both wavelengths).

FIG. 22 depicts a recording configuration in double-injected animals expressing C1V1 in cortical pyramidal neurons and ChR2 (H134R) in inhibitory parvalbumin-positive interneurons. To independently express opsins, PV:: Cre mice were injected with a two-virus mix containing Lenti-CaMKIIα-C1V1(E122T/E162T) and AAV5-EF1a-DIO-Ch R2 (H 134R).

FIG. 23 depicts voltage clamp recordings from a non-expressing PYR neuron receiving synaptic input from C1V1-expressing PYR-cells and ChR2-expressing PV-cells. Clamped at OmV, 405 nm light pulses trigger short-latency IPSCs while 560 nm pulses evoke only small, long-latency inhibitory synaptic responses.

FIG. 24 depicts voltage clamp recording from the same cell shown in FIG. 23. Clamped at −65 mV, 560 nm light pulses trigger EPSCs but 405 nm pulses do not evoke detectable synaptic currents. Gray lines show individual events; black lines show light pulse-triggered averages.

FIG. 25 depicts an mPFC optrode recording in an anesthetized PV::Cre mouse injected with CaMKIIa::C1V1 (E162T)-ts-eYFP and Ef1a-DIO::ChR2-eYFP (diagram illustrates experimental setup). Violet (405 nm) light pulses are presented with variable delay (At) relative to green light pulses (example traces).

FIG. 26 depicts a summary graph shows probability of green light-evoked spikes with violet pulses preceding the green light pulses by the indicated delays. Individual points are from single recordings. Black line shows average for all recordings (>3 recording sites per bin).

FIG. 27 depicts an optrode recording from a mouse injected with viruses showing one presumed pyramidal unit and one presumed PV unit, firing in response to 561 nm stimulation (right, upper waveform) and 405 nm stimulation (right, lower waveform), respectively.

FIG. 28 depicts combinatorial projection control with C1V1-E122T/E 162T and ChR2-H134R in vitro. Experimental paradigm showing expression of C1V1 and ChR2 in cortico-thalamic (CT) and ventrobasal (VB) thalamo-cortical cells (TC), respectively.

FIG. 29 depicts that individual subthreshold inputs from TC and CT fibers lead to spiking in an nRT neuron only when inputs are precisely co-incident. Delays between CT and TC inputs are indicated on the left. Horizontal dashed lines indicate truncated spikes.

FIG. 30 depicts Voltage-clamp recording from an nRT cell receiving projections both from CT and TC cells. Simultaneous stimulation (Δt=0 ms) leads to a linear summation of evoked EPSCs from both projections.

FIG. 31 depicts normalized number of action potentials (from 6 nRT cells) evoked by CT and TC fibers activated with variable latencies (Δt) indicates that CT and TC inputs lead to effective integration only if coincident within 5 ms. Summary data represent mean±SEM.

FIG. 32 depicts temporal precision of C1V1 and ChR2 activation.

FIG. 33 depicts experimental paradigm for SSFO activation of PV neurons and C1V1 activation in pyramidal neurons.

FIG. 34 depicts voltage clamp recording at 0 mV from a pyramidal neuron in an acute slice preparation from a PV::Cre mouse expressing CaMKIIa::C1V1(E162T) and DIO-SSFO. SSFO and C1V1 are activated by a blue light pulse (2) and IPSC frequency is increased by sustained SSFO activity (3; compare upper and lower traces in inset for pre- and post-activation IPSC activity). A sustained yellow light pulse deactivates SSFO and activates C1V1 and transiently increases IPSC frequency (4). Population power spectra (right) show gamma frequency activity during optical excitatory neuron activation (590 nm pulse) that is increased during coactivation of excitatory and PV neurons (470 nm pulse). Diagrams below traces show predicted activity of C1V1 and SSFO during the experiment.

FIG. 35 depicts that the observed gamma frequency peak was not dependent on prior PV neuron stimulation via SSFO.

FIG. 36 depicts summary IPSC frequencies from FIG. 34 and FIG. 35 at baseline and after the initial blue or orange pulse. Diagrams below traces show predicted activity of C1V1 and SSFO during the experiment.

DETAILED DESCRIPTION

Figure 1:
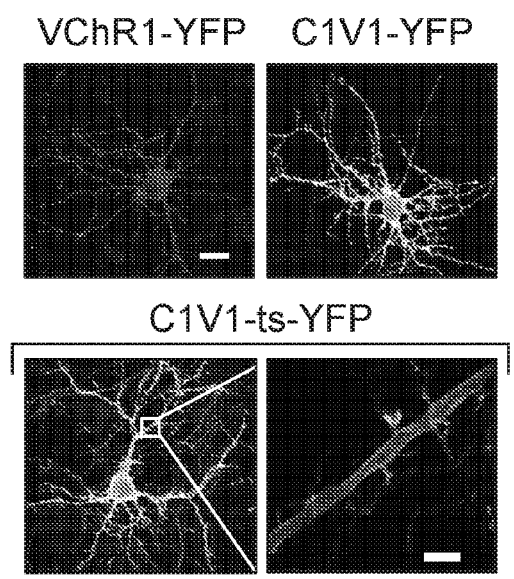

This invention provides, inter alia, compositions comprising animal cells expressing light-activated chimeric proteins on their plasma membranes and methods of using the same to selectively depolarize excitatory or inhibitory neurons residing in the same microcircuit in the pre-frontal cortex. The inventors have developed chimeric proteins possessing unique physiochemical properties which for the first time permit experimental manipulation of cortical E/I elevations and the ability to monitor gamma oscillations in cortical slices. These unique light-sensitive chimeric proteins can be expressed in either excitatory or inhibitory neural circuits in the prefrontal cortex of nonhuman animals which can then be depolarized in response to light having particular wavelengths. Furthermore, brain slices from non-human animals containing cortical excitatory or inhibitory neurons expressing the chimeric light-sensitive proteins disclosed herein can be used to search for chemical compounds which can selectively inhibit the depolarization of either excitatory or inhibitory neurons residing within the same neural circuit.

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987).

Definitions

As used herein, the singular form "a", "an", and "the" includes plural references unless indicated otherwise.

An "animal" can be a vertebrate, such as any common laboratory model organism, or a mammal. Mammals include, but are not limited to, humans, farm animals, sport animals, pets, primates, mice, rats, and other rodents.

An "amino acid substitution" or "mutation" as used herein means that at least one amino acid component of a defined amino acid sequence is altered or substituted with another amino acid leading to the protein encoded by that amino acid sequence having altered activity or expression levels within a cell.

A "chimeric protein" is a protein comprising one or more portions derived from one or more different proteins. Chimeric proteins may be produced by culturing a recombinant cell transfected with a nucleic acid that encodes the chimeric protein.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

V1C1 Chimeric Proteins and Cells Expressing the Same

In some aspects, the animal cells disclosed herein comprise a chimeric light-sensitive protein, known as "C1V1," which is derived from the VChR1 cation channel from *Volvox carteri* and the ChR1 cation channel from *Chlamydomonas Reinhardti*. The protein may be comprised of the amino acid sequence of VChR1, but additionally can have at least the first and second transmembrane helices of the VChR1 polypeptide replaced by the corresponding first and second transmembrane helices of ChR1. C1V1 chimeric opsin proteins are assembled from pieces of other opsin proteins that do not express well alone in neurons and which are potent, redshifted, and stable channelrhodopsins. In some embodiments, the animal cell may express a second light-activated protein on the plasma membrane of the cell. The second light-activated protein can be capable of mediating a hyperpolarization of the cell plasma membrane in response to activation by light. Examples of light-activated proteins capable of mediating a hyperpolarization of the cell plasma membrane can be found, for example, in International Patent Application No: PCT/US2011/028893, the disclosure of which is incorporated by reference herein in its entirety.

Embodiments of the present disclosure may also be directed toward modified or mutated versions of C1V1. These proteins can be used alone or in combination with a variety of other opsins to assert optical control over neurons. In particular, the use of modified C1V1, in connection with other opsins, is believed to be useful for optical control over nervous system disorders. Specific uses of C1V1 relate to optogenetic systems or methods that correlate temporal, spatial and/or cell type-specific control over a neural circuit with measurable metrics.

V1C1 Chimeric Proteins

Provided herein are light-activated chimeric proteins expressed on an animal cell plasma membrane. In some aspects the light-activated protein is a chimeric protein derived from VChR1 from *Volvox carteri* and ChR1 from *Chlamydomonas reinhardti*. In some embodiments, the chimeric protein comprises the amino acid sequence of VChR1 having at least the first and second transmembrane helices replaced by the corresponding first and second transmembrane helices of ChR1. In other embodiments, the chimeric protein comprises the amino acid sequence of VChR1 having the first and second transmembrane helices replaced by the corresponding first and second transmembrane helices of ChR1 and further comprises at least a portion of the intracellular loop domain located between the second and third transmembrane helices replaced by the corresponding portion from ChR1. In some embodiments, the entire intracellular loop domain between the second and third transmembrane helices of the chimeric light-activated protein can be replaced with the corresponding intracellular loop domain from ChR1. In other embodiments, the portion of the intercellular loop domain located between the second and third transmembrane helices that is replaced with the corresponding portion of ChR1 can extend to A145 of SEQ ID NO:1. In other embodiments, the chimeric protein comprises the amino acid sequence of VChR1 having the first and second transmembrane helices and the intracellular loop domain replaced by the corresponding first and second transmembrane helices and intracellular loop domain of ChR1 and further comprises at least a portion of the third transmembrane helix replaced by the corresponding portion of ChR1. In another embodiment, the portion of the third transmembrane helix replaced by the corresponding portion from ChR1 can extend to W163 of SEQ ID NO:1. In some embodiments, the light-activated chimeric protein comprises the amino acids 1-145 of ChR1 and amino acids 102-316 of VChR1. In some embodiments, the light-activated chimeric protein comprises the amino acids 1-162 of ChR1 and amino acids 119-316 of VChR1. In some embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 1 without the signal peptide sequence. In some embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 1

In other embodiments, the light activated chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 542 nm. In some embodiments, the chimeric protein may not be capable of mediating a depolarizing current in the cell when the cell is illuminated with violet light. In some embodiments, the chimeric protein may not be capable of mediating a depolarizing current in the cell when the cell is illuminated with light having a wavelength of 405 nm.

In some embodiments, the protein can further comprise a C-terminal fluorescent protein. In some specific embodiments, the C-terminal fluorescent protein can be enhanced yellow fluorescent protein (EYFP), green fluorescent protein (GFP), cyan fluorescent protein (CFP), or red fluorescent protein (RFP). In some embodiments, the light-activated chimeric protein is modified by the addition of a trafficking signal (ts) which enhances transport of the protein to the cell plasma membrane. In some embodiments, the trafficking signal is derived from the amino acid sequence of the human inward rectifier potassium channel Kir2.1. In some embodiments, the trafficking signal comprises the amino acid sequence KSRITSEGEYIPLDQIDINV (SEQ ID NO: 15). In some embodiments, the signal peptide sequence in the protein may be replaced with a different signal peptide sequence.

In some embodiments, the animal cell can be a neuronal cell, a muscle cell, or a stem cell. In one embodiment, the animal cell is a neuronal cell. In some embodiments the neuronal cell can be an excitatory neuron located in the pre-frontal cortex of a non-human animal. In other embodiments, the excitatory neuron can be a pyramidal neuron. In still other embodiments, the inhibitory neuron can be a parvalbumin neuron. In some embodiments the neuronal cell can be an inhibitory neuron located in the pre-frontal cortex of a non-human animal. In some embodiments the neuronal cell can be an inhibitory neuron located in the pre-frontal cortex of a non-human animal.

In some embodiments, the animal cells can further comprise a second light-activated protein expressed on the cells' plasma membrane. In some embodiments, the second light-activated protein can be capable of mediating a hyperpolarizing current in the cell when the cell is illuminated with light. In some embodiments the second light-activated protein can be NpHr, eNpHr2.0, eNpHr3.0, eNpHr3.1 or GtR3. Additional information regarding other light-activated cation channels, anion pumps, and proton pumps can be found in U.S. Patent Application Publication Nos: 2009/0093403; and International Patent Application No: PCT/US2011/028893, the disclosures of which are hereby incorporated by reference herein in their entirety. In some embodiments, the light-activated chimeric protein can have enhanced photocurrents in neural cells exposed to light relative to cells expressing other light-activated cation channel proteins. In some embodiments, the enhancement in photocurrent provided by the light-activated chimeric protein can be any of 1 fold, 2 fold, 3 fold, 4 fold, 5 fold, 6 fold, 7 fold, 8 fold, 9 fold, 10 fold, 11 fold, 12 fold, 13 fold, 14 fold, or 15 fold, greater than cells expressing other light-activated cation channel proteins, inclusive.

Also provided herein is one or more light-activated proteins expressed on an animal cell plasma membrane, wherein said one or more light activated proteins comprises a core amino acid sequence at least 90%, 91%, 92%, 93%, 94%, 95%, 96%, 97%, 98%, 99%, or 100% identical to the sequence shown in SEQ ID NO: 1, 3, 5, 7, 9, 11, 12, 13, or 14 and further comprising a trafficking signal (e.g., which enhances transport to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, an enhanced yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In some embodiments, the trafficking signal can comprise the amino acid sequence KSRITSEGEYIPLDQIDINV (SEQ ID NO: 15).

V1C1 Chimeric Mutant Variants

In some aspects, the invention includes polypeptides comprising substituted or mutated amino acid sequences, wherein the mutant polypeptide retains the characteristic light-activatable nature of the precursor C1V1 chimeric polypeptide but may also possess altered properties in some specific aspects. For example the mutant light-activated chimeric proteins described herein may exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-activated cation channels, and/or strong expression in animal cells.

Light-activated chimeric proteins comprising amino acid substitutions or mutations include those in which one or more amino acid residues have undergone an amino acid substitution while retaining the ability to respond to light and the ability to control the polarization state of a plasma membrane. For example, light-activated proteins comprising amino acid substitutions or mutations can be made by substituting one or more amino acids into the amino acid sequence corresponding to SEQ ID NO:1. In some embodiments, the invention includes proteins comprising altered amino acid sequences in comparison with the amino acid sequence in SEQ ID NO:1, wherein the altered light-activated chimeric protein retains the characteristic light-activated nature and/or the ability to regulate ion flow across plasma membranes of the protein with the amino acid sequence represented in SEQ ID NO:1 but may have altered properties in some specific aspects.

Amino acid substitutions in a native protein sequence may be conservative or non-conservative and such substituted amino acid residues may or may not be one encoded by the genetic code. The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine). A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The amino acid substitutions may be conservative or non-conservative. Additionally, the amino acid substitutions may be located in the C1V1 retinal binding pocket, in one or more of the C1V1 intracellular loop domains, and/or in both the retinal binding pocket or the intracellular loop domains.

Accordingly, provided herein are C1V1 chimeric light-activated proteins that may have specific amino acid substitutions at key positions throughout the retinal binding pocket of the VChR1 portion of the chimeric polypeptide. In some embodiments, the C1V1 protein can have a mutation at amino acid residue E122 of SEQ ID NO:1. In some embodiments, the C1V1 protein can have a mutation at amino acid residue E162 of SEQ ID NO:1. In other embodiments, the C1V1 protein can have a mutation at both amino acid residues E162 and E122 of SEQ ID NO:1. In some embodiments, each of the disclosed mutant C1V1 chimeric proteins can have specific properties and characteristics for use in depolarizing the membrane of an animal cell in response to light.

C1V1-E122 Mutant Polypeptides

Provided herein are the light-activated C1V1 chimeric proteins disclosed herein expressed on an animal cell plasma membrane, wherein one or more amino acid residues have undergone an amino acid substitution while retaining C1V1 activity (i.e., the ability to catalyze the depolarization of an animal cell in response to light activation), and wherein the mutation can be at a glutamic acid residue corresponding to E122 of SEQ ID NO:1 (C1V1-E122). In some embodiments, the C1V1-E122 mutant chimeric light-activated protein comprises substitutions introduced into the amino acid sequence shown in SEQ ID NO:1 at amino acid E122 that can result in the chimeric protein having increased sensitivity to light, increased sensitivity to particular wavelengths of light, and/or increased ability to regulate the polarization state of the plasma membrane of the cell relative to C1V1 chimeric light-activated proteins that do not have a mutation at E122. In some embodiments, the mutation can be a conservative amino acid substitution. In some embodiments, the mutation can be a non-conservative amino acid substitution. In some embodiments, the mutation at amino acid residue E122 can be to threonine (C1V1-E122T). In other embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 3 without the signal peptide sequence. In other embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 3. In other embodiments, the C1V1-E122 mutant chimeric light-activated protein may be fused to a C-terminal trafficking signal. In some embodiments, the trafficking signal can be linked to the C1V1-E122 mutant chimeric light-activated protein by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, an enhanced yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In some embodiments, the trafficking signal can comprise the amino acid sequence KSRITSEGEYIPLDQIDINV (SEQ ID NO: 15).

In other embodiments, the C1V1-E122 chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 chimeric protein can mediate a depolarizing current in the cell when the cell is illuminated with red light. In some embodiments, the red light can have a wavelength of about 630 nm. In some embodiments, the C1V1-E122 chimeric protein may not be capable of mediating a depolarizing current in the cell when the cell is illuminated with violet light. In some embodiments, the chimeric protein may not be capable of mediating a depolarizing current in the cell when the cell is illuminated with light having a wavelength of 405 nm. In some embodiments, the animal cell can be a neuronal cell, a muscle cell, or a stem cell. In one embodiment, the animal cell can be a neuronal cell. In some embodiments the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In other embodiments, the excitatory neuron can be a pyramidal neuron. In still other embodiments, the inhibitory neuron can be a parvalbumin neuron. In some embodiments, the animal cells can further comprise a second light-activated protein expressed on the cells' plasma membrane. In some embodiments, the second light-activated protein can be capable of mediating a hyperpolarizing current in the cell when the cell is illuminated with light. In some embodiments the second light-activated protein can be NpHr, eNpHr2.0, eNpHr3.0, eNpHr3.1 or GtR3.

C1V1-E162 Mutant Polypeptides

Provided herein are the light-activated C1V1 chimeric proteins disclosed herein expressed on an animal cell plasma membrane, wherein one or more amino acid residues have undergone an amino acid substitution while retaining C1V1 activity (i.e., the ability to catalyze the depolarization of an animal cell in response to light activation), wherein the mutation can be at a glutamic acid residue corresponding to E162 of SEQ ID NO:1 (C1V1-E162). In some embodiments, the C1V1-E162 mutant chimeric light-activated protein comprises substitutions introduced into the amino acid sequence shown in SEQ ID NO:1 at amino acid E162 that can result in the chimeric protein having increased sensitivity to light, increased sensitivity to particular wavelengths of light, and/or increased ability to regulate the polarization state of the plasma membrane of the cell relative to C1V1 chimeric light-activated proteins that do not have a mutation at E162. In some embodiments, the mutation can be a conservative amino acid substitution. In some embodiments, the mutation can be a non-conservative amino acid substitution. In some embodiments, the mutation at amino acid residue E162 can be to threonine (C1V1-E162T). In other embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 5 without the signal peptide sequence. In other embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 5. In other embodiments, the C1V1-E162 mutant chimeric light-activated protein may be fused to a C-terminal trafficking signal. In some embodiments, the trafficking signal can be linked to the C1V1-E162 mutant chimeric light-activated protein by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, an enhanced yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In some embodiments, the trafficking signal can comprise the amino acid sequence KSRITSEGEYIPLDQIDINV (SEQ ID NO: 15).

In other embodiments, the C1V1-E162 chimeric protein is capable of mediating a depolarizing current in the cell when the cell is illuminated with light. In some embodiments the light can be green light. In other embodiments, the light can have a wavelength of between about 540 nm to about 535 nm. In some embodiments, the light can have a wavelength of about 542 nm. In other embodiments, the light can have a wavelength of about 530 nm. In some embodiments, the C1V1-E162 chimeric protein may not be capable of mediating a depolarizing current in the cell when the cell is illuminated with violet light. In some embodiments, the chimeric protein may not be capable of mediating a depolarizing current in the cell when the cell is illuminated with light having a wavelength of 405 nm. In some embodiments, the C1V1-E162 chimeric protein can further comprise a C-terminal fluorescent protein. In some embodiments, the animal cell can be a neuronal cell, a muscle cell, or a stem cell. In one embodiment, the animal cell can be a neuronal cell. In some embodiments the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In other embodiments, the excitatory neuron can be a pyramidal neuron. In still other embodiments, the inhibitory neuron can be a parvalbumin neuron. In some embodiments, the animal cells can further comprise a second light-activated protein expressed on the cells' plasma membrane. In some embodiments, the second light-activated protein can be capable of mediating a hyperpolarizing current in the cell when the cell is illuminated with light. In some embodiments the second light-activated protein can be NpHr, eNpHr2.0, eNpHr3.0, eNpHr3.1 or GtR3. In some embodiments, the C1V1-E162 light-activated chimeric protein can have an accelerated photocycle relative C1V1 proteins lacking mutations at E162 or relative to other light-activated cation channel proteins. In some embodiments, the C1V1-E162 light-activated chimeric protein can have a photocycle more than 1 fold, 1.5 fold, 2 fold, 2.5 fold, 3 fold, 3.5 fold, 4 fold, 4.5 fold, or 5 fold faster than C1V1 proteins lacking mutations at E162 or relative to other light-activated cation channel proteins, inclusive.

C1V1-E122/E162 Double Mutant Polypeptides

Provided herein are the light-activated C1V1 chimeric proteins disclosed herein expressed on an animal cell plasma membrane, wherein one or more amino acid residues have undergone an amino acid substitution while retaining C1V1 activity (i.e., the ability to catalyze the depolarization of an animal cell in response to light activation), wherein the mutations can be at glutamic acid residues corresponding to E122 and E162 of SEQ ID NO:1 (C1V1-E122/E162). In some embodiments, the C1V1-E122/E162 mutant chimeric light-activated protein can comprise substitutions introduced into the amino acid sequence shown in SEQ ID NO:1 at amino acid E122 and E162 that can result in the chimeric protein having increased sensitivity to light, increased sensitivity to particular wavelengths of light, and/or increased ability to regulate the polarization state of the plasma membrane of the cell relative to C1V1 chimeric light-activated proteins that do not have a mutation at E122 and E162. In some embodiments, the mutations can be conservative amino acid substitutions. In some embodiments, the mutations can be non-conservative amino acid substitutions. In some embodiments, the mutations can be both conservative and non-conservative amino acid substitutions. In some embodiments, the mutation at amino acid residue E122 and at E162 can both be to threonine (C1V1-E122T/E162T). In other embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 7 without the signal peptide sequence. In other embodiments, the light-activated chimeric protein can comprise an amino acid sequence at least 90%, 91%, 92%, 93%, 94%, 95%, 96%, 97%, 98%, 99%, or 100% identical to the sequence shown in SEQ ID NO: 7. In other embodiments, the C1V1-E122/E162 mutant chimeric light-activated protein may be fused to a C-terminal trafficking signal. In some embodiments, the trafficking signal can be linked to the C1V1-E122/E162 mutant chimeric light-activated protein by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, an enhanced yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In some embodiments, the trafficking signal can comprise the amino acid sequence KSRITSEGEYIPLDQ-IDINV (SEQ ID NO: 15).

In other embodiments, the C1V1-E122/E162 chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 chimeric protein may not be capable of mediating a depolarizing current in the cell when the cell is illuminated with violet light. In some embodiments, the chimeric protein may not be capable of mediating a depolarizing current in the cell when the cell is illuminated with light having a wavelength of 405 nm. In some embodiments, the C1V1-E122/E162 chimeric protein can exhibit less activation when exposed to violet light relative to C1V1 proteins lacking mutations at E122/E162 or relative to other light-activated cation channel proteins. In some embodiments, the animal cell can be a neuronal cell, a muscle cell, or a stem cell. In one embodiment, the animal cell can be a neuronal cell. In some embodiments the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In still other embodiments, the inhibitory neuron can be a parvalbumin neuron. In some embodiments, the animal cells can further comprise a second light-activated protein expressed on the cells' plasma membrane. In some embodiments, the second light-activated protein can be capable of mediating a hyperpolarizing current in the cell when the cell is illuminated with light. In some embodiments the second light-activated protein can be NpHr, eNpHr2.0, eNpHr3.0, eNpHr3.1 or GtR3. In some embodiments, the C1V1-E122/E162 mutant light-activated chimeric protein can have decreased inactivation relative to C1V1 proteins lacking mutations at E122/E162 or relative to other light-activated cation channel proteins. In some embodiments, the C1V1-E122/E162 mutant light-activated chimeric protein can inactivate by any of about 15%, 16%, 17%, 18%, 19%, 20%, 21%, 22%, 23%, 24%, 25%, 26 v, 27%, 28%, 29%, or 30% compared to C1V1 proteins lacking mutations at E122/E162 or relative to other light-activated cation channel proteins, inclusive. In some embodiments, the C1V1-E122/E162 light-activated chimeric protein can have a photocycle more than 1 fold, 1.5 fold, 2 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, or 10 fold faster than C1V1 proteins lacking mutations at E122/E162 or relative to other light-activated cation channel proteins, inclusive.

Enhanced Intracellular Transport Amino Acid Motifs

The present disclosure provides for the modification of light-activated chimeric proteins expressed in a cell by the addition of one or more amino acid sequence motifs which enhance transport to the plasma membranes of mammalian cells. Light-activated chimeric proteins having components derived from evolutionarily simpler organisms may not be expressed or tolerated by mammalian cells or may exhibit impaired subcellular localization when expressed at high levels in mammalian cells. Consequently, in some embodiments, the chimeric light-activated protein expressed in a cell is fused to one or more amino acid sequence motifs selected from the group consisting of a signal peptide, an endoplasmic reticulum (ER) export signal, a membrane trafficking signal, and an N-terminal golgi export signal. The one or more amino acid sequence motifs which enhance light-activated chimeric protein transport to the plasma membranes of mammalian cells can be fused to the N-terminus, the C-terminus, or to both the N- and C-terminal ends of the light-activated protein. Optionally, the light-activated protein and the one or more amino acid sequence motifs may be separated by a linker. In some embodiments, the light-activated chimeric protein is modified by the addition of a trafficking signal (ts) which enhances transport of the protein to the cell plasma membrane. In some embodiments, the trafficking signal is derived from the amino acid sequence of the human inward rectifier potassium channel Kir2.1. In some embodiments, the trafficking signal comprises the amino acid sequence KSRITSEGEYIPLDQIDINV (SEQ ID NO: 15). Additional protein motifs which can enhance light-activated protein transport to the plasma membrane of a cell are described in U.S. patent application Ser. No. 12/041,628, which is incorporated herein by reference in its entirety. In some embodiments, the signal peptide sequence in the chimeric protein is deleted or substituted with a signal peptide sequence from a different protein.

Animal Cells, Non-Human Animals, and Brain Slices

Provided herein are cells comprising the light activated chimeric proteins disclosed herein. In some embodiments, the cells are animal cells. In some embodiments, the animal cells comprise the C1V1 protein corresponding to SEQ ID NO:1. In other embodiments, the animal cells comprise the mutant C1V1-E122T protein corresponding to SEQ ID NO:3. In other embodiments, the animal cells comprise the mutant C1V1-E162T protein corresponding to SEQ ID NO:5. In other embodiments, the animal cells comprise the mutant C1V1-E122T/E162T protein corresponding to SEQ ID NO7. In some embodiments, the animal cell can be a neuronal cell, a muscle cell, or a stem cell. In one embodiment, the animal cell can be a neuronal cell. In some embodiments the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In still other embodiments, the inhibitory neuron can be a parvalbumin neuron.

Also provided herein, are non-human animals comprising the light activated chimeric proteins disclosed herein expressed on the cell membrane of the cells in the animals. In some embodiments, the animal cells comprise the C1V1 protein corresponding to SEQ ID NO:1. In other embodiments, the animal cells comprise the mutant C1V1-E122T protein corresponding to SEQ ID NO:3. In other embodiments, the animal cells comprise the mutant C1V1-E162T protein corresponding to SEQ ID NO:5. In other embodiments, the animal cells comprise the mutant C1V1-E122T/E162T protein corresponding to SEQ ID NO7. In some embodiments, the animals comprising the light-activated chimeric proteins described herein are transgenically expressing said light-activated chimeric proteins. In other embodiments, the animals comprising the light-activated chimeric proteins described herein have been virally transfected with a vector carrying the light-activated protein such as, but not limited to, an adenoviral vector.

Provided herein are living brain slices from a non-human animal comprising the light-activated chimeric proteins described herein expressed on the cell membrane of the cells in the slices. In some embodiments, the brain slices are from non-human animals transgenically expressing the light-activated chimeric proteins described herein. In other embodiments, the brain slices are from non-human animals that have been virally transfected with a vector carrying said light-activated protein such as, but not limited to, an adenoviral vector. In some embodiments, the brain slices are coronal brain slices. In some embodiments, the brain slices are any of about 100 μm, about 150 μm, about 200 μm, about 250 μm, about 300 μm, about 350 μm, about 400 μm, about 450 μm, or about 500 μm thick, inclusive, including any thicknesses in between these numbers.

Isolated Polynucleotides

Provided herein are isolated C1V1 polynucleotides that encode any chimeric polypeptides described herein that, for example, have at least one activity of a C1V1 polypeptide. The disclosure provides isolated, synthetic, or recombinant polynucleotides comprising a nucleic acid sequence having at least about 70%, e.g., at least about 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, or 99%, or complete (100%) sequence identity to the nucleic acid of SEQ ID NO:2, 4, 6 or 8 over a region of at least about 10, e.g., at least about 15, 20, 25, 30, 35, 40, 45, 50, 75, 100, 150, 200, 250, 300, 350, 400, 450, 500, 550, 600, 650, 700, 750, 800, 850, 900, 950, or 1000 nucleotides.

The disclosure specifically provides a nucleic acid encoding C1V1 and/or a mutant variant thereof. For example, the disclosure provides an isolated nucleic acid molecule, wherein the nucleic acid molecule encodes: (1) a polypeptide comprising an amino acid sequence with at least 90%, 91%, 92%, 93%, 94%, 95%, 96%, 97%, 98%, 99% or 100% sequence identity to the amino acid sequence of SEQ ID NO:1; (2) a polypeptide comprising an amino acid sequence with at least 90%, 91%, 92%, 93%, 94%, 95%, 96%, 97%, 98%, 99% or 100% sequence identity to the amino acid sequence of SEQ ID NO:3, (3) a polypeptide comprising an amino acid sequence with at least 90%, 91%, 92%, 93%, 94%, 95%, 96%, 97%, 98%, 99% or 100% sequence identity to the amino acid sequence of SEQ ID NO:5; or (4) a polypeptide comprising an amino acid sequence with at least 90%, 91%, 92%, 93%, 94%, 95%, 96%, 97%, 98%, 99% or 100% sequence identity to the amino acid sequence represented by SEQ ID NO:7.

Promoters and Vectors

The disclosure also provides expression cassettes and/or vectors comprising the above-described nucleic acids. Suitably, the nucleic acid encoding a chimeric protein of the disclosure is operably linked to a promoter. Promoters are well known in the art. Any promoter that functions in the host cell can be used for expression of C1V1 and/or any variant thereof of the present disclosure. Initiation control regions or promoters, which are useful to drive expression of a C1V1 chimeric protein or variant thereof in a specific animal cell are numerous and familiar to those skilled in the art. Virtually any promoter capable of driving these nucleic acids can be used.

Specifically, where recombinant expression of C1V1 chimeric proteins in an excitatory neural cell is desired, a human calmodulin-dependent protein kinase II alpha (CaMKIIα) promoter may be used. In other embodiments, an elongation factor 1a (EF-1a) promoter in conjunction with a Cre-inducible recombinant AAV vector can be used with parvalbumin-Cre transgenic mice to target expression C1V1 chimeric proteins to inhibitory neurons.

Also provided herein are vectors comprising the polynucleotides disclosed herein encoding a C1V1 chimeric polypeptide or any variant thereof. The vectors that can be administered according to the present invention also include vectors comprising a polynucleotide which encodes an RNA (e.g., RNAi, ribozymes, miRNA, siRNA) that when transcribed from the polynucleotides of the vector will result in the accumulation of light-activated chimeric proteins on the plasma membranes of target animal cells. Vectors which may be used, include, without limitation, lentiviral, HSV, and adenoviral vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and site specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The application of AAV as a vector for gene therapy has been rapidly developed in recent years. Wild-type AAV could infect, with a comparatively high titer, dividing or non-dividing cells, or tissues of mammal, including human, and also can integrate into in human cells at specific site (on the long arm of chromosome 19) (Kotin, R. M., et al, *Proc. Natl. Acad. Sci. USA* 87: 2211-2215, 1990) (Samulski, R. J, et al, *EMBO J.* 10: 3941-3950, 1991 the disclosures of which are hereby incorporated by reference herein in their entireties). AAV vector without the rep and cap genes loses specificity of site-specific integration, but may still mediate long-term stable expression of exogenous genes. AAV vector exists in cells in two forms, wherein one is episomic outside of the chromosome; another is integrated into the chromosome, with the former as the major form. Moreover, AAV has not hitherto been found to be associated with any human disease, nor any change of biological characteristics arising from the integration has been observed. There are sixteen serotypes of AAV reported in literature, respectively named AAV1, AAV2, AAV3, AAV4, AAV5, AAV6, AAV7, AAV8, AAV9, AAV10, AAV11, AAV12, AAV13, AAV14, AAV15, and AAV16, wherein AAV5 is originally isolated from humans (Bantel-Schaal, and H. zur Hausen. 1984. *Virology* 134: 52-63), while AAV1-4 and AAV6 are all found in the study of adenovirus (Ursula Bantel-Schaal, Hajo Delius and Harald zur Hausen. *J. Virol.* 1999, 73: 939-947).

AAV vectors may be prepared using standard methods in the art. Adeno-associated viruses of any serotype are suitable (See, e.g., Blacklow, pp. 165-174 of "*Parvoviruses and Human Disease*" J. R. Pattison, ed. (1988); Rose, *Compre*- hensive *Virology* 3:1, 1974; P. Tattersall "The Evolution of Parvovirus Taxonomy" In *Parvoviruses* (J R Kerr, S F Cotmore. M E Bloom, R M Linden, C R Parrish, Eds.) p 5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p 15-23, Hudder Arnold, London, UK (2006), the disclosures of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos: 91/18088 and WO 93/09239; U.S. Pat. Nos. 4,797,368, 6,596,535, and 5,139,941; and European Patent No: 0488528, all of which are herein incorporated by reference in their entirety). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the invention are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the invention includes a recombinant virus particle (recombinant because it contains a recombinant polynucleotide) comprising any of the vectors described herein. Methods of producing such particles are known in the art and are described in U.S. Pat. No. 6,596,535.

For the animal cells described herein, it is understood that one or more vectors may be administered to neural cells, heart cells, or stem cells. If more than one vector is used, it is understood that they may be administered at the same or at different times to the animal cell.

Methods of the Invention

Provided herein are methods for selectively depolarizing excitatory or inhibitory neurons residing in the same microcircuit by expressing in those neurons the light-activated chimeric proteins described herein. In some embodiments, a first light-activated protein, such as those disclosed herein, can be expressed in an excitatory neuron while a second light-activated protein can be expressed in an inhibitory neuron. In some embodiments, the first light-activated protein expressed in the excitatory neuron can be activated by a different wavelength of light than the second light-activated protein expressed in the inhibitory neuron. In some embodiments, the first and second light-activated proteins can be expressed in a living non-human animal or in a living brain slice from a non-human animal.

In other embodiments, a method is provided for identifying a chemical compound that selectively inhibits the depolarization of excitatory or inhibitory neurons residing in the same neural circuit by expressing in those neurons the light-activated chimeric proteins described herein. In some embodiments, a first light-activated protein can be expressed in an excitatory neuron while a second light-activated protein can be expressed in an inhibitory neuron. In some embodiments, the first light-activated protein expressed in the excitatory neuron can be activated by a different wavelength of light than the second light-activated protein expressed in the inhibitory neuron. In some embodiments, the first and second light-activated proteins can be expressed in a living non-human animal or in a living brain slice from a non-human animal.

Methods for Selectively Altering the E/I Balance in Neurons Residing in the Same Microcircuit In some aspects, there is provided a method for selectively depolarizing excitatory or inhibitory neurons residing in the same microcircuit, the method comprising: selectively depolarizing an excitatory neuron comprising a first light-activated protein, wherein the first light-activated protein is depolarized when exposed to light having a first wavelength or selectively depolarizing an inhibitory neuron comprising a second light-activated protein, wherein the second light-activated protein is depolarized when exposed to light having a second wavelength. In some embodiments, the first light-activated protein can comprise a protein at least 90%, 91%, 92%, 93%, 94%, 95%, 96%, 97%, 98%, 99% or 100% identical to the amino acid sequence shown in SEQ ID NO: 1. In other embodiments, the first light-activated protein can comprise a protein at least 90%, 91%, 92%, 93%, 94%, 95%, 96%, 97%, 98%, 99% or 100% identical to the amino acid sequence shown in SEQ ID NO: 3. In some embodiments, the first light-activated protein can comprise a protein at least 90%, 91%, 92%, 93%, 94%, 95%, 96%, 97%, 98%, 99% or 100% identical to the amino acid sequence shown in SEQ ID NO: 5. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:11. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:12. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO: 13. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO: 14. More information regarding the disclosure of other light-activated cation channels can be found in U.S. Patent Application Publication No: 2007/0054319; U.S. Patent Application No. 61/410,704; and International Patent Application Publication No: WO 2010/056970, the disclosures of each of which are hereby incorporated by reference in their entireties.

In other aspects, there is provided a method for selectively depolarizing excitatory or inhibitory neurons residing in the same microcircuit, the method comprising: expressing a first light-activated protein in an excitatory neuron; and expressing a second light-activated protein in an inhibitory neuron, wherein the first light-activated protein is independently depolarized when exposed to light having a first wavelength and wherein the second light-activated protein is independently depolarized when exposed to light having a second wavelength. In some embodiments, the first light-activated protein can comprise a protein at least 90%, 91%, 92%, 93%, 94%, 95%, 96%, 97%, 98%, 99% or 100% identical to the amino acid sequence shown in SEQ ID NO: 1. In other embodiments, the first light-activated protein can comprise a protein at least 90%, 91%, 92%, 93%, 94%, 95%, 96%, 97%, 98%, 99% or 100% identical to the amino acid sequence shown in SEQ ID NO: 3. In some embodiments, the first light-activated protein can comprise a protein at least 90%, 91%, 92%, 93%, 94%, 95%, 96%, 97%, 98%, 99% or 100% identical to the amino acid sequence shown in SEQ ID NO: 5. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:11. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:12. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:13. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:14.

In some embodiments, the first light-activated protein can be activated by green light. In one embodiment, the first light-activated protein can be activated by light having a wavelength of about 560 nm. In one embodiment, the first light-activated protein can be activated by red light. In another embodiment, the first light-activated protein can be activated by light having a wavelength of about 630 nm. In other embodiments, the second light-activated protein can be activated by violet light. In one embodiment, the second light-activated protein can be activated by light having a wavelength of about 405 nm. In other embodiments, the second light activated protein can be activated by green light. In some embodiments, the light-activated proteins are activated by light pulses that can have a duration for any of about 1 millisecond (ms), about 2 ms, about 3, ms, about 4, ms, about 5 ms, about 6 ms, about 7 ms, about 8 ms, about 9 ms, about 10 ms, about 15 ms, about 20 ms, about 25 ms, about 30 ms, about 35 ms, about 40 ms, about 45 ms, about 50 ms, about 60 ms, about 70 ms, about 80 ms, about 90 ms, about 100 ms, about 200 ms, about 300 ms, about 400 ms, about 500 ms, about 600 ms, about 700 ms, about 800 ms, about 900 ms, about 1 sec, about 1.25 sec, about 1.5 sec, or about 2 sec, inclusive, including any times in between these numbers. In some embodiments, the light-activated proteins are activated by light pulses that can have a light power density of any of about 0.05 mW $mm^{-2}$, about 0.1 mW $mm^{-2}$, about 0.25 mW $mm^{-2}$, about 0.5 mW $mm^{-2}$, about 0.75 mW $mm^{-2}$, about 1 mW $mm^{-2}$, about 2 mW $mm^{-2}$, about 3 mW $mm^{-2}$, about 4 mW $mm^{-2}$, about 5 mW $mm^{-2}$, about 6 mW $mm^{-2}$, about 7 mW $mm^{-2}$, about 8 mW $mm^{-2}$, about 9 mW $mm^{-2}$, about 10 mW $mm^{-2}$, about 11 mW $mm^{-2}$, about 12 mW $mm^{-2}$, about 13 mW $mm^{-2}$, about 14 mW $mm^{-2}$, about mW $mm^{-2}$, about 16 mW $mm^{-2}$, about 17 mW $mm^{-2}$, about 18 mW $mm^{-2}$, about 19 mW $mm^{-2}$, about 20 mW $mm^{-2}$, about 21 mW $mm^{-2}$, about 22 mW $mm^{-2}$, about 23 mW $mm^{-2}$, about 24 mW $mm^{-2}$, or about 25 mW $mm^{-2}$, inclusive, including any values between these numbers. In some embodiments the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In still other embodiments, the inhibitory neuron can be a parvalbumin neuron. In some embodiments, the inhibitory and excitatory neurons can be in a living non-human animal. In other embodiments, the inhibitory and excitatory neurons can be in a brain slice from a non-human animal.

Methods for Identifying a Chemical Compound that Selectively Alters the E/I Balance in Neurons Residing in the Same Microcircuit In some aspects, there is provided a method for identifying a chemical compound that selectively inhibits the depolarization of excitatory or inhibitory neurons residing in the same microcircuit, the method comprising: (a) selectively depolarizing an excitatory neuron comprising a first light-activated protein with light having a first wavelength or selectively depolarizing an inhibitory neuron comprising a second light-activated protein with light having a second wavelength; (b) measuring an excitatory post synaptic potential (EPSP) in response to selectively depolarizing the excitatory neuron comprising a first light-activated protein or measuring an inhibitory post synaptic current (IPSC) in response to selectively depolarizing an inhibitory neuron comprising a second light-activated protein; (c) contacting the excitatory neuron or the inhibitory neuron with a chemical compound; (d) measuring the excitatory post synaptic potential (EPSP) or measuring the inhibitory post synaptic current (IPSC) to determine if contacting either the excitatory neuron or the inhibitory neuron with the chemical compound selectively inhibits the depolarization of either neuron. In some embodiments, the first light-activated protein can comprise a protein at least 90%, 91%, 92%, 93%, 94%, 95%, 96%, 97%, 98%, 99% or 100% identical to the amino acid sequence shown in SEQ ID NO: 1. In other embodiments, the first light-activated protein can comprise a protein at least 90%, 91%, 92%, 93%, 94%, 95%, 96%, 97%, 98%, 99% or 100% identical to the amino acid sequence shown in SEQ ID NO: 3. In some embodiments, the first light-activated protein can comprise a protein at least 90%, 91%, 92%, 93%, 94%, 95%, 96%, 97%, 98%, 99% or 100% identical to the amino acid sequence shown in SEQ ID NO: 5. In some aspects, the second light-activated protein can comprise a protein at least 90%, 91%, 92%, 93%, 94%, 95%, 96%, 97%, 98%, 99% or 100% identical to the amino acid sequence shown in SEQ ID NO:11. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:12. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:13. In some embodiments, the second light-activated protein can comprise a protein at least 90%, 91%, 92%, 93%, 94%, 95%, 96%, 97%, 98%, 99% or 100% identical to the amino acid sequence shown in SEQ ID NO:14. In some embodiments, the chemical compound can be a member of a combinatorial chemical library. In other embodiments, the method further comprises assaying the chemical compound to determine if it adversely affects the function of cardiac tissue or the cardiac action potential in mammals.

In some embodiments, the first light-activated protein can be activated by green light. In one embodiment, the first light-activated protein can be activated by light having a wavelength of about 560 nm. In one embodiment, the first light-activated protein can be activated by red light. In another embodiment, the first light-activated protein can be activated by light having a wavelength of about 630 nm. In other embodiments, the second light-activated protein can be activated by violet light. In one embodiment, the second light-activated protein can be activated by light having a wavelength of about 405 nm. In some embodiments, the light-activated proteins can be activated by light pulses that can have a duration for any of about 1 millisecond (ms), about 2 ms, about 3, ms, about 4, ms, about 5 ms, about 6 ms, about 7 ms, about 8 ms, about 9 ms, about 10 ms, about 15 ms, about 20 ms, about 25 ms, about 30 ms, about 35 ms, about 40 ms, about 45 ms, about 50 ms, about 60 ms, about 70 ms, about 80 ms, about 90 ms, about 100 ms, about 200 ms, about 300 ms, about 400 ms, about 500 ms, about 600 ms, about 700 ms, about 800 ms, about 900 ms, about 1 sec, about 1.25 sec, about 1.5 sec, or about 2 sec, inclusive, including any times in between these numbers. In some embodiments, the light-activated proteins can be activated by light pulses that can have a light power density of any of about 0.05 mW $mm^{-2}$, about 0.1 mW $mm^{-2}$, about 0.25 mW $mm^{-2}$, about 0.5 mW $mm^{-2}$, about 0.75 mW $mm^{-2}$, about 1 mW $mm^{-2}$, about 2 mW $mm^{-2}$, about 3 mW $mm^{-2}$, about 4 mW $mm^{-2}$, about 5 mW $mm^{-2}$, about 6 mW $mm^{-2}$, about 7 mW $mm^{-2}$, about 8 mW $mm^{-2}$, about 9 mW $mm^{-2}$, about 10 mW $mm^{-2}$, about 11 mW $mm^{-2}$, about 12 mW $mm^{-2}$, about 13 mW $mm^{-2}$, about 14 mW $mm^{-2}$, about mW $mm^{-2}$, about 16 mW $mm^{-2}$, about 17 mW $mm^{-2}$, about 18 mW $mm^{-2}$, about 19 mW $mm^{-2}$, about 20 mW $mm^{-2}$, about 21 mW $mm^{-2}$, about 22 mW $mm^{-2}$, about 23 mW $mm^{-2}$, about 24 mW $mm^{-2}$, or about 25 mW $mm^{-2}$, inclusive, including any values between these numbers. In some embodiments the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In still other embodiments, the inhibitory neuron can be a parvalbumin neuron. In some embodiments, the inhibitory and excitatory neurons can be in a living non-human animal. In other embodiments, the inhibitory and excitatory neurons can be in a brain slice from a non-human animal.

Exemplary Embodiments

The present disclosure relates to a light-activated chimera opsin that modifies a membrane voltage when expressed therein. While the present disclosure is not necessarily limited in these contexts, various aspects of the disclosure may be appreciated through a discussion of examples using these and other contexts.

Various embodiments of the present disclosure relate to a light-activated opsin modified for expression in cell membranes including mammalian cells. The opsin is derived from a combination of two different opsins, *Volvox* channelrhodopsin (VChR1) and *Chlamydomonas reinhardtii* channelrhodopsin (ChR1). The opsin can be useful for expressing at levels of a higher rate than either of the individual opsins from which it is derived.

In certain more specific embodiments, the genetic sequence of ChR1/VChR1 chimera (C1V1) is primarily VChR1. Portions of the VChR1 sequence associated with trafficking are replaced with homologous sequences from ChR1.

Various embodiments relate to modification directed toward the addition of a trafficking signal to improve expression in mammalian cells.

Certain aspects of the present disclosure are directed to further modified versions of C1V1. For example, certain embodiments include a mutation E162T to C1V1, which experiments suggest provides an accelerated photocycle (e.g., almost 3-fold).

Various embodiments of the present disclosure relate to an optogenetic system or method that correlates temporal, spatial and/or cell-type-specific control over a neural circuit with measurable metrics. The optogenetic system uses a variety of opsins, including C1V1 and/or C1V1 variants, to assert control over portions of neural circuits. For instance, various metrics or symptoms might be associated with a neurological disorder. The optogenetic system targets a neural circuit within a patient for selective control thereof. The optogenetic system involves monitoring the patient for the metrics or symptoms associated with the neurological disorder. In this manner, the optogenetic system can provide detailed information about the neural circuit, its function and/or the neurological disorder.

Consistent with the embodiments discussed herein, particular embodiments relate to studying and probing disorders using a variety of opsins. Other embodiments relate to the identification and/or study of phenotypes and endophenotypes. Still other embodiments relate to the identification of treatment targets.

Aspects of the present disclosure are directed toward the artificial inducement of disorder/disease states on a fast-temporal time scale. The use of an opsin such as C1V1 can be particularly useful based on characteristics regarding an accelerated photocycle. Moreover, certain embodiments allow for reversible disease states, which can be particularly useful for establishing baseline/control points for testing and/or for testing the effects of a treatment on the same animal when exhibiting the disease state and when not exhibiting the disease state. The use of opsins such as C1V1 allows for the control of a cell using a light source. The C1V1 reacts to light, causing a change in the membrane potential of the cell. The removal of the light and the subsequent cessation of the activation of C1V1 allows for the cell to return to its baseline state. Various other possibilities exist, some of which are discussed in more detail herein.

Various aspects of the present disclosure are directed to an E122T mutation of a C1V1 opsin. In certain embodiments of the present disclosure, the E122T mutation shifts maximum absorption of C1V1 or its variants toward the red light spectrum with respect to the un-mutated opsin.

Various embodiments of the present disclosure relate to an opsin modified for expression in mammalian cells and shifted, with respect to ChR2, for maximum absorption in the green light spectrum. The C1V1 opsin is derived from a combination of opsins and expresses at a higher rate than either of the opsins from which it is derived. The opsin, C1V1, is derived from *Volvox* channelrhodopsin (VChR1) and *Chlamydomonas reinhardtii* channelrhodopsin (ChR1). The resulting opsin, C1V1 and its variants, have a maximum absorption at wavelengths between 530 nm and 546 nm.

Certain aspects of the present disclosure are directed to further modified versions of C1V1. For example, certain embodiments include a mutation E122T, which shifts the maximum absorption of C1V1 towards the red light spectrum. Other modifications can include an additional mutation E162T, which experiments suggest provides an accelerated photocycle in addition to the red shift provided by the E122T mutation.

In some embodiments, there is provided a transmembrane molecule derived from VChR1 and having the traffic sequences replaced with homologous sequences from ChR1. In some embodiments, the molecule further includes a mutation E122T. In other embodiments, the molecule further includes mutations at E162T and E122T. In certain embodiments, the molecule activates an ion channel in response to green light. In one embodiment, the molecule has a maximum light absorption of approximately 546 nm. In another embodiment, the molecule has a maximum light absorption of approximately 535 nm.

In some embodiments, there is provided an animal cell comprising: an integrated exogenous molecule which expresses an ion channel that is responsive to red light; the exogenous molecule derived from VChR1 and including transmembrane traffic sequences thereof replaced by homologous sequences from ChR1. In some embodiments, the exogenous molecule further includes E122T. In other embodiments, the cell has a neural firing ratio of about 14% to 94% in response to light having wavelengths of 405 nm and 560 nm, respectively. In other embodiments, the cell has a neural firing ratio of about 11% to 72% in response to light having wavelengths of 405 nm and 560 nm, respectively.

Additional example embodiments of the present disclosure relate to the use of a hybrid ChR1/VChR1 chimera that contains no ChR2 sequence at all, is derived from two opsins genes that do not express well individually, and is herein referred to as C1V1. Embodiments of the present disclosure also relate to improvements of the membrane targeting of VChR1 through the addition of a membrane trafficking signal derived from the $K_{ir}2.1$ channel. Confocal images from cultured neurons expressing VChR1-EYFP revealed a large proportion of intracellular protein compared with ChR2; therefore, membrane trafficking signal (ts) derived from the $K_{ir}2.1$ channel was used to improve the membrane targeting of VChR1. Membrane targeting of this VChR1-ts-EYFP was slightly enhanced compared with VChR1-EYFP; however, mean photocurrents recorded from cultured hippocampal neurons expressing VChR1-ts-EYFP were only slightly larger than those of VChR1-EYFP. Accordingly, embodiments of the present disclosure relate to VChR1, which has been modified by exchanging helices with corresponding helices from other ChRs. For example, robust improvement has been discovered in two chimeras where helices 1 and 2 were replaced with the homologous segments from ChR1. It was discovered that whether splice sites were in the intracellular loop between helices 2 and 3 (at ChR1 residue Ala145) or within helix 3 (at ChR1 residue Trp163), the resulting chimeras were both robustly expressed and showed similarly enhanced photocurrent and spectral properties. This result was unexpected as ChR1 is only weakly expressed and poorly integrated into membranes of most mammalian host cells.

Specific aspects of the present disclosure relate to microbial opsin genes adapted for neuroscience, allowing transduction of light pulse trains into millisecond-timescale membrane potential changes in specific cell types within the intact mammalian brain (e.g., channelrhodopsin (ChR2), *Volvox* channelrhodopsin (VChR1) and halorhodopsin (NpHR)). ChR2 is a rhodopsin derived from the unicellular green algae *Chlamydomonas reinhardtii*. The term "rhodopsin" as used herein is a protein that comprises at least two building blocks, an opsin protein, and a covalently bound cofactor, usually retinal (retinaldehyde). The rhodopsin ChR2 is derived from the opsin Channelopsin-2 (Chop2), originally named Chlamyopsin-4 (Cop4) in the *Chlamydomonas* genome. The temporal properties of one depolarizing channelrhodopsin, ChR2, include fast kinetics of activation and deactivation, affording generation of precisely timed action potential trains. For applications seeking long timescale activation, it has been discovered that the normally fast off-kinetics of the channelrhodopsins can be slowed. For example, certain implementations of channelrhodopsins apply 1 $mW/mm^2$ light for virtually the entire time in which depolarization is desired, which can be less than desirable.

Much of the discussion herein is directed to ChR2. Unless otherwise stated, the disclosure includes a number of similar variants. Examples include, but are not limited to, Chop2, ChR2-310, Chop2-310, and *Volvox* channelrhodopsin (VChR1). For further details on VChR1, reference can be made to "Red-shifted optogenetic excitation: a tool for fast neural control derived from *Volvox carteri*," Nat Neurosci. June 2008, 11(6):631-3. Epub 2008 Apr. 23, the disclosure of which is fully incorporated herein by reference in its entirety. In other implementations, similar modifications can be made to other opsin molecules. For instance, modifications/mutations can be made to ChR2 or VChR1 variants. Moreover the modified variants can be used in combination with light-activated ion pumps.

Embodiments of the present disclosure include relatively minor amino acid variants of the naturally occurring sequences. In one instance, the variants are greater than about 75% homologous to the protein sequence of the naturally occurring sequences. In other variants, the homology is greater than about 80%. Yet other variants have homology greater than about 85%, greater than 90%, or even as high as about 93% to about 95% or about 98%. Homology in this context means sequence similarity or identity, with identity being preferred. This homology can be determined using standard techniques known in sequence analysis. The compositions of embodiments of the present disclosure include the protein and nucleic acid sequences provided herein, including variants which are more than about 50% homologous to the provided sequence, more than about 55% homologous to the provided sequence, more than about 60% homologous to the provided sequence, more than about 65% homologous to the provided sequence, more than about 70% homologous to the provided sequence, more than about 75% homologous to the provided sequence, more than about 80% homologous to the provided sequence, more than about 85% homologous to the provided sequence, more than about 90% homologous to the provided sequence, or more than about 95% homologous to the provided sequence.

As used herein, "stimulation of a target cell" is generally used to describe modification of the properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses (action potentials) by the neuron.

For further details on light-activated opsins, reference can be made to PCT publication No. WO 2010/056970, entitled "Optically-Based Stimulation of Target Cells and Modifications Thereto," to Deisseroth et al., which is fully incorporated herein by reference in its entirety.

EXAMPLES

Example 1: Development of Chimeric Channelrhodopsin Variant C1V1

In this example, a tool that would permit the driving of cortical E/I elevations and the monitoring of gamma oscillations in cortical slices, as well as in vivo in live animal experiments, was sought, with three key properties: 1) much higher potency to enable dose-response investigation; 2) low desensitization to allow for step-like changes in E/I balance; and 3) redshifted excitation to allow comparative drive of different populations within the same preparation.

Figure 2:
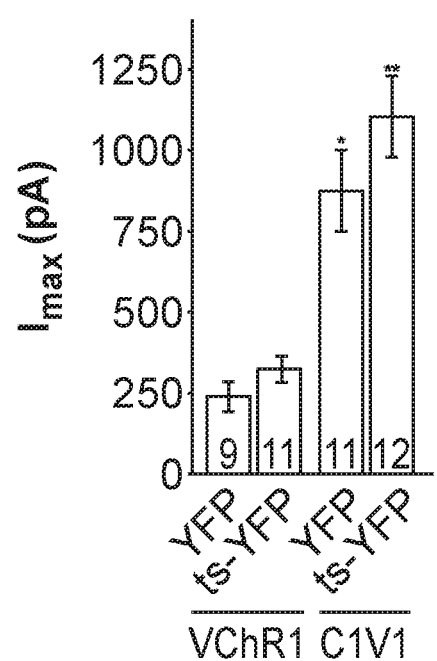

These experiments were initially attempted with VChR1, which displays both a redshift and reduced desensitization[14], but previous investigation suggested that photocurrents in cells expressing VChR1 were small (~100-150 pA[14]), and did not elicit robust synaptic activity in downstream cells (not shown). Indeed, when first attempting to express VChR1 in cells, only small photocurrents were observed, (FIG. 1) consistent with previous findings. Adding a membrane trafficking signal derived from the Kir2.1 channel to generate VChR1-is-EYFP delivered only a modest trend toward enhanced photocurrents compared with VChR1-EYFP (FIG. 2). However, noting that in ChR2, replacing transmembrane segments with the homologous region from ChR1 increased membrane targeting and enhanced photocurrents, it was hypothesized that a similar systematic exchange between the helices of VChR1 with the corresponding helices from other ChRs, might similarly result in enhanced membrane expression in HEK cells.

Materials and Methods

Chimeric channelrhodopsin variant C1V1 was generated by fusing either a wild-type or human codon-optimized channelrhodopsin-1 with a human codon-adapted VChR1 (GenBank™ accession number ACD70142.1) by overlap extension PCR. C1V1 splice variants were generated by overlap PCR. Variant one contained the first 145 amino acids of ChR1 and amino acids 102 to 316 of VChR1. Variant two contained the first 162 amino acids of ChR1 and amino acids 119 to 316 of VChR1. The resultant chimeric PCR fragments were cloned into pECFP-N1 (Clonetech, Mountain View, Calif.) and into lentiviral expression vectors under the CaMKIIa promoter. The membrane trafficking signal was derived from the Kir2.1 channel. Mutations were confirmed by sequencing the coding sequence and splice sites. For AAV-mediated gene delivery, opsin-EYFP fusions along with the CaMKIIa promoter were subcloned into a modified version of the pAAV2-MCS vector. Cre-dependent opsin expression was achieved by cloning the opsin-EYFP cassette in the reverse orientation between pairs of incompatible lox sites (loxP and lox2722) to generate a double floxed inverted open reading frame (D10) under the control of the elongation factor 1a (EF-1α) promoter. All constructs are available from the Deisseroth Lab (www(dot)optogenetics (dot)org).

HEK293 cells were cultured in Dulbecco's minimal essential medium supplemented with 10% fetal bovine serum, 2 mM glutamine (Biochrome, Berlin, Germany), and 1% (w/w) penicillin/streptomycin. Cells were seeded onto coverslips at a concentration of 0.175×106 cells/ml and supplemented with 1 μM all-trans retinal. Transient transfection was performed with Fugene 6 (Roche, Mannheim, Germany) and recordings were done 20-28 hours later. Photocurrents in transiently transfected HEK293 cells were recorded by conventional whole-cell patch-clamp. The external solution contained [mM]: 140 NaCl, 2 CaCl$_2$, 2 MgCl$_2$, 2 KCl, 10 HEPES (pH 7.2). The internal solution contained [mM]: 110 NaCl, 10 EGTA, 2 MgCl$_2$, 1 CaCl$_2$, 5 KCl, 10 HEPES (pH was adjusted to 7.2 either using CsOH or HCl). Patch pipettes were pulled with micropipette puller model P-97 (Sutter Instrument Co., Novato, Calif.) from microhaematocrit-tubes (Hecht-Assistant, Sondheim, Germany) with 1.5-2 MΩ resistance. HEK cell whole-cell patch-clamping was performed with an EPC 7 (HEKA, Elektronik GmbH, Lambrecht, Germany) amplifier. Analog data was sampled at 20 kHz, digitized with Digidata1440 (Molecular Devices, Foster City, Calif.) and displayed using pClamp10.1 Software (Molecular Devices, Foster City, Calif.). For recording wavelength dependence, a light guide from a Polychrome V unit (TILL Photonics, Planegg, Germany) was mounted on the epiluminescence port of an Olympus IX70 microscope. For reflecting light into the objective a beam splitter (70% R/30% T) was used resulting in a final photon density of ~1×10$_{22}$ photons m$^{-2}$ s$^{-1}$ at 470 nm on the coverslip. For recording the action spectra only 50% of the light intensity was used. The polychrome V Unit was controlled with Tillvision Software (TILL Photonics, Planegg, Germany) synchronized with the pClamp Software.

Results

Figure 4:
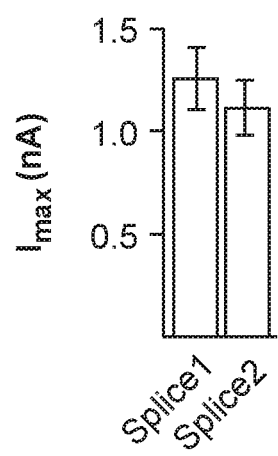
Figure 5:
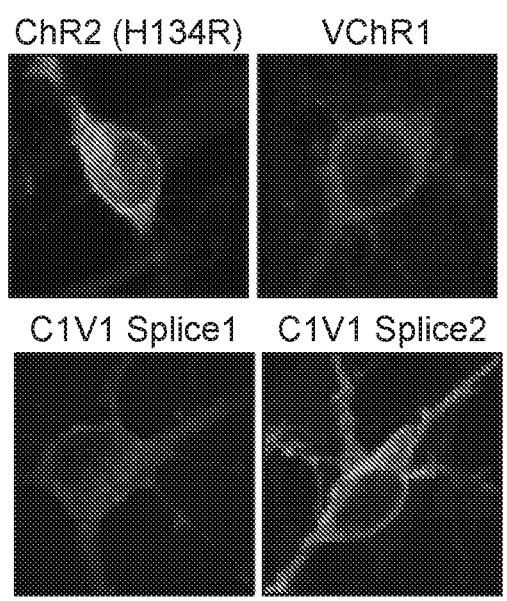
Figure 6:
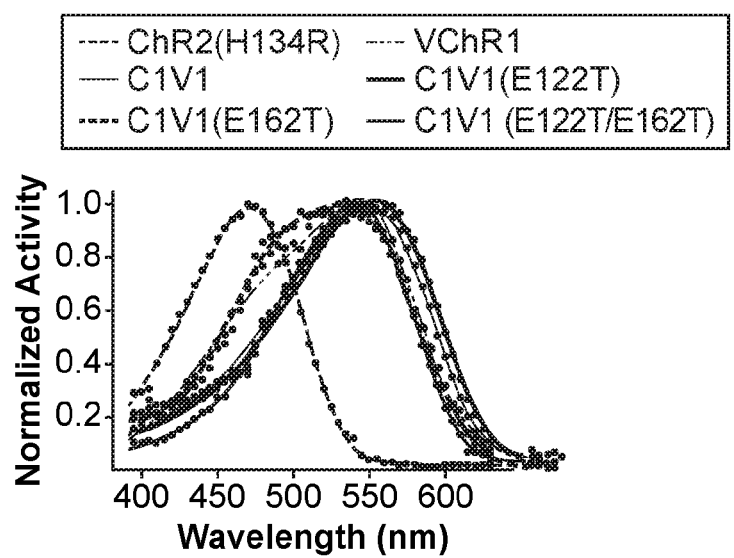
Figure 7:
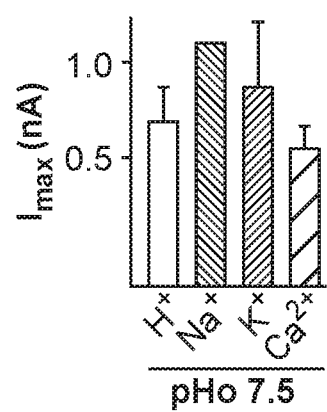
Figure 8:
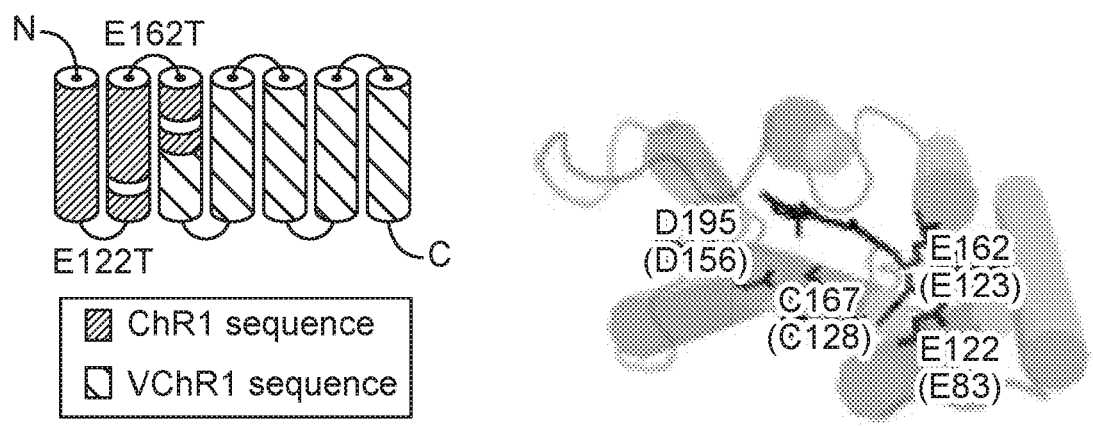

Interestingly, the most robust improvement in chimeras was found where helix 1 and 2 were replaced with the homologs from ChR1 (FIG. 4). Two chimeric ChR1-VChR1 channels for membrane targeting and photocurrent size were tested in cultured HEK293 cells. The first was joined in the second intracellular loop after Ala145 of ChR1, and the second was joined within helix three after Trp163 of ChR1 (FIG. 3). Whereas both variants were nearly equally well expressed in HEK293 cells (FIG. 4), in cultured neurons the second variant expressed more robustly (FIG. 5) and showed greatly enhanced peak photocurrents (888±128 pA, n=11 cells; p<0.0005) compared with VChR1-EYFP (FIG. 2). The action spectrum peak remained robustly redshifted relative to ChR2 (Table 1; FIG. 6), and the ionic selectivity of the chimera was similar to that previously reported for ChR2 and VChR1 (FIG. 7) Adding the Kir2.1 trafficking sequence to this hybrid trended to further increased photocurrents (1104±123 pA, n=12 cells; p<0.0005 compared with VChR1-EYFP, p=0.23 compared with C1V1-EYFP; FIG. 2; Tables 1-2). The resulting hybrid ChR1/VChR1 chimera contains no ChR2 sequence at all, is remarkably derived from two opsin genes that do not express well alone, and is here referred to as C1V1 (FIG. 1, FIG. 8).

Example 2: Optimization of Photocurrent Kinetics of C1V1

Fast deactivation properties[28] of this redshifted opsin would be required for maximal temporal as well as spectral separation from other opsins that are activated by wavelengths located towards the blue end of the visible spectrum. However, it was found that the photocurrents displayed by C1V1-ts-EYFP exhibited >10-fold slower decay than ChR2, and even slower decay than the original VChR1 (FIG. 9; To$_{ff}$ 156±12 ms and 132±12 ms for C1V1-ts-EYFP (n=4) and VChR1-EYFP (n=5), respectively; Table 1), potentially precluding the use of C1V1 for applications requiring rapid firing rates. To correct the photocurrent kinetics of C1V1, the chromophore region was searched using known structural models[22,28] (FIG. 8) for mutations with faster photocycle kinetics, reduced inactivation and reduced blue absorption. Next, glutamate-122 was mutated to threonine, based on studies of the glutamate-rich motif in helix 2 showing that this mutation reduces inactivation.[3]

Materials and Methods

All point mutations in C1V1 vectors were generated in the plasmids by site-directed mutagenesis (Agilent Technologies, Palo Alto, Calif.). The membrane trafficking signal was derived from the $K_{ir}2.1$ channel. Mutations were confirmed by sequencing the coding sequence and splice sites.

Results

Figure 9:
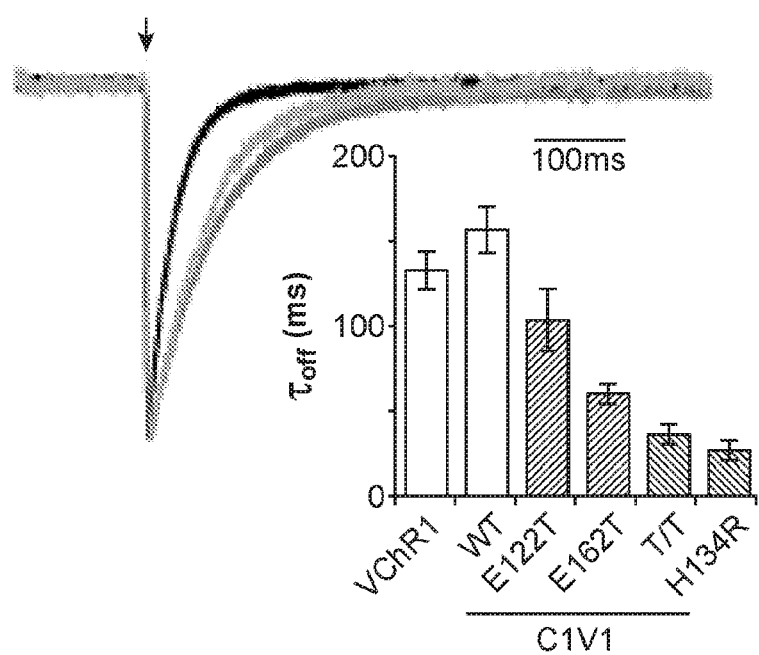
FIG. 9-12 depict testing an improved red-shifted channelrhodopsin for combinatorial optogenetics.
Figure 10:
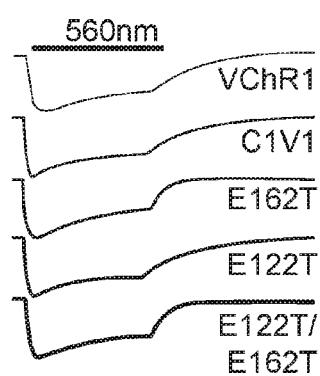
Figure 11:
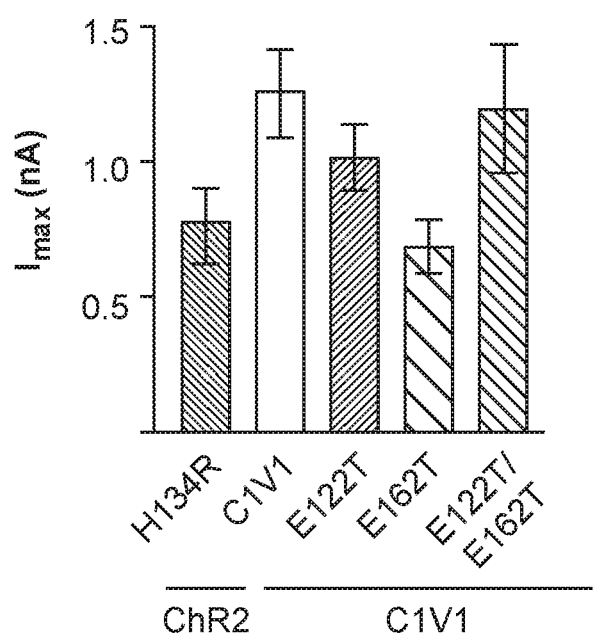
Figure 12:
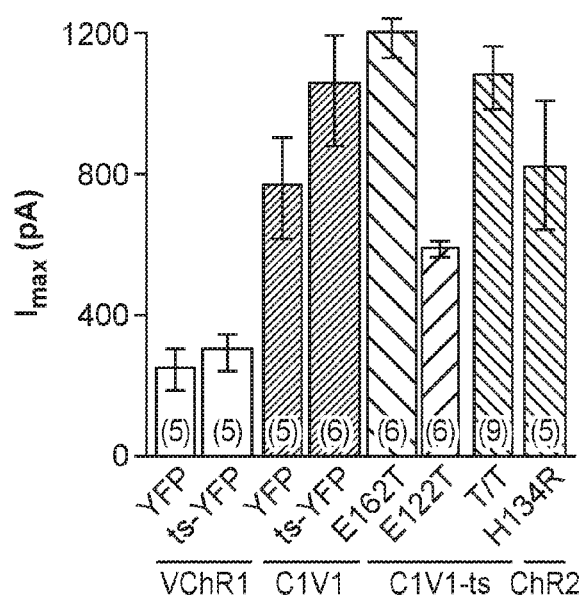

The ChETA-homologous mutation E162T[28] markedly accelerated the photocycle almost 3-fold $To_{ff}$ 58±4.7 ms, n=7 cells; FIG. 9, Table 1). Surprisingly, whereas analogous mutations in ChR2 or other microbial opsins have caused a red-shift[28,29], in C1V1 this mutation shifted the action spectrum in the undesired direction, hypsochromic to 530 nm (FIG. 6; Table 1). C1V1-E122T inactivated only by 26% compared to 46% deactivation of ChR2 (FIG. 10, Table 1); in addition, the spectrum was further red-shifted to 546 nm (FIG. 6, Table 1) and showed a striking loss of the problematic blue shoulder of the C1V1 action spectrum. Finally, in the double mutant E122T/E162T, inactivation of the current was even lower than in the E122T mutant and the photocycle was still faster compared to E162T $To_{ff}$ 34±4.9 ms, n=7 cells; FIG. 9, FIG. 11, Table 1), while preserving the redshift and absence of the blue shoulder of the action spectrum. Moreover, while the E122 mutant severely reduced photocurrent amplitude (FIG. 12, the double mutant restored the very high currents characteristic of the original C1V1-ts. Thus, multiple surprising and useful properties of the individual mutations were conserved in the double mutant, trafficking-enhanced C1V1 chimera.

TABLE 1

Spectral/kinetic properties of ChR2, VChR1 and C1V1 variants.
Peak activation wavelength was recorded in HEK cells using 2 ms light pulses at the peak activation wavelength. Deactivation kinetics ($\tau_{off}$) and peak photocurrents were recorded in cultured hippocampal neurons using 2 ms light pulses at the maximal activation wavelength. To identify the optimal variants for combinatorial activation with ChR2, the percent response at 405 nm and 560 nm was recorded in HEK cells. Desensitization of the photocurrent was recorded using 300 ms light pulses, quantifying the decay of the peak photocurrent ($I_{max}$) to the steady state.

|  | Absorption maximum (nm) | Toff Kinetics pH 7.2 (ms) | Peak current (pA) at −60 Mv* | Ratio 405/560 | Desensitation % |
|---|---|---|---|---|---|
| ChR2 | 460 ± 6 (N = 5) | 10 ± 1 (N = 5) | 816 ± 181 (N = 5) | 60%:8% (N = 7) | 65 ± 8 (N = 5) |
| VChR1 | 543 ± 7 (N = 7) | 85 ± 11 (N =6) | 284 ± 54 (N = 5) | 9%:82% (N = 7) | 53 ± 10 (N = 18) |
| C1V1 | 539 ± 4 (N = 10) | 60 ± 6 (N = 6) | 1035 ± 158 (N = 6) | 28%:86% (N = 10) | 46 ± 12 (N = 14) |
| C1V1(E162T) | 530 ± 4 (N = 6) | 23 ± 5 (N = 4) | 1183 ± 53 (N = 6) | 20%:71% (N = 6) | 41 ± 12 (N = 7) |
| C1V1(E122T) | 546 ± 5 (N = 4) | 55 ± 8 (N = 5) | 572 ± 21 (N = 5) | 14%:94% (N = 4) | 26 ± 6 (N 4) |
| C1V1(E122T, E162T) | 535 ± 5 (N = 7) | 12 ± 1 (N = 5) | 1072 ± 89 (N = 9) | 11%:72% (N = 7) | 11 ± 9 (N = 9) |

TABLE 2

Summary of p-values from unpaired t-test comparisons for peak photocurrent amplitude across all opsins shown in Table 1. Photocurrents were recorded in cultured neurons using a 2 ms light pulse at 540 nm (VChR1 and C1V1 variants) or 470 nm (ChR2(H134R)).

| VchR1-YFP | VChR1-ts-YFP | C1V1-YFP | C1V1-ts-YFP | C1V1 (E162T)-ts-Y | C1V1 (E162T/E122T)-ts-YFP | ChR2(H134R)-YFP | |
|---|---|---|---|---|---|---|---|
| 1.0000 | 0.5770 | 0.0188 | 0.0029 | 6.5E−06 | 1.1E−05 | 0.0448 | VChr1-YFP |
|  | 1.0000 | 0.266 | 0.0039 | 1.1E−06 | 0.0015 | 0.0579 | VChR1-ts-YFP |
|  |  | 1.0000 | 0.3372 | 0.0399 | 0.0788 | 0.8175 | C1V1-YFP |
|  |  |  | 1.0000 | 0.4099 | 0.8442 | 0.4222 | C1V1-ts-YFP |
|  |  |  |  | 1.0000 | 0.3254 | 0.1490 | C1V1(E162T)-ts-Y |
|  |  |  |  |  | 1.0000 | 0.3001 | C1V1(E162T/E122T)-ts-YFP |
|  |  |  |  |  |  | 1.0000 | ChR2(H134R)-YFP |

Thus, multiple useful properties of the individual mutations were conserved together in the double mutant.

Example 3: Use of Novel C1V1 Chimeras in Prefrontal Cortex Neurons

To test these novel C1V1 opsin genes in neurons, lentiviral vectors encoding C1V1-ts-EYFP and the point mutation combinations above were generated. These opsins were then expressed in cultured hippocampal neurons and recorded whole-cell photocurrents under identical stimulation conditions (2 ms pulses, 542 nm light, 5.5 mW mm$^{-2}$) to determine whether the improvement in photocurrent amplitude resulted directly from the increased expression of C1V1 compared to VChR1.

Materials and Methods

Animals

Wild-type or transgenic Parvalbumin::Cre C57/BL6J male mice were group housed three to five to a cage and kept on a reverse 12 hour light/dark cycle with ad libitum food and water. Experimental protocols were approved by Stanford University IACUC and meet guidelines of the National Institutes of Health guide for the Care and Use of Laboratory Animals.

Whole Cell Patch-Clamp Electrophysiology in Hippocampal and Cortical Neurons

Primary hippocampal cultures were isolated from P0 Sprague-Dawley rats, plated on Matrigel (Invitrogen)-coated glass coverslips and treated with FUDR to inhibit glia overgrowth. Endotoxin-free plasmid DNA was transfected in cultured neurons using a HEPES buffered Saline/CaPO4 mix. Electrophysiological recordings from individual neurons identified by fluorescent protein expression were obtained in Tyrode media ([mM] 150 NaCl, 4 KCl, 2 MgCl2, 2 MgCl2, 10 D-glucose, 10 HEPES, pH 7.35 with NaOH) using a standard internal solution ([mM] 130 KGluconate, 10 KCl, 10 HEPES, 10 EGTA, 2 MgCl2, pH 7.3 with KOH) in 3-5 MΩ glass pipettes. For cortical slice physiology, acute 300 gm coronal slices from 8-9 week old wild-type C57BL/6J or PV::Cre mice previously injected with virus were obtained in ice-cold sucrose cutting solution ([mM] 11 D-glucose, 234 sucrose, 2.5 KCl, 1.25 NaH2PO4, 10 MgSO4, 0.5 CaCl2, 26 NaHCO3) using a Vibratome (Leica). Slices were recovered in oxygenated Artificial Cerebrospinal Fluid (ACSF; [mM] 124 NaCl, 3 KCl, 1.3 MgCl2, 2.4 CaCl2, 1.25 NaH2PO4, 26 NaHCO3, 10 D-glucose) at 32° C. for one hour. Individual neuron patches were obtained after identifying fluorescent protein expression from indicated prefrontal cortical layer under constant ACSF perfusion. Filtered light from a broad-wavelength xenon lamp source (Sutter Instruments DG-4) was coupled to the fluorescence port of the microscope (Leica DM-LFSA). Band pass filters (Semrock) had 20 nm bandwidth, and were adjusted with additional neutral density filters (ThorLabs) to equalize light power output across the spectrum.

Cultured cell images were acquired on the same microscope using a Retiga Exi CCD camera (Qimaging, Inc.) at 100 ms exposure with 30 gain. Illumination power density was 12 mW mm$^{-2}$ at 500 nm with a standard EYFP filter set. Quantification of fluorescence was performed with ImageJ software by marking a region containing the soma and proximal neurites and calculating for each cell the total integrated pixel intensity in that region, rather than average fluorescence, since photocurrents are likely to be related to the total number of membrane-bound channels rather than average channel expression per area.

Virus Preparation and Injection

Both Lentiviral- and AAV-mediated gene delivery were used for heterologous expression of opsins in mice. Indicated opsins were driven by either Human calmodulin-dependent protein kinase II alpha (CaMKIIa) promoter to target cortical excitatory neurons or Elongation Factor 1a (EF-1a) in conjunction with a Cre-inducible cassette and followed by the Woodchuck hepatitis virus posttranscriptional regulatory element (WPRE). Cre-inducible recombinant AAV vector was produced by the University of North Carolina Vector Core (Chapel Hill, N.C., USA) and used in conjunction with parvalbumin::Cre transgenic mice to target parvalbumin positive nterneurons. Briefly, AAV constructs were subcloned into a modified version of the pAAV2-MCS, serotyped with AAV5 coat proteins and packaged by the viral vector core at the University of North Carolina. The final viral concentration of AAV vectors as 1×10$^{12}$ genome copies (gc)/mL. Lentiviral constructs were generated as reported. All constructs are available from the Deisseroth Lab (www.optogenetics.org). Stereotactic viral injections were carried out under protocols approved by Stanford University. Juvenile (4-6 weeks) mice kept under isoflurane anesthesia were arranged in a stereotactic frame (Kopf Instruments) and leveled using bregma and lambda skull landmarks. Craniotomies were preformed so as to cause minimal damage to cortical tissue. Infralimbic prefrontal cortex (IL; from bregma: 1.8 mm anterior, 0.35 mm lateral, −2.85 mm ventral) was targeted using a 10 uL syringe and 35 g beveled needle (Word Precision Instruments). Virus was infused at a rate of 0.1 µL/min Subjects injected with virus for behavioral studies were additionally implanted with a chronic fiber optic coupling device to facilitate light delivery either with or without an attached penetrating cerebral fiber for local delivery to target cortical region as noted (Doric Lenses, Canada). Penetrating fibers were stereotactically inserted to a depth of −2.5 mm from the same anterior and lateral coordinates and affixed using adhesive luting cement (C&B MetaBond) prior to adhesive closure of the scalp (Vetbond, 3M). Animals were administered analgesic relief following recovery from surgery.

Results

Figure 13:
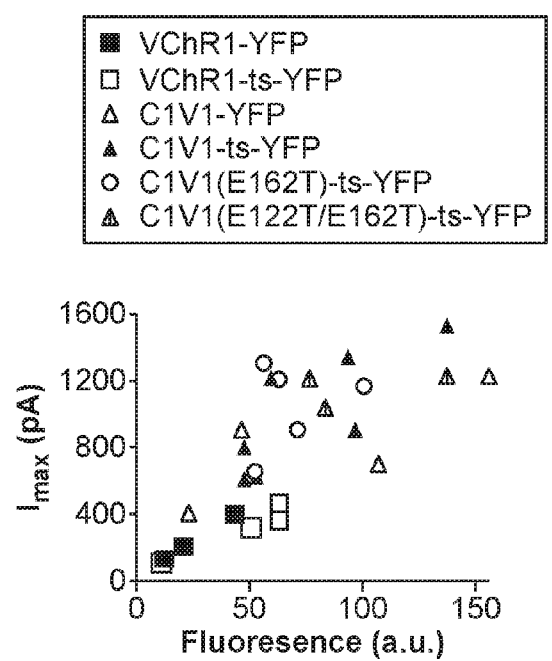
FIG. 13-20 depict photocurrents from acute slice recordings in prefrontal pyramidal neurons.
Figure 14:
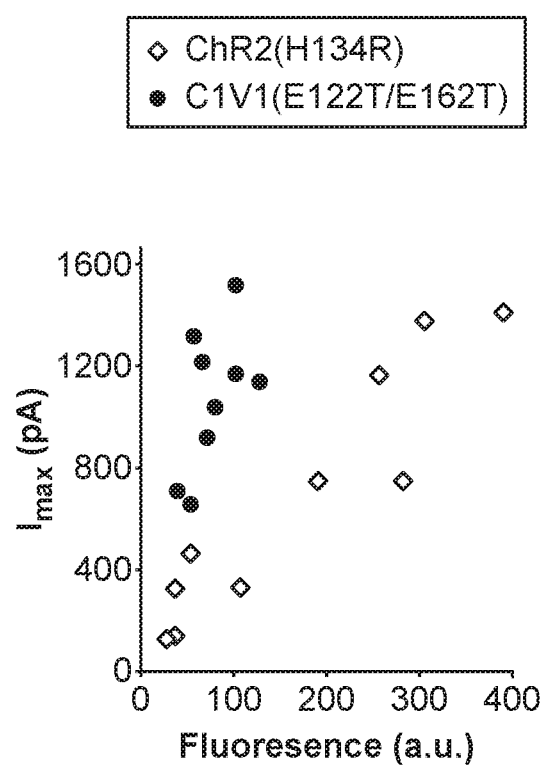

Recordings from cultured hippocampal neurons expressing individual constructs and an integrated fluorescence reading were obtained from each individual cell. In individual cells, fluorescence levels closely correlated with the measured photocurrent amplitudes across constructs (FIG. 13). It was therefore concluded that the potently increased photocurrent of C1V1 resulted chiefly from improved expression in neurons. Since the double mutant C1V1-E122T/E162T showed superior performance along all dimensions tested (photocurrent size, inactivation kinetics, and action spectrum), performance to ChR2(H134R) was also directly compared by measuring integrated somatic YFP fluorescence and peak photocurrents. Surprisingly, C1V1-E122T/E162T cells showed stronger photocurrents than ChR2-H134R cells at equivalent fluorescence levels (FIG. 14), potentially suggestive of increased unitary conductance.

Figure 15:
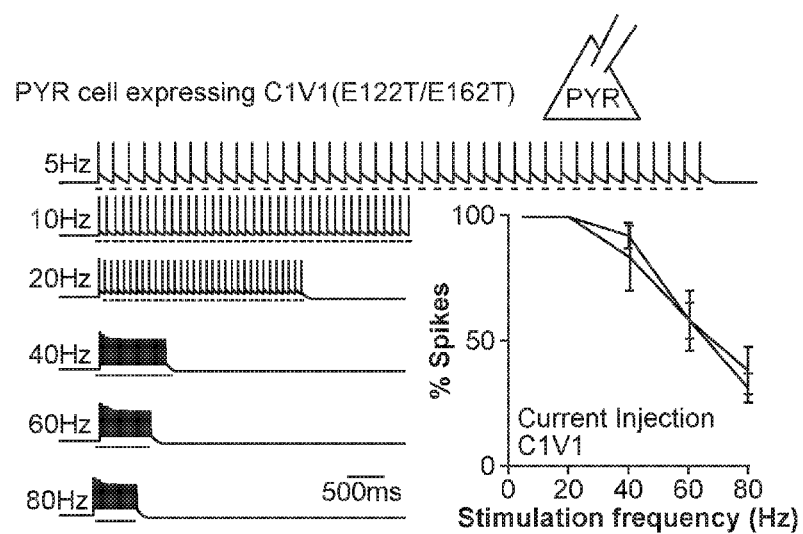
Figure 16:
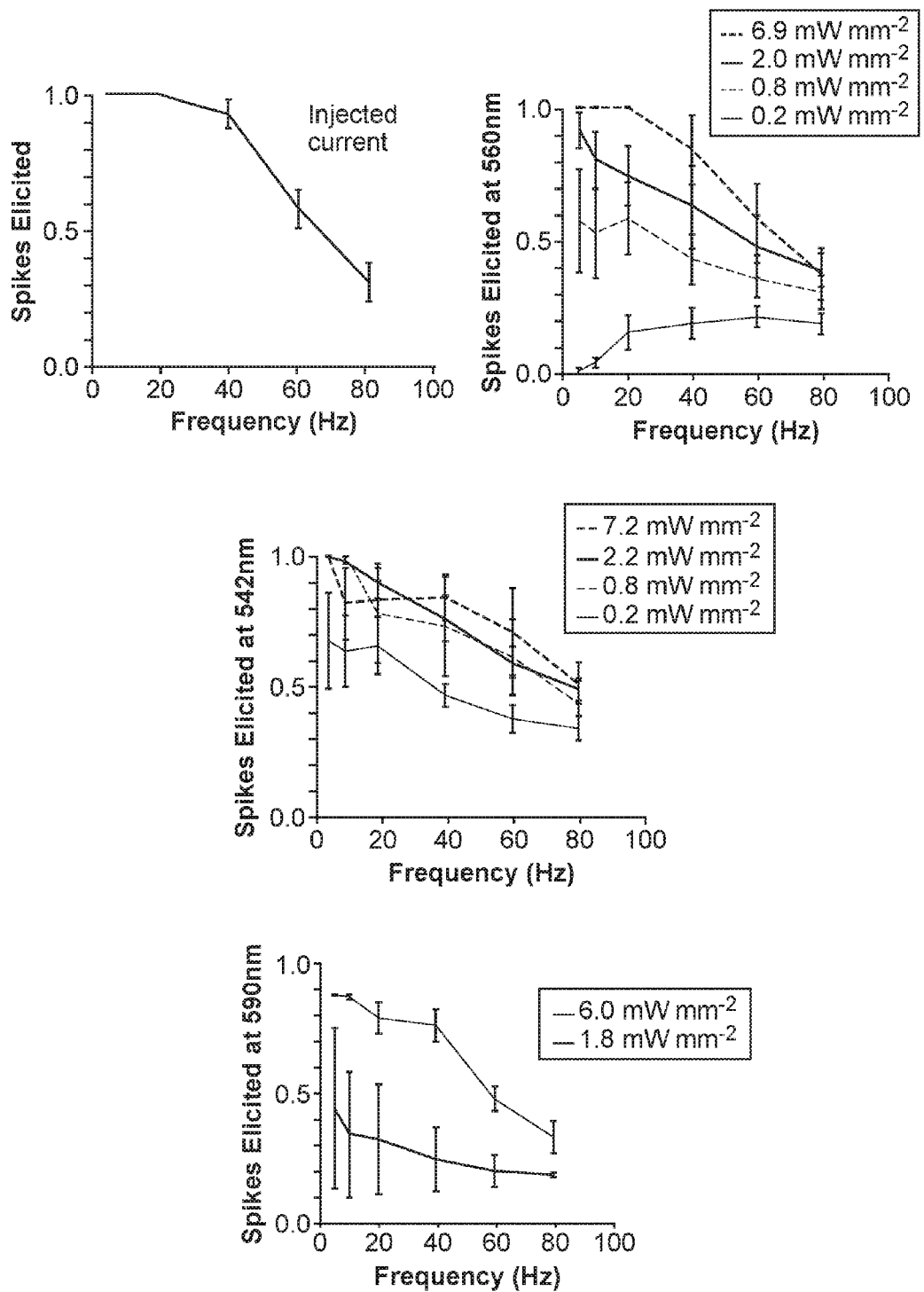

To examine whether C1V1-E122T/E162T would be suitable for optically driving spiking in pyramidal neurons, adeno-associated viral vectors harboring the C1V1-E122T/E162T-ts-EYFP gene under the CaMKIIa promoter (AAV5-CaMKIIa-C1V1-E122T/E162T-ts-EYFP) were generated and injected the virus into the prefrontal cortex of mice. Responses were recorded from expressing neurons in acute slices with 2 ms light pulse trains and compared with responses to trains of current injection (10 ms, 200 pA) at identical frequencies. It was found that the frequency response of neurons to 560 nm pulse trains was indistinguishable from the response to current injections at the same frequencies (FIG. 15; n=6 cells in 2 slices), suggesting that intrinsic properties of the cell and not C1V1 kinetics limit spiking performance at high rates. Similar performance properties were seen across a range of green, yellow, and amber illumination conditions, with strong performance at the moderate light intensities (<10 mW/mm$^2$) suitable for in vivo applications in mammals (FIG. 16). Indeed, responses at 540 nm and 590 nm were similarly effective at evoking precisely timed action potentials, with lower fidelity at lower light powers as expected (FIG. 16).

Figure 17:
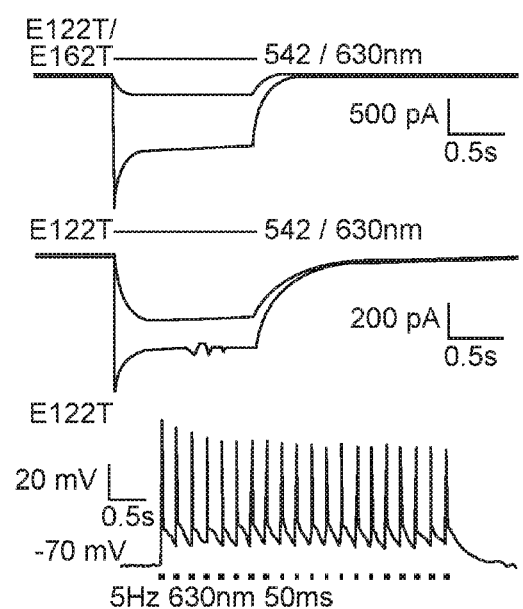
Figure 18:
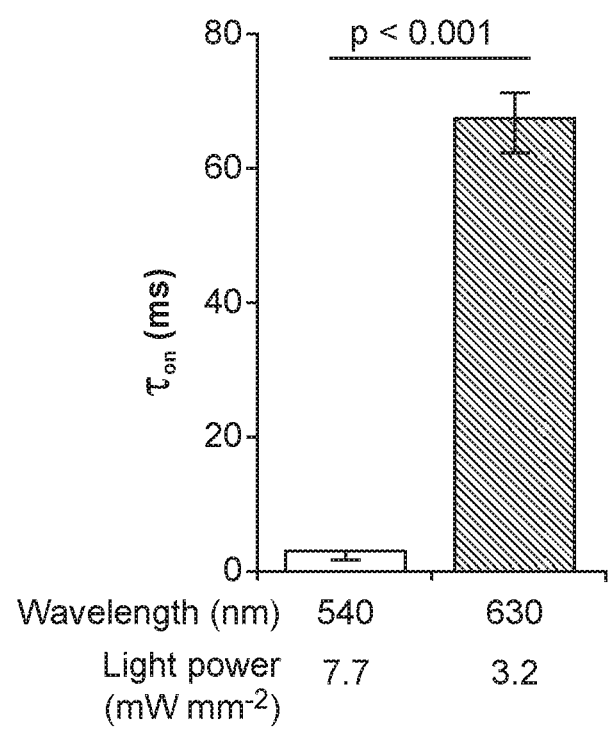
Figure 19:
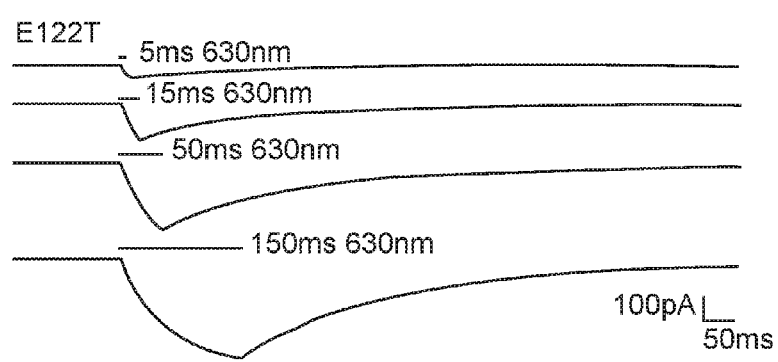
Figure 20:
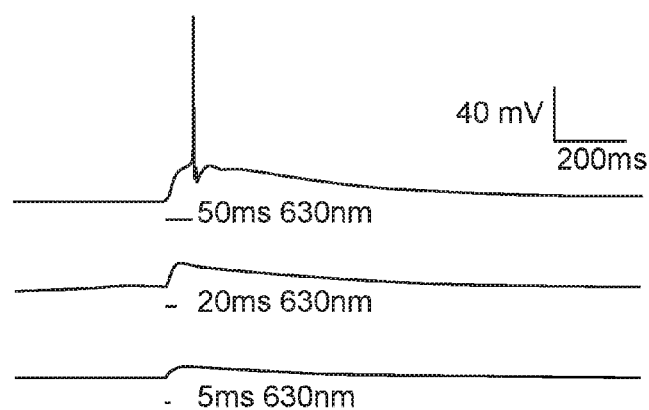

With the prominently red-shifted action spectrum, the possibility that C1V1 might even be used to drive spiking with red light, not previously reported with any opsin and potentially important for allowing improved spectral separation as well as control of neurons in deeper tissue, was considered. Whether any C1V1 variants could be used to drive spikes using far-red light was therefore examined Although the kinetics of C1V1-E122T were slower than those of C1V1-E122T/E162T, its action spectrum was the most red-shifted of all variants (FIG. 6), and indeed it was found that cells expressing C1V1-E122T responded more strongly to red light (630 nm) than cells expressing the double mutant (FIG. 17, top). Although on-kinetics of the E122T mutant at 630 nm were slower than at 545 nm (FIG. 18), photocurrents were recruited using longer pulses of 630 nm light at moderate intensity (FIG. 19) that sufficed to elicit defined spike trains (FIG. 20; FIG. 17, bottom).

Example 4: Use of Novel C1V1 Chimeras in Living Brain Slices from the Prefrontal Cortex Neurons of Mice The study sought to determine whether inhibitory and excitatory neurons residing within the same microcircuit could be targeted with the introduction of C1V1 variants. Independent activation of two neuronal populations within living brain slices was explored; in this case CaMKIIα-C1V1-E122T/E162Tts eYFP and EF1a-DIO-ChR2-H134R-EYFP were expressed in mPFC of PV::Cre mice.

Materials and Methods

Acute 300 μm coronal slices isolated from 8-9 week old wild-type C57BL/6J or PV::Cre mice previously injected with virus were obtained in ice-cold sucrose cutting solution ([mM] 11 D-glucose, 234 sucrose, 2.5 KCl, 1.25 $NaH_2PO_4$, 10 $MgSO_4$, 0.5 $CaCl_2$, 26 $NaHCO_3$) using a Vibratome (Leica). Slices were recovered in oxygenated Artificial Cerebrospinal Fluid (ACSF; [mM] 124 NaCl, 3 KCl, 1.3 $MgCl_2$, 2.4 $CaCl_2$, 1.25 $NaH_2PO_4$, 26 $NaHCO_3$, 10 D-glucose) at 32° C. for one hour. Individual neuron patches were obtained after identifying fluorescent protein expression from indicated prefrontal cortical layer under constant ACSF perfusion. Filtered light from a broad-wavelength xenon lamp source (Sutter Instruments DG-4) was coupled to the fluorescence port of the microscope (Leica DM-LFSA). Slice physiology data were imported into Matlab and analyzed using custom-written software. Power spectra were calculated using the wavelet method as described by Sohal et al.[55] Briefly, for each frequency f, the recorded traces were first filtered with a bandpass filter between f±5 Hz. The filtered traces were then convolved with the wavelet function:

$$W(f,t)=s(t)*g(f,t)$$

$$G(f,t)=e^{(-t^2)(2\sigma^2)}e^{-\pi i f t})^{-1}$$

where * denotes convolution, σ=5/(6f). The squared amplitude of W(f,t) over a 500 msec window was then used to measure the power at various frequencies. All power spectra from slice recordings were normalized to 1/f.

Cultured cell images were acquired on the same microscope using a Retiga Exi CCD camera (Qimaging inc.) at 100 ms exposure with the 30 gain. Illumination power density was 12 mW $mm^{-2}$ at 500 nm with a standard EYFP filter set. Quantification of fluorescence was done with ImageJ software by marking a region containing the soma and proximal neuritis and calculating for each cell the total integrated pixel intensity in that region, rather than average fluorescence, since photocurrents are likely to be related to the total number of membrane-bound channels rather than average channel expression per area.

Using current clamp, a single pyramidal cell was stimulated with a train of simulated EPSC waveforms. Individual sEPSC events had peak current magnitudes of 200 pA and decayed with a time constant of 2 ms. Each experiment was divided into 10 sweeps, each 10 seconds long and separated by 5 seconds to minimize rundown. Each sweep was divided into 500 ms segments. The total number of sEPSCs in each 500 ms segment was randomly chosen from a uniform distribution between 0 and 250. Then, the times of the sEPSCs within the 500 ms segment were randomly selected from a uniform distribution extending across the entire segment, simulating excitatory input from a population of unsynchronized neurons. Empirically, these stimulation parameters reliably drove pyramidal neurons at firing rates from 0-30 Hz. In conditions marked as baseline, a 10 sec pulse of 590 nm light was delivered to completely inactivate the opsin before running the sEPSC protocol. In conditions where the opsin was activated, a 1 sec pulse of 470 nm light preceded the sEPSC protocol.

To understand the net effect of altered E/I balance on information processing, the mutual information between each neuron's input sEPSC rate and output spike rate, which captures relevant changes in the shape of the I-O curve and in the response variability was computed. First, the joint distribution of sEPSC rate and spike rate by binning in time, sEPSC rate, and spike rate were estimated and the building of a joint histogram. Time bins were 125 ms wide, and sEPSC rate was divided into 10 equally spaced bins from 0 to 500 Hz, although the mutual information results were consistent across a wide range of binning parameters. Spike rate was binned using the smallest meaningful bin width given the time bin width (e.g. 8 Hz bin width for 125 ms time bins). From this joint histogram, compute mutual information, as previously described was computed equaling the difference between response entropy and noise entropy.

Response entropy quantifies the total amount of uncertainty in the output spike rate of the neuron. Noise entropy quantifies the uncertainty that remains in the output spike rate given the input rate. Note that the maximum information that neural responses can transmit about the input stimulus is the entropy of the stimulus set. For 10 equally spaced input sEPSC rate bins and a uniform distribution of input rate over these bins, the entropy of the input rate is $\log_2(10)=3.322$ bits.

Mutual information calculated from undersampled probability distributions can be biased upwards. Consequently, all reported values of mutual information, response entropy and noise entropy were corrected for bias due to undersampling. This correction is done by computing values from smaller fractions (from one-half to one-eighth) of the full data and extrapolating to the limit of infinite data. Using 125 ms time windows, the correction factors were always less than 0.07 bits.

Vectors were created and injections were performed as above.

Results

Figure 21:
FIG. 21-27 depict independent activation of excitatory pyramidal neurons and inhibitory parvalbumin-expressing cells.

Using this array of multiply engineered opsin genes, the possibilities for combinatorial control of cells and projections within intact mammalian systems was explored. First, it was asked whether excitatory and inhibitory neurons residing within the same microcircuit could be separably targeted by the respective introduction of C1V1 variants and conventional ChRs into these two cell populations. It was found that cultured hippocampal neurons expressing C1V1-E122T/E162T spiked in response to 2 ms green light pulses (560 nm) but not violet light pulses. In contrast, cells expressing ChR2-H134R spiked in response to 2 ms 405 nm light pulses, but not in response to 2 ms 561 nm light pulses (FIG. 21). This principle was therefore tested within living brain slices; in this case AAV5-CaMKIIa::C1V1-E122T/E162T-ts-mCherry along with AAV5-EF1a-DIO::ChR2-

Figure 22:
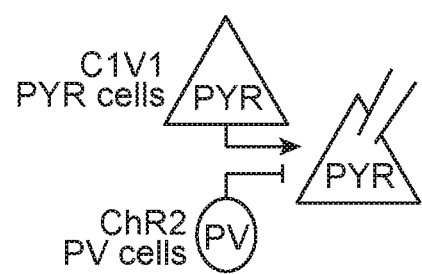
Figure 23:
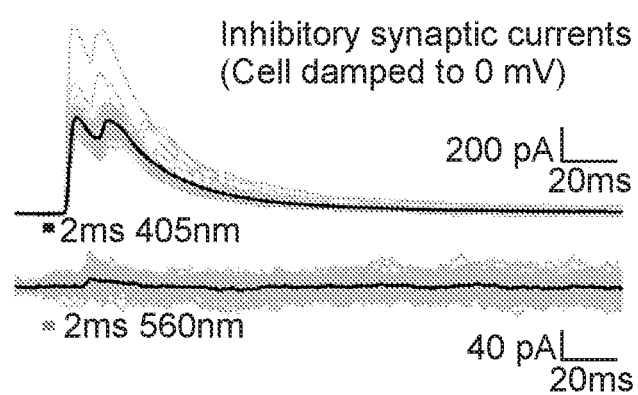
Figure 24:
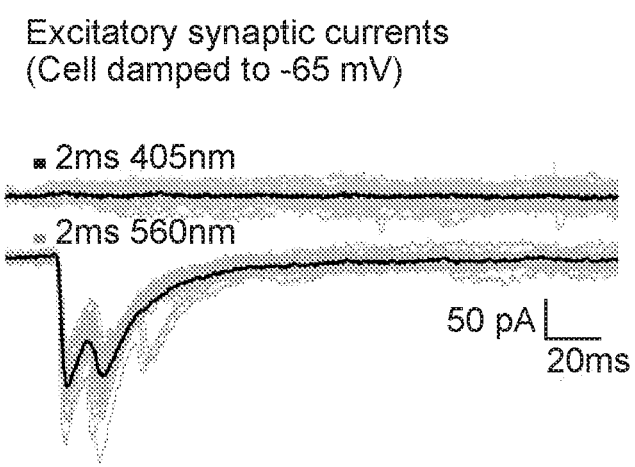

H134R-EYFP in was expressed in mPFC of PV::Cre mice (FIG. 22). In pyramidal neurons not expressing any opsin, 405 nm light pulses triggered robust and fast inhibitory postsynaptic currents due to direct activation of PV cells (FIG. 23), while 561 nm light pulses triggered both short-latency EPSCs (FIG. 24) and the expected long-latency polysynaptic IPSCs arising from C1V1-expressing pyramidal cell drive of local inhibitory neurons (FIG. 23).

Figure 25:
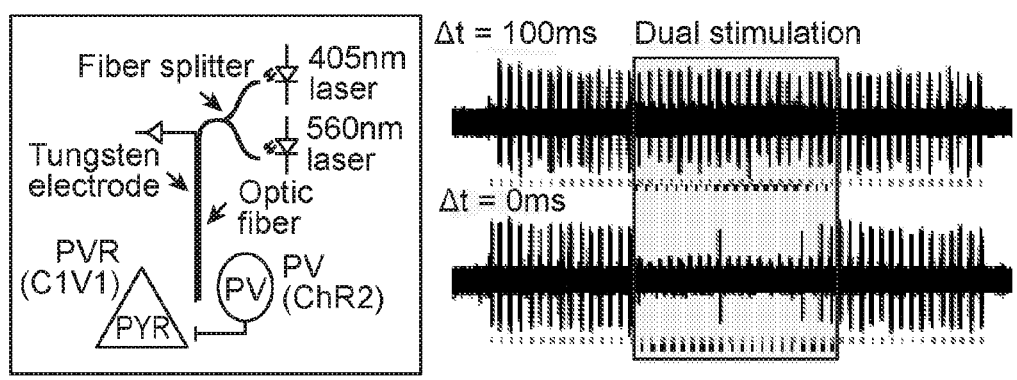
Figure 26:
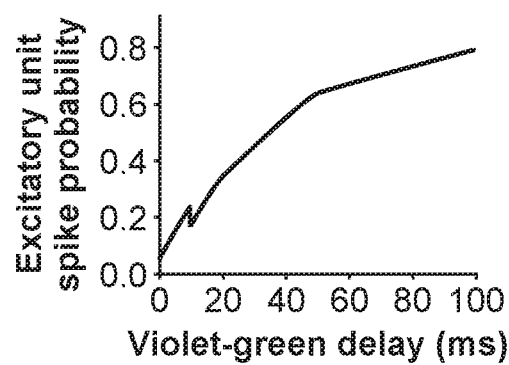
Figure 27:
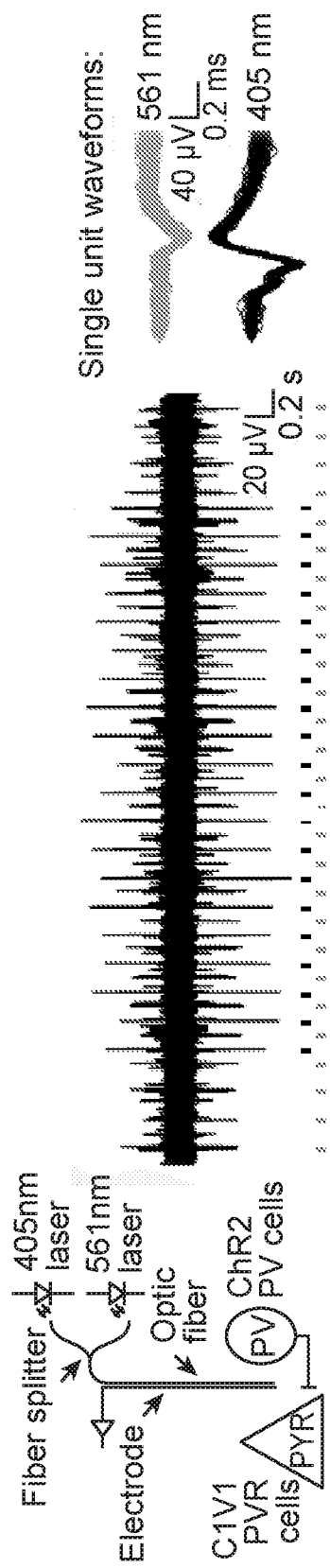

Excitation of these independent cellular elements in vivo with optrode recordings was then explored (FIG. 25, left). To examine the inhibitory effect of PV cell activity on pyramidal neuron spiking, an experimental protocol in which 5 Hz violet light pulses (to activate ChR2 in PV cells) preceded 5 Hz green light pulses (to activate C1V1 in excitatory pyramidal neurons) with varying inter-pulse intervals was designed. When violet and green light pulses were separated by 100 ms (FIG. 25, top trace), responses to green light pulses were not affected by the violet pulses. However, as delays between violet and green pulses were reduced, green light-induced events became more readily inhibited and were completely abolished when light pulses were presented with sufficient synchrony (FIG. 25, bottom trace; summary data in FIG. 26). These data demonstrate combinatorial optogenetic activation within an intact mammal (driving one population alone or in precise temporal combination with another), capitalizing on the speed of the opsins and the properties of the delivered light pulses.

Figure 28:
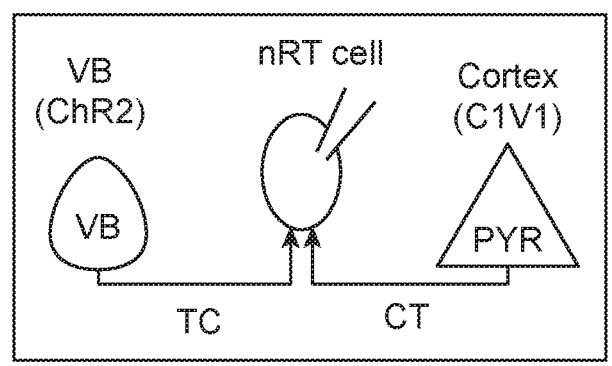
FIG. 28-32 depict combinatorial optogenetic excitation in distinct intact-system preparations.

Example 5: Effect of Independent Activation of Corticothalamic (CT) and Thalamocortical (TC) Glutamatergic Axons Impinging Upon Neurons of the Reticular Thalamic Nucleus To validate the combinatorial control property for axonal projections instead of direct cellular somata stimulation, the effect of independent activation of corticothalamic (CT) and thalamocortical (TC) glutamatergic axons impinging upon neurons of the reticular thalamic nucleus (nRT) (FIG. 28) was examined in thalamic slices.

Materials and Methods

C57BL/6J wild-type (postnatal days 90-120) were anesthetized with pentobarbital (100 mg/kg, i.p.) and decapitated. The thalamic slice preparation and whole-cell patch-clamp recordings were performed. Recordings were obtained from nRT (reticular thalamic) and TC (relay thalamocortical) neurons visually identified using differential contrast optics with a Zeiss (Oberkochen, Germany), Axioskop microscope, and an infrared video camera. For EPSCs and current-clamp recordings, the internal solution contained (in mM): 120 K-gluconate, 11 KCl, 1 $MgCl_2$, 1 $CaCl_2$, 10 Hepes, 1 EGTA. pH was adjusted to 7.4 with KOH (290 mOsm). $E_{Cl^-}$ was estimated ~−60 mV based on the Nernst equation. Potentials were corrected for −15 mV liquid junction potential. For voltage-clamp experiments neurons were clamped at −80 mV and EPSCs were pharmacologically isolated by bath application of the GABAA receptor antagonist picrotoxin (50 μM, Tocris). In all recording conditions, access resistance was monitored and cells were included for analysis only if the access resistance was <18 MΩ and the change of resistance was <25% over the course of the experiment.

600 nL rAAV5/CamKIIα-hChR2(H134R)-EYFP or 900 nL rAAV5-CaMKIIαC1V1(E122T/E162T)-TS-mCherry virus was injected stereotaxically into ventrobasal thalamus (VB) or barrel cortex, respectively, of C57BL/6J wild-type mice in vivo, between post-natal days 30-35. Intra-cortical and intra-thalamic (VB) injections were performed in the same mice (n=6). Intra-cortical injections were preformed (from bregma) 1.3 mm posterior, 3 mm lateral, 1.15 mm below the cortical surface. Intra-thalamic injections were 1.7 mm posterior, 1.5 mm lateral, 3.5 mm below the cortical surface. Mice were sacrificed ~2-3 months following injections and horizontal brain thalamic slices were made for optical stimulation and in vitro recordings as described above. VB thalamus was removed to avoid disynaptic activation of nRT neurons via the CT-TC-nRT pathway. Cutting VB thalamus from slices removed all photosensitive cell bodies from the preparation, enabled direct examination of CTnRT and TC-nRT projections, and did not affect the electrical membrane properties of nRT neurons (not shown). Optical activation of ChR2-expressing TC and C1V1-expressing CT axons were performed with 405 nm and 560 nm laser stimuli, respectively (5 ms duration light pulses, 2-3 mW) (OEM Laser Systems, MI) delivered with optic fiber (BFL 37-300, ThorLabs) upstream along the CT and TC pathways projecting to nRT. Minimal stimulation intensity was used, defined as the light power that resulted in 50 to 70% failures (30-50% successes), fixed response kinetics and low response amplitude variability. Consequent minimal evoked EPSCs presumably resulted from selective optical activation of single CT or TC axons presynaptic to the recorded cell. The stimulation light power was slightly increased (~5% above minimal stimulation) until the number of failures became 0. CT and TC inputs were (simultaneously) stimulated and minimal evoked EPSCs and EPSPs (each individually subthreshold for action potential firing) were recorded in nRT cells.

Figure 30:
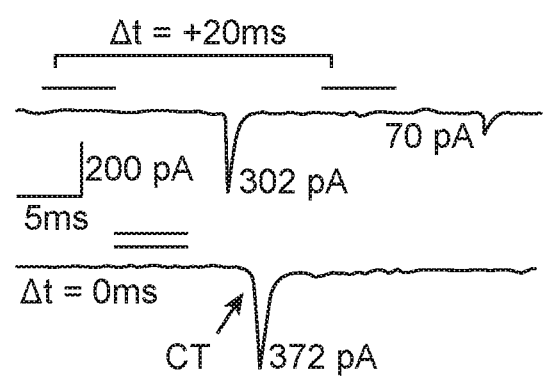

Statistical significance was calculated using paired or unpaired two-tailed t-tests, as applicable. Data were analyzed using Matlab Statistics toolbox or Microsoft Excel Results Minimal stimulation of TC axons evoked large and fast excitatory post-synaptic currents (EPSCs) in nRT neurons, whereas minimal stimulation of CT axons evoked small and slow EPSCs in nRT neurons (FIG. 30), both typical for these pathways.

Figure 29:
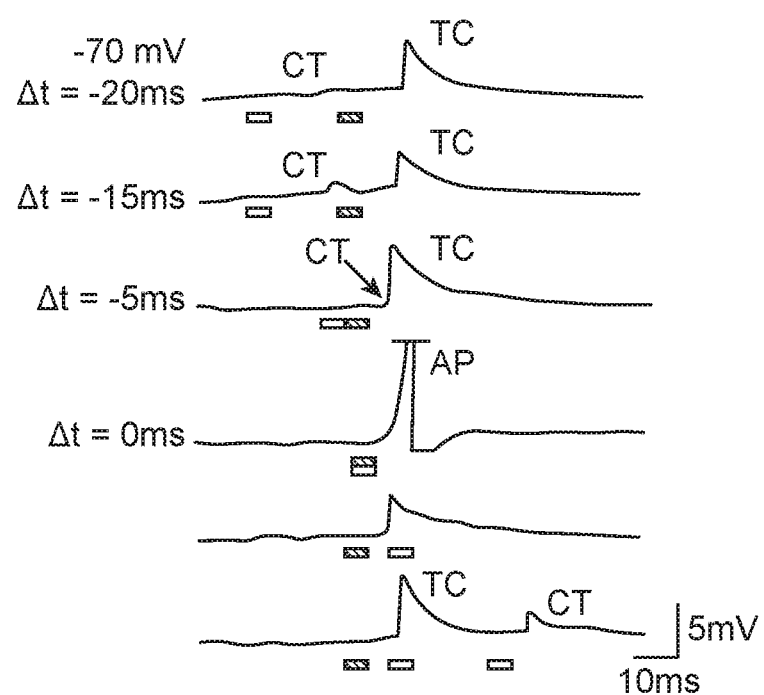
Figure 31:
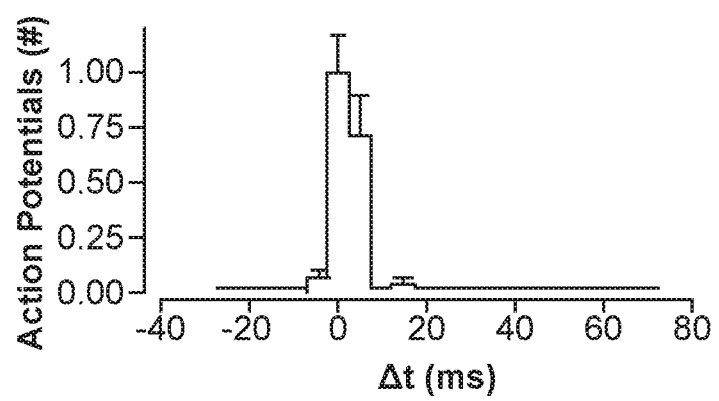
Figure 32:
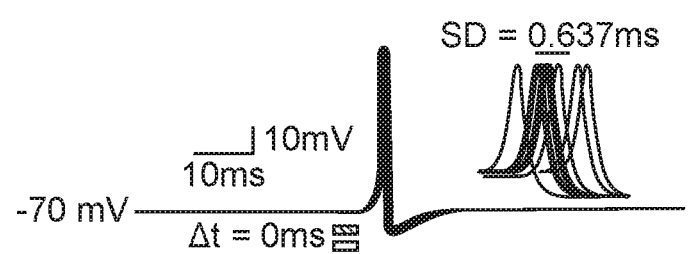

Next the synaptic integration of CT and TC inputs under variable delay conditions between these two inputs was examined. Subthreshold EPSPs from each pathway became suprathreshold for action potential firing only when coincident within 5 ms (FIG. 29, FIG. 31). The temporal precision of C1V1 and ChR2 activation allowed a reliable control of the delay between the TC and CT inputs and thus allowed determination of a narrow window (−5 ms) of effective synaptic integration in nRT cells, not previously observable with existing electrical, pharmacological, or optogenetic techniques due to the reciprocal connectivity of cortex and thalamus as well as the close approximation of CT and TC axons. These results demonstrate for the first time, in the same intact preparation, independent activation of distinct axonal projections to examine their combinatorial effects on the same target cell.

Figure 33:
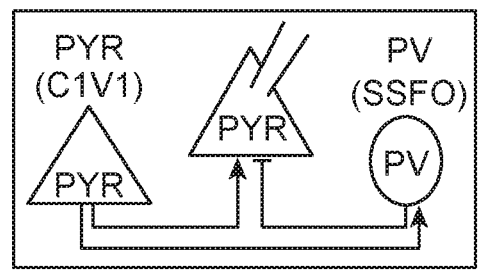
FIG. 33-36 depict spectrotemporal separation and combinatorial control: circuit modulation and emergent patterns in altered E/I states under ongoing synaptic activity.

Example 6: Use of C1V1 and SSFO to Achieve Spectrotemporal Separation of Neural Activation within the Same Circuit In both of the above two preparations, visible-spectrum violet (405 nm) and green (560 nm) lasers were used to achieve separable activation of the two opsins. While 405 nm lasers deliver safe non-UV light, for many applications it may be preferable to use 470 nm laser light for the blue-responsive opsin, since 470 nm light will penetrate tissue more deeply, scatter less, and be more easily and economically delivered from common blue light sources. While this may seem impossible since 470 nm light will partially activate C1V1 (FIG. 7) as well as ChR2, combinatorial control could be achievable even with 470 nm light, capitalizing on both the temporal properties of SSFO and the redshifted nature of C1V1 to achieve "spectrotemporal separation" within intact mammalian tissue. To test this possibility, it was decided to directly compare, within the same preparation, the effects on rhythmic activity of stably potentiating either excitatory or inhibitory cells (FIG. 33)

Materials and Methods

ChR2-D156A and SSFO were generated by inserting point mutations into the pLenti-CaMKIIα-ChR2-EYFP-WPRE vector using site-directed mutagenesis (Quikchange II XL; Stratagene). Viral gene delivery, coronal brain sectioning, and patch clamp recording were performed as above. Double virus injections to express CaMKIIa::C1V1 and DIO-SSFO in the mPFC of PV::Cre mice were performed.

While handling cells or tissues expressing SSFO, care was taken to minimize light exposure to prevent activation by ambient light. Before each experiment, a 20 s pulse of 590 nm light was applied to convert all of the SSFO channels to the dark state and prevent run-down of photocurrents. For acquisition of SSFO activation and deactivation spectra, recordings from cultured neurons were made in voltage clamp mode. For recording activation spectra, a 1 s pulse of varying wavelength was applied, followed by a 10 s 590 nm pulse. Deactivation spectra were acquired by first applying a 1 s 470 nm pulse to activate SSFO, followed by a 10 s pulse of varying wavelength. Net activation or deactivation was calculated by dividing the photocurrent change after the first or second pulse, respectively, by the maximum photocurrent change induced by the peak wavelength for that cell. Negative values in deactivation spectra resulted from traces in which, for example, a 10 s 470 nm pulse led to a slight increase in photocurrent rather than deactivate the channels. This could be the result of the relatively wide (20 nm) band-pass filter width used for these recordings with the Sutter DG-4. Intermediate wavelengths (between 470 nm and 520 nm) are expected to have a mixed effect on the channel population for the same reasons.

Photon flux calculations for SSFO integration properties were conducted by calculating the photon flux through the microscope objective at each light power, and then dividing to reach the photon flux across the cell surface, based on the diameter of the recorded cells and approximating cell shape as a spheroid.

Results

Figure 34:
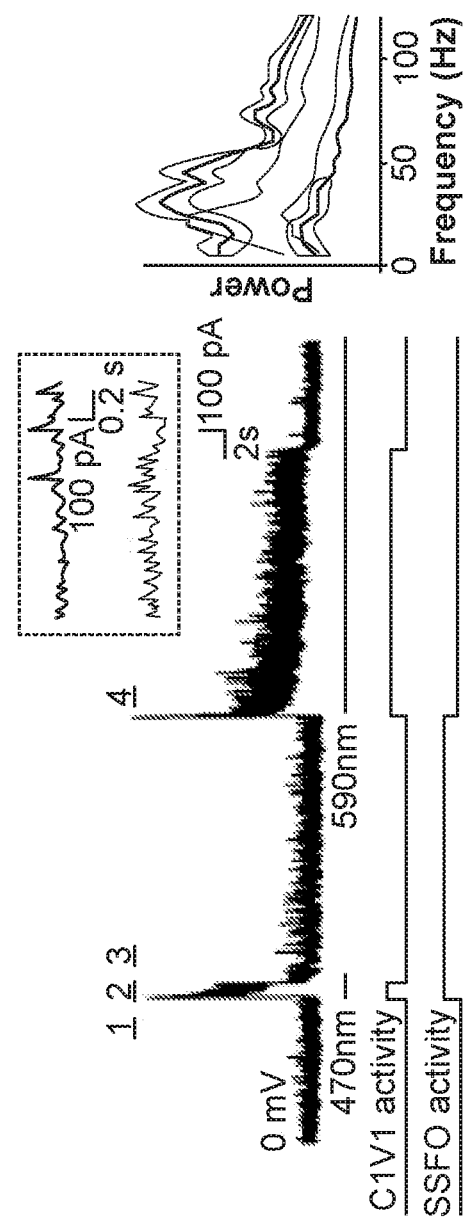
Figure 35:
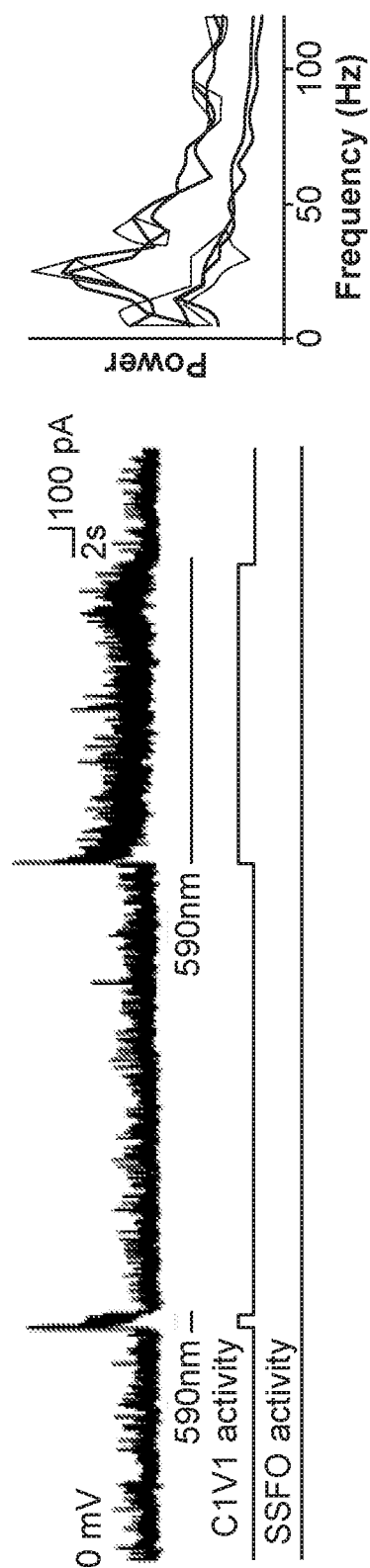
Figure 36:
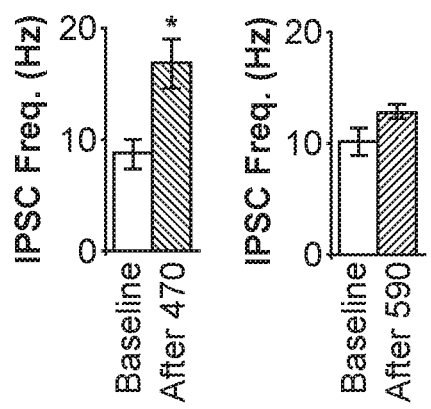

SSFO is a novel multiply-engineered channelrhodopsin with a decay constant of 29 minutes that can be effectively deactivated at the same wavelengths that activate C1V1 and permits bistable excitation of neurons over many minutes with enhanced light sensitivity. Information regarding SSFOs can be found in International Patent Application Publication No: WO 2010/056970 and U.S. Patent Application Nos. 61/410,704 and 61/410,711, the contents of which are hereby incorporated by reference herein in their entireties. Double virus injections to express CaMKIIa::C1V1 and DIO::SSFO in acute slices from the mPFC of PV::Cre mice were performed. Under these conditions, excitatory pyramidal cells should respond to redshifted light, and inhibitory PV cells to blue light. Indeed, in response to a 1 s 470 nm light pulse to activate SSFO in the PV cells, the rate of ongoing IPSCs was stably increased from 8.5±1.2 Hz at baseline (period 3, FIG. 34) to 16.8±2.1 Hz after the blue light pulse (period 2; n=4 recordings, p<0.005, paired t-test; FIG. 35), showing persistent activation of the SSFO-expressing inhibitory cells. Even though 470 nm light will also transiently activate C1V1, this activation can only occur during the light pulse itself due to the very fast deactivation of C1V1 after light-off; the prolonged post-light period is characterized by SSFO activity only (FIG. 34), illustrating temporal separation of optogenetic control modes. Interestingly, during this prolonged period of elevated PV neuron activity, no significantly elevated peak in the IPSC power spectrum was elicited, suggesting that direct activation of PV neurons alone in this reduced preparation is insufficient to elicit gamma synchrony in the network. However, in marked contrast, during the 470 nm light pulse itself when the same level of PV neuron activation but also partial activation of C1V1-expressing pyramidal cells is also expected, a pronounced gamma peak was consistently observed (peak frequency 39.2±3.5 Hz; n=4 recordings;) that extended into the high-gamma range (>60 Hz).

Moreover, in the same experiments (indeed, later in the same recorded sweeps), direct activation in this case of C1V1-pyramidal cells alone with 590 nm light (which simultaneously activates C1V1 in PY cells and deactivates the SSFO in PV cells) led to robust gamma synchrony, with a lower frequency peak (26.6±1 Hz, n=6 recordings). Demonstrating that any residual PV neuron activity linked to the prior history of SSFO activation in PV cells was not necessary for this effect, otherwise-identical sweeps with only a history of C1V1 activation in the pyramidal cells and no prior history of elevated IPSC rate elicited the same result). These results illustrate the integrated principle of spectrotemporal combinatorial control, and also suggest that elevating activity in pyramidal neurons can give rise through network properties to gamma oscillations[31]. Interestingly, during the 470 nm light pulse, when activation of both PV and pyramidal cells was expected, gamma synchrony was consistently observed at higher frequencies than when only excitatory neurons were activated, supporting and extending information on the coordinated importance of both PV and pyramidal cells in eliciting gamma oscillations.[31-33]

CONCLUSION

In the course of this work, a family of new tools was generated that are referred to as C1V1 variants. C1V1 is a red-shifted opsin gene assembled, remarkably, from pieces of other opsin genes that do not express well alone in neurons, but which were identified in earlier genomic searches (VChR1 and ChR1). C1V1 contains no ChR2 sequence at all, yet its multiply-engineered variants reported here now represent the most potent, most redshifted, and most stable channelrhodopsins known. Mutagenesis in key amino acid positions throughout the retinal binding pocket led to the generation of (1) C1V1(E162T), a high-expressing redshifted opsin gene generated as a fast homolog of the ChETA mutation; (2) C1V1(E122T) which displays the reddest action spectrum shoulder and can even be used to fire action potentials with red light (3) C1V1(E122T/E162T)—a combination mutant with the lowest desensitization, fastest deactivation, least violet-light activation for minimal cross-activation with ChR2, and strong expression. Indeed, C1V1 variants may be selected for different applications based on considerations of current size, deactivation kinetics, and action spectrum (Table 1)—for example, in two-photon work, since 2P activation of ChR2 has been difficult due to current size and rapid kinetics of channel closure, C1V1(E162T) is likely to be of interest. The C1V1 variants enabled direct testing of the hypothesis that increasing levels of elevated cellular E/I balance would give rise to increasing intensities of gamma rhythmicity, a phenomenon previously linked to both schizophrenia and autism. Of course, the different tools are also synergistic; using C1V1 variants together with ChR2 permitted reliable and separate driving of spiking in the two distinct neuronal populations addressed in this study—the excitatory pyramidal neurons and the fast-spiking, parvalbumin-expressing inhibitory interneurons, and confirm that steady elevated cellular E/I balance was effective at generating gamma-band circuit activity, capitalizing on both kinetic and spectral differences in the optogenetic tools. This type of combinatorial activation can be extended beyond multiple cell types to multiple neural pathway types—for example, the separable activation of spiking, within a single brain region, in two converging axonal afferent pathways arising from distinct locations—a long-sought goal of systems neuroscience.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. Various embodiments described above, and discussed in the attached Appendices may be implemented together and/or in other manners. One or more of the aspects in the present disclosure and in the Appendices can also be implemented in a more separated or integrated manner, as should be apparent and is useful in accordance with particular target applications. In particular, all publications and appendices cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Deisseroth, K. Optogenetics. *Nat Methods* 8, 26-29 (2011).
Boyden, E. S., Zhang, F., Bamberg, E., Nagel, G. & Deisseroth, K. Millisecond-timescale, genetically targeted optical control of neural activity. *Nat Neurosci* 8, 1263-1268 (2005).
Nagel, G. et al. Light activation of channelrhodopsin-2 in excitable cells of *Caenorhabditis elegans* triggers rapid behavioral responses. *Curr Biol* 15, 2279-2284 (2005).
Li, X. et al. Fast noninvasive activation and inhibition of neural and network activity by vertebrate rhodopsin and green algae channelrhodopsin. *Proc Natl Acad Sci USA* 102, 17816-17821 (2005).
Bi, A. et al. Ectopic expression of a microbial-type rhodopsin restores visual responses in mice with photoreceptor degeneration. *Neuron* 50, 23-33 (2006).
Schroll, C. et al. Light-induced activation of distinct modulatory neurons triggers appetitive or aversive learning in *Drosophila* larvae. *Curr Biol* 16, 1741-1747 (2006).
Zhang, F. et al. Multimodal fast optical interrogation of neural circuitry. *Nature* 446, 633-639 (2007).
Douglass, A. D., Kraves, S., Deisseroth, K., Schier, A. F. & Engert, F. Escape behavior elicited by single, channelrhodopsin-2-evoked spikes in zebrafish somatosensory neurons. *Curr Biol* 18, 1133-1137 (2008).
Hagglund, M., Borgius, L, Dougherty, K. J. & Kiehn, O. Activation of groups of excitatory neurons in the mammalian spinal cord or hindbrain evokes locomotion. *Nature neuroscience* 13, 246-252, doi:10.1038/nn.2482 (2010).
Huber, D. et al. Sparse optical microstimulation in barrel cortex drives learned behaviour in freely moving mice. *Nature* 451, 61-64 (2008).
Hira, R. et al. Transcranial optogenetic stimulation for functional mapping of the motor cortex. *J Neurosci Methods* 179, 258-263 (2009).
Higley, M. J. & Sabatini, B. L. Competitive regulation of synaptic Ca2+ influx by D2 dopamine and A2A adenosine receptors. *Nature neuroscience* 13, 958-966, doi:10.1038/nn.2592 (2010).
Petreanu, L., Huber, D., Sobczyk, A. & Svoboda, K. Channelrhodopsin-2-assisted circuit mapping of long-range callosal projections. *Nat Neurosci* 10, 663-668 (2007).
Ishizuka, T., Kakuda, M., Araki, R. & Yawo, H. Kinetic evaluation of photosensitivity in genetically engineered neurons expressing green algae light-gated channels. *Neurosci Res* 54, 85-94 (2006).
Nagel, G. et al. Channelrhodopsin-2, a directly light-gated cation-selective membrane channel. *Proc Natl Acad Sci USA* 100, 13940-13945 (2003).
Rickgauer, J. P. & Tank, D. W. Two-photon excitation of channelrhodopsin-2 at saturation. *Proc Natl Arad Sci USA* 106, 15025-15030 (2009).
Yonehara, K. et al. Spatially asymmetric reorganization of inhibition establishes a motion-sensitive circuit. *Nature* 469, 407-410, doi:10.1038/nature09711 (2011).
Yaroslaysky, A. N. et al. Optical properties of selected native and coagulated human brain tissues in vitro in the visible and near infrared spectral range. *Phys Med Biol* 47, 2059-2073 (2002).
Wang, H. et al. Molecular determinants differentiating photocurrent properties of two channelrhodopsins from *chlamydomonas*. *J Biol Chem* 284, 5685-5596 (2009).
Wen, L. et al. Opto-current-clamp actuation of cortical neurons using a strategically designed channelrhodopsin. *PLoS One* 5, e12893 (2010).
Zhang, F. et al. Red-shifted optogenetic excitation: a tool for fast neural control derived from *Volvox carteri*. *Nat Neurosci* 11, 631-633 (2008).
Berndt, A., Yizhar, O., Gunaydin, L. A., Hegemann, P. & Deisseroth, K. Bi-stable neural state switches. *Nat Neurosci* 12, 229-234 (2009).
Barnann, C., Gueta, R., Kleinlogel, S., Nagel, G. & Bamberg, E. Structural guidance of the photocycle of channelrhodopsin-2 by an interhelical hydrogen bond. *Biochemistry* 49, 267-278 (2010).
Schoenenberger, P., Gerosa, D. & Oertner, T. G. Temporal control of immediate early gene induction by light. *PLoS One* 4, e8185 (2009).
Stehfest, K., Ritter, E., Berndt, A., Bartl, F. & Hegernann, P. The branched photocycle of the slow-cycling channelrhodopsin-2 mutant C128T. *J Mol Biol* 398, 690-702 (2010).
Sohal, V. S., Zhang, F., Yizhar, O. & Deisseroth, K. Parvalbumin neurons and gamma rhythms enhance cortical circuit performance. *Nature* 459, 698-702 (2009).

Lin, J. Y., Lin, M. Z., Steinbach, P. & Tsien, R. Y. Characterization of engineered channelrhodopsin variants with improved properties and kinetics. *Biophys J* 96, 1803-1814 (2009).

Gunaydin, L. A. et al. Ultrafast optogenetic control. *Nat Neurosci* 13, 387-392 (2010).

Tittor, J., Schweiger, U., Oesterhelt, D. & Bamberg, E. Inversion of proton translocation in bacteriorhodopsin mutants D85N, D85T, and D85,96N. *Biophys J* 67, 1682-1690 (1994).

Sugiyama, Y. et al. Photocurrent attenuation by a single polar-to-nonpolar point mutation of channelrhodopsin-2. *Photochem Photobiol Sci* 8, 328-336 (2009).

Adesnik, H. & Scanziani, M. Lateral competition for cortical space by layer-specific horizontal circuits. *Nature* 464, 1155-1160 (2010).

Colgin, L. L. et al. Frequency of gamma oscillations routes flow of information in the hippocampus. *Nature* 462, 353-357 (2009).

Cardin, J. A. et al. Driving fast-spiking cells induces gamma rhythm and controls sensory responses. *Nature* 459, 663-667 (2009).

Bamann, C., Kirsch, T., Nagel, G. & Bamberg, E. Spectral characteristics of the photocycle of channelrhodopsin-2 and its implication for channel function. *J Mol Biol* 375, 686-694 (2008).

```
SEQUENCES
(Humanized C1V1 amino acid sequence)
                                                              SEQ ID NO: 1
MSRRPWLLALALAVALAAGSAGASTGSDATVPVATQDGPDYVFHRAHERMLFQTSYTLENNGSVICIPNNGQCGCLAWLK

SNGTNAEKLAANILQWITFALSALCLMFYGYQTWKSTCGWEEIYVATIEMIKFIIEYFHEFDEPAVIYSSNGNKTVWLRY

AEWLLTCPVLLIHLSNLTGLKDDYSKRTMGLLVSDVGCIVWGATSAMCTGWTKILFFLISLSYGMYTYFHAAKVYIEAFH

TVPKGICRELVRVMAWTFFVAWGMFPVLFLLGTEGFGHISPYGSAIGHSILDLIAKNMWGVLGNYLRVKIHEHILLYGDI

RKKQKITIAGQEMEVETLVAEEED (Humanized C1V1 nucleotide sequence)
                                                              SEQ ID NO: 2
atgtcgcgacgcccgtggctccttgctctcgcattggcggtggcgcttgcagcgggatcggcaggagcgtcaaccggaag cgatgcgaccgtccccgtggctacgcaagacggaccagattacgtgttccacagagcccacgagcggatgttgtttcaga catcatacacacttgaaaacaatggtagcgtcatttgcatccctaacaatgggcagtgttttgcctggcctggttgaaa tcgaacggtacgaacgccgagaagctggcggcgaacattctgcagtggatcacattcgcactctcggcgctctgccttat gttctatggctaccagacttggaaatccacgtgtggtttgggaagagatctacgtagcaaccattgaaatgatcaagttta tcattgagtatttccatgagtttgacgaaccggccgtaatctactcatcgaatgggaataagacagtctggttgaggtat gcggagtggctcctcacctgcccggtccttctgatccatctgagcaacctcacaggcctgaaggacgattatagcaaaag gactatgggcctgttggtttctgatgtgggatgcatcgtgtggggcgcaaccagcgccatgtgtacggggtggacgaaga tcctgttcttcctcatctcattgagctatggtatgtatacctattttcatgctgctaaagtttatatcgaagcattccac acagttccaaaagggatttgtcgagaactggtccgagtgatggcctggacattctttgtggcttggggaatgtttccagt cctgtttctgctgggcacggaaggattcggtcatatcagccctttatggatctgccattgggcactccatcctcgacctga ttgcaaagaacatgtggggtgtgctggggaattacctgcgcgtcaaaatccacgagcacatcctgttgtatggcgacatc agaaagaagcagaaaattacgatcgccggccaagagatggaggttgagacactggtggctgaagaggaggactaa (Humanized C1V1 E122T amino acid sequence)
                                                              SEQ ID NO: 3
MSRRPWLLALALAVALAAGSAGASTGSDATVPVATQDGPDYVFHRAHERMLFQTSYTLENNGSVICIPNNGQCFCLAWLK

SNGTNAEKLAANILQWITFALSALCLMFYGYQTWKSTCGWEIIYVATIEMIKFIIEYFHEFDEPAVIYSSNGNKTVWLTY

AEWLLTCPVLLIHLSNLTGLKDDYSKRTMGLLVSDVGCIVWGATSAMCTGWTKILFFLISLSYGMYTYFHAAKVYIEAFH

TVPKGICRELVRVMAWTFFVAWGMFPVLFLLGTEGFGHISPYGSAIGHSILDLIAKNMWGVLGNYLRVKIHEHILLYGDI

RKKQKITIAGQEMEVETLVAEEED (Humanized C1V1 E122T nucleotide sequence)
                                                              SEQ ID NO: 4
atgtcgcgacgcccgtggctccttgctctcgcattggcggtggcgcttgcagcgggatcggcaggagcgtcaaccggaag cgatgcgaccgtccccgtggctacgcaagacggaccagattacgtgttccacagagcccacgagcggatgttgtttcaga catcatacacacttgaaaacaatggtagcgtcatttgcatccctaacaatgggcagtgttttgcctggcctggttgaaa tcgaacggtacgaacgccgagaagctggcggcgaacattctgcagtggatcacattcgcactctcggcgctctgccttat gttctatggctaccagacttggaaatccacgtgtggtttgggaaaccatctacgtagcaaccattgaaatgatcaagttta
```

-continued

```
tcattgagtatttccatgagtttgacgaaccggccgtaatctactcatcgaatgggaataagacagtctggttgaggtat gcggagtggctcctcacctgcccggtccttctgatccatctgagcaacctcacaggcctgaaggacgattatagcaaaag gactatgggcctgttggtttctgatgtgggatgcatcgtgtggggcgcaaccagcgccatgtgtacggggtggacgaaga tcctgttcttcctcatctcattgagctatggtatgtatacctattttcatgctgctaaagtttatatcgaagcattccac acagttccaaaagggatttgtcgagaactggtccgagtgatggcctggacattctttgtggcttggggaatgtttccagt cctgtttctgctgggcacggaaggattcggtcatatcagcccttatggatctgccattgggcactccatcctcgacctga ttgcaaagaacatgtggggtgtgctggggaattacctgcgcgtcaaaatccacgagcacatcctgttgtatggcgacatc agaaagaagcagaaaattacgatcgccggccaagagatggaggttgagacactggtggctgaagaggaggactaa
```

(Humanized C1V1 E162T amino acid sequence)

SEQ ID NO: 5

MSRRPWLLALALAVALAAGSAGASTGSDATVPVATQDGPDYVFHRAHERMLFQTSYTLENNGSVICIPNNGQCFCLAWLK

SNGTNAEKLAANILQWITFALSALCLMFYGYQTWKSTCGWEEIYVATIEMIKFIIEYFHEFDEPAVIYSSNGNKTVWLRY

ATWLLCPVLLIHLSNLTGLKDDYSKRTMGLLVSDVGCIVWGATSAMCTGWTKILFFLISLSYGMYTYFHAAKVYIEAFHT

VPKGICRELVRVMAWTFFVAWGMFPVFLLGTEGFGHISPYGSAIGHSILDLIAKNMWGVLGNYLRVKIHEHILLYGDIRK

KQKITIAGQEMEVETLVAEEED (Humanized C1V1 E162T nucleotide sequence)

SEQ ID NO: 6 atgtcgcgacgcccgtggctccttgctctcgcattggcggtggcgcttgcagcgggatcggcaggagcgtcaaccggaag cgatgcgaccgtccccgtggctacgcaagacggaccagattacgtgttccacagagcccacgagcggatgttgtttcaga catcatacacacttgaaaacaatggtagcgtcatttgcatccctaacaatgggcagtgtttttgcctggcctggttgaaa tcgaacggtacgaacgccgagaagctggcggcgaacattctgcagtggatcacattcgcactctcggcgctctgccttat gttctatggctaccagacttggaaatccacgtgtggttgggaagagatctacgtagcaaccattgaaatgatcaagttta tcattgagtatttccatgagtttgacgaaccggccgtaatctactcatcgaatgggaataagacagtctggttgaggtat gcgacgtggctcctcacctgcccggtccttctgatccatctgagcaacctcacaggcctgaaggacgattatagcaaaag gactatgggcctgttggtttctgatgtgggatgcatcgtgtggggcgcaaccagcgccatgtgtacggggtggacgaaga tcctgttcttcctcatctcattgagctatggtatgtatacctattttcatgctgctaaagtttatatcgaagcattccac acagttccaaaagggatttgtcgagaactggtccgagtgatggcctggacattctttgtggcttggggaatgtttccagt cctgtttctgctgggcacggaaggattcggtcatatcagcccttatggatctgccattgggcactccatcctcgacctga ttgcaaagaacatgtggggtgtgctggggaattacctgcgcgtcaaaatccacgagcacatcctgttgtatggcgacatc agaaagaagcagaaaattacgatcgccggccaagagatggaggttgagacactggtggctgaagaggaggactaa (Humanized C1V1 E122T/E162T amino acid sequence)

SEQ ID NO: 7

MSRRPWLLALALAVALAAGSAGASTGSDATVPVATQDGPDYVFHRAHERMLFQTSYTLENNGSVICIPNNGQCFCLAWLK

SNGTNAEKLAANILQWITFALSALCLMFYGYQTWKSTCGWETIYVATIEMIKFIIEYFHEFDEPAVIYSSNGNKTVWLRY

ATWLLTCPVLLIHLSNLTGLKDDYSKRTMGLLVSDVGCIVWGATSAMCTGWTKILFFLISLSYGMYTYFHAAKVYIEAFH

TVPKGICRELVRVMAWTFFVAWGMFPVLFLLGTEGFGHISPYGSAIGHSILDLIAKNMWGVLGNYLRVKIHEHILLYGDI

RKKQKITIAGQEMEVETLVAEEED (Humanized C1V1 E122T/E162T nucleotide sequence)

SEQ ID NO: 8 atgtcgcgacgcccgtggctccttgctctcgcattggcggtggcgcttgcagcgggatcggcaggagcgtcaaccggaag cgatgcgaccgtccccgtggctacgcaagacggaccagattacgtgttccacagagcccacgagcggatgttgtttcaga catcatacacacttgaaaacaatggtagcgtcatttgcatccctaacaatgggcagtgtttttgcctggcctggttgaaa tcgaacggtacgaacgccgagaagctggcggcgaacattctgcagtggatcacattcgcactctcggcgctctgccttat gttctatggctaccagacttggaaatccacgtgtggttgggaaaccatctacgtagcaaccattgaaatgatcaagttta -continued

```
tcattgagtatttccatgagtttgacgaaccggccgtaatctactcatcgaatgggaataagacagtctggttgaggtat gcgacgtggctcctcacctgcccggtccttctgatccatctgagcaacctcacaggcctgaaggacgattatagcaaaag gactatgggcctgttggtttctgatgtgggatgcatcgtgtggggcgcaaccagcgccatgtgtacggggtggacgaaga tcctgttcttcctcatctcattgagctatggtatgtatacctatttttcatgctgctaaagtttatatcgaagcattccac acagttccaaaagggatttgtcgagaactggtccgagtgatggcctggacattcttttgtggcttggggaatgtttccagt cctgtttctgctgggcacggaaggattcggtcatatcagcccttatggatctgccattgggcactccatcctcgacctga ttgcaaagaacatgtggggtgtgctggggaattacctgcgcgtcaaaatccacgagcacatcctgttgtatggcgacatc agaaagaagcagaaaattacgatcgccggccaagagatggaaggttgagacactggtggctgaagaggaggactaa
```

(Alternative Humanized C1V1 amino acid sequence (C1V1_25))
SEQ ID NO: 9
```
MSRRPWLLALALAVALAAGSAGASTGSDATVPVATQDGPDYVFHRAHERMLFQTSYTLENNGSVICIPNNGQCFCLAWLK

SNGTNAEKLAANILQWITFALSALCLMFYGYQTWKSTCGWEEIYVATIEMIKFIIEYFHEFDEPATLWLSSGNGVVWMRY

GEWLLTCPVLLIHLSNLTGLKDDYSKRTMGLLVSDVGCIVWGATSAMCTGWTKILFFLSSLSYGMYTYFHAAKVYIEAFH

TVPKGICRELVRVMAWTFFVAWGMFPVLFLLGTEGFGHISPYGSAIGHSILDLIAKNMWGVLGNYLRVKIHEHILLYGDI

RKKQKITIAGQEMEVETLVAEEED
```

(Alternative Humanized C1V1 nucleotide sequence (C1V1_25))
SEQ ID NO: 10
```
Atgagcagacggccctggctgctggccctggctctcgctgtggccctggccgccggcagcgccggagccagcaccggcag cgacgccaccgtgcccgttgccacacaggacggccccgactacgtgttccaccgggcccacgagcggatgctgttccaga ccagctacacccttgaaaacaacggcagcgtgatctgcatccccaacaacggccagtgcttctgcctggcctggctgaag tccaacggcaccaacgccgagaagctggccgccaacatcctgcagtggatcaccttcgccctgtctgccctgtgcctgat gttctacggctaccagacctggaagtccacctgcggctgggaggaaatctacgtggccaccatcgagatgatcaagttca tcatcgagtacttccacgagttcgacgagcccgccacccctgtggctgtccagcggaaacggcgtggtgtggatgagatac ggcgagtggctgctgacctgccctgtgctgctgatccacctgagcaacctgaccggactgaaggatgactacagcaagag aaccatgggactgctggtgtccgatgtgggatgcatcgtgtggggagccacctccgccatgtgcaccggatggaccaaga tcctgttcttcctgatcagcctgagctacggaatgtacacctacttccacgccgccaaggtgtacattgaggcctttcac accgtgcctaagggaatctgcagagaactggtcagagtgatggcctggaccttcttcgtggcctggggaatgtttccctgt gctgttcctgctgggaaccgagggattcggacacatcagcccttacggaagcgccatcggacacagcatcctggatctga tcgccaagaacatgtggggagtgctgggaaactacctgagagtgaagatccacgagcacatcctgctgtacggcgacatc agaaagaagcagaagatcaccatcgccggacaggaaatggaagtcgagaccctggtggccgaggaagaggat
```

ChR2 amino acid sequence
SEQ ID NO: 11
```
MDYGGALSAVGRELLFVTNPVVVNGSVLVPEDQCYCAGWIESRGTNGAQTASNVLQWLAAGFSILLLMFYAYQTWKSTCG

WEEIYVCAIEMVKVILEFFFEFKNPSMLYLATGHRVQWLRYAEWLLTCPVILIHLSNLTGLSNDYSRRTMGLLVSDIGTI

VWGATSAMATGYVKVIFFCLGLCYGANTFFHAAKAYIEGYHTVPKGRCRQVVTGMAWLFFVSWGMFPILFILGPEGFGVL

SVYGSTVGHTIIDLMSKNCWGLLGHYLRVLIHEHILIHGDIRKTTKLNIGGTEIEVETLVEDEAEAGAVP
```

ChR2(H134R)
SEQ ID NO: 12
```
MDYGGALSAVGRELLFVTNPVVVNGSVLVPEDQCYCAGWIESRGTNGAQTASNVLQWLAAGFSILLLMFYAYQTWKSTCG

WEEIYVCAIEMVKVILEFFFEFKNPSMLYLATGHRVQWLRYAEWLLTCPVILIRLSNLTGLSNDYSRRTMGLLVSDIGTI

VWGATSAMATGYVKVIFFCLGLCYGANTFFHAAKAYIEGYHTVPKGRCRQVVTGMAWLFFVSWGMFPILFILGPEGFGVL

SVYGSTVGHTIIDLMSKNCWGLLGHYLRVLIHEHILIHGDIRKTTKLNIGGTEIEVETLNEDEAEAGAVP
```

SFO
SEQ ID NO: 13
```
MDYGGALSAVGRELLFVTNPVVVNGSVLVPEDQCYCAGWIESRGTNGAQTASNVLQWLAAGFSILLLMFYAYQTWKSTCG

WEEIYVCAIEMVKVILEFFFEFKNPSMLYLATGHRVQWLRYAEWLLTSPVILIHLSNLTGLSNDYSRRTMGLLVSDIGTI
```

```
VWGATSAMATGYVKVIFFCLGLCYGANTFFHAAKAYIEGYHTVPKGRCRQVVTGMAWLFFVSWGMFPILFILGPEGFGVL

SVYGSTVGHTIIDLMSKNCWGLLGHYLRVLIHEHILIHGDIRKTTKLNIGGTEIEVETLVEDEAEAGAVP
```

(SSFO)

SEQ ID NO: 14

```
MDYGGALSAVGRELLFVTNPVVVNGSVLVPEDQCYCAGWIESRGTNGAQTASNVLQWLAAGFSILLLMFYAYQTWKSTCG

WEEIYVCAIEMVKVILEFFFEFKNPSMLYLATGHRVQWLRYAEWLLTSPVILIHLSNLTGLSNDYSRRTMGLLVSAIGTI

VWGATSAMATGYVKVIFFCLGLCYGANTFFHAAKAYIEGYHTVPKGRCRQVVTGMAWLFFVSWGMFPILFILGPEGFGVL

SVYGSTVGHTIIDLMSKNCWGLLGHYLRVLIHEHILIHGDIRKTTKLNIGGTEIEVETLVEDEAEAGAVP
```

---

What is claimed is:

1. A method for identifying a chemical compound that selectively inhibits the depolarization of excitatory or inhibitory neurons residing in the same microcircuit, the method comprising:
   (a) selectively depolarizing an excitatory neuron comprising a first light-activated protein with light having a first wavelength or selectively depolarizing an inhibitory neuron comprising a second light-activated protein with light having a second wavelength; wherein the first or the second light activated protein is a chimeric protein comprising an amino acid sequence having at least 95% amino acid sequence identity to the amino acid sequence set forth in SEQ ID NO:1;
   (b) measuring an excitatory post synaptic potential (EPSP) in response to selectively depolarizing the excitatory neuron comprising the first light-activated protein or measuring an inhibitory post synaptic current (IPSC) in response to selectively depolarizing an inhibitory neuron comprising the second light-activated protein;
   (c) contacting the excitatory neuron or the inhibitory neuron with a chemical compound; and
   (d) measuring the excitatory post synaptic potential (EPSP) or measuring the inhibitory post synaptic current (IPSC) to determine if contacting either the excitatory neuron or the inhibitory neuron with the chemical compound selectively inhibits the depolarization of either neuron.

2. The method of claim 1, wherein the first light-activated protein comprises an amino acid sequence at least 95% identical to the amino acid sequence set forth in SEQ ID NO: 1, 3, 5, or 7.

3. The method of claim 1, wherein the first light-activated protein is activated by green light or the second light-activated protein is activated by violet light.

4. The method of claim 1, wherein the inhibitory or excitatory neuron is in a living non-human animal.

5. The method of claim 1, wherein the inhibitory or excitatory neuron is in living brain slices from a non-human animal.

6. The method of claim 1, wherein the inhibitory or excitatory neuron is from the prefrontal cortex.

7. The method of claim 1, wherein the excitatory neuron comprises a pyramidal neuron or the inhibitory neuron comprises a parvalbumin neuron.

8. The method of claim 1, wherein the chemical compound is a member of a combinatorial chemical library.

9. The method of claim 1, further comprising assaying the chemical compound on cardiac tissue to determine if the compound adversely affects cardiac action potential.

10. The method of claim 1, wherein the second light-activated protein comprises an amino acid sequence at least 95% identical to the amino acid sequence set forth in SEQ ID NO:11, 12, 13, or 14.

11. A light-responsive chimeric polypeptide comprising, in order from N-terminus to C-terminus:
   a) an amino acid sequence having at least 90% amino acid sequence identity to amino acids 1-163 of the ChR1 amino acid sequence set forth in SEQ ID NO:16; and
   b) an amino acid sequence having at least 90% amino acid sequence identity to amino acids 120-300 of SEQ ID NO:17.

12. The light-responsive chimeric polypeptide of claim 11, wherein the polypeptide is activated by light of a wavelength between about 540 nm to about 560 nm.

13. The chimeric polypeptide of claim 11, further comprising a C-terminal trafficking signal.

14. The chimeric polypeptide of claim 13, wherein the trafficking signal comprises the amino acid sequence KSRITSEGEYIPLDQIDINV (SEQ ID NO:15).

15. The chimeric polypeptide of claim 11, wherein the light-responsive chimeric polypeptide comprises a Glu to Thr amino acid substitution at position 122 relative to the amino acid sequence set forth in SEQ ID NO:16.

16. The chimeric polypeptide of claim 11, wherein the light-responsive chimeric polypeptide comprises a Glu to Thr amino acid substitution at position 162 relative to the amino acid sequence set forth in SEQ ID NO:16.

17. The chimeric polypeptide of claim 11, wherein the light-responsive chimeric polypeptide comprises a Glu to Thr amino acid substitution at position 122 and a Glu to Thr amino acid substitution at position 162 relative to the amino acid sequence set forth in SEQ ID NO:16.

18. A polynucleotide comprising a nucleotide sequence encoding a light-responsive chimeric polypeptide comprising, in order from N-terminus to C-terminus:
   a) an amino acid sequence having at least 90% amino acid sequence identity to amino acids 1-163 of the ChR1 amino acid sequence set forth in SEQ ID NO: 16; and
   b) an amino acid sequence having at least 90% amino acid sequence identity to amino acids 120-300 of SEQ ID NO: 17.

19. The polynucleotide of claim 18, wherein the polynucleotide is an expression vector.

20. The polynucleotide of claim 19, wherein the expression vector is a viral vector.

21. The polynucleotide of claim 18, wherein the nucleotide sequence is operably linked to a promoter.

\* \* \* \* \*

SEQUENCE LISTING

<160> NUMBER OF SEQ ID NOS: 17

<210> SEQ ID NO 1
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 1

```
Met Ser Arg Arg Pro Trp Leu Leu Ala Leu Ala Leu Ala Val Ala Leu
  1               5                  10                  15

Ala Ala Gly Ser Ala Gly Ala Ser Thr Gly Ser Asp Ala Thr Val Pro
             20                  25                  30

Val Ala Thr Gln Asp Gly Pro Asp Tyr Val Phe His Arg Ala His Glu
         35                  40                  45

Arg Met Leu Phe Gln Thr Ser Tyr Thr Leu Glu Asn Asn Gly Ser Val
     50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
```

```
                260                 265                 270
Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 2
<211> LENGTH: 1035
<212> TYPE: DNA
<213> ORGANISM: Artificial Sequence
<220> FEATURE:
<223> OTHER INFORMATION: Synthetic polynucleotide

<400> SEQUENCE: 2
atgtcgcgac gcccgtggct ccttgctctc gcattggcgg tggcgcttgc agcgggatcg      60
gcaggagcgt caaccggaag cgatgcgacc gtccccgtgg ctacgcaaga cggaccagat     120
tacgtgttcc acagagccca cgagcggatg ttgtttcaga catcatacac acttgaaaac     180
aatggtagcg tcatttgcat ccctaacaat gggcagtgtt tttgcctggc ctggttgaaa     240
tcgaacggta cgaacgccga aagctggcg gcgaacattc tgcagtggat cacattcgca     300
ctctcggcgc tctgccttat gttctatggc taccagactt ggaaatccac gtgtggttgg     360
gaagagatct acgtagcaac cattgaaatg atcaagttta tcattgagta tttccatgag     420
tttgacgaac cggccgtaat ctactcatcg aatgggaata agacagtctg gttgaggtat     480
gcggagtggc tcctcacctg cccggtcctt ctgatccatc tgagcaacct cacaggcctg     540
aaggacgatt atagcaaaag gactatgggc ctgttggttt ctgatgtggg atgcatcgtg     600
tggggcgcaa ccagcgccat gtgtacgggg tggacgaaga tcctgttctt cctcatctca     660
ttgagctatg gtatgtatac ctatttcat gctgctaaag tttatatcga agcattccac     720
acagttccaa aagggatttg tcgagaactg gtccgagtga tggcctggac attctttgtg     780
gcttggggaa tgtttccagt cctgtttctg ctgggcacgg aaggattcgg tcatatcagc     840
ccttatggat ctgccattgg cactccatc ctcgacctga ttgcaagaa catgtggggt     900 gtgctgggga attacctgcg cgtcaaaatc cacgagcaca tcctgttgta tggcgacatc     960
agaaagaagc agaaaattac gatcgccggc caagagatgg aggttgagac actggtggct    1020
gaagaggagg actaa                                                     1035

<210> SEQ ID NO 3
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 3

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30
```

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
            115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 4
<211> LENGTH: 1035
<212> TYPE: DNA
<213> ORGANISM: Artificial Sequence
<220> FEATURE:
<223> OTHER INFORMATION: Synthetic polynucleotide

<400> SEQUENCE: 4
atgtcgcgac gcccgtggct ccttgctctc gcattggcgg tggcgcttgc agcgggatcg      60
gcaggagcgt caaccggaag cgatgcgacc gtccccgtgg ctacgcaaga cggaccagat     120
tacgtgttcc acagagccca cgagcggatg ttgtttcaga catcatacac acttgaaaac     180
aatggtagcg tcatttgcat ccctaacaat gggcagtgtt tttgcctggc ctggttgaaa     240
tcgaacggta cgaacgccga gaagctggcg gcgaacattc tgcagtggat cacattcgca     300

```
ctctcggcgc tctgccttat gttctatggc taccagactt ggaaatccac gtgtggttgg    360
gaaaccatct acgtagcaac cattgaaatg atcaagttta tcattgagta tttccatgag    420
tttgacgaac cggccgtaat ctactcatcg aatgggaata agacagtctg gttgaggtat    480
gcggagtggc tcctcacctg cccggtcctt ctgatccatc tgagcaacct cacaggcctg    540
aaggacgatt atagcaaaag gactatgggc ctgttggttt ctgatgtggg atgcatcgtg    600
tggggcgcaa ccagcgccat gtgtacgggg tggacgaaga tcctgttctt cctcatctca    660
ttgagctatg gtatgtatac ctatttcat gctgctaaag tttatatcga agcattccac    720
acagttccaa aagggatttg tcgagaactg gtccgagtga tggcctggac attctttgtg    780
gcttggggaa tgtttccagt cctgtttctg ctgggcacgg aaggattcgg tcatatcagc    840
ccttatggat ctgccattgg gcactccatc ctcgacctga ttgcaaagaa catgtggggt    900
gtgctgggga attacctgcg cgtcaaaatc cacgagcaca tcctgttgta tggcgacatc    960
agaaagaagc agaaaattac gatcgccggc caagagatgg aggttgagac actggtggct   1020
gaagaggagg actaa                                                    1035
```

<210> SEQ ID NO 5
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 5

```
Met Ser Arg Arg Pro Trp Leu Leu Ala Leu Ala Leu Ala Val Ala Leu
 1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220
```

```
Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp
            340
```

<210> SEQ ID NO 6
<211> LENGTH: 1035
<212> TYPE: DNA
<213> ORGANISM: Artificial Sequence
<220> FEATURE:
<223> OTHER INFORMATION: Synthetic polynucleotide

<400> SEQUENCE: 6

```
atgtcgcgac gcccgtggct ccttgctctc gcattggcgg tggcgcttgc agcgggatcg      60
gcaggagcgt caaccggaag cgatgcgacc gtccccgtgg ctacgcaaga cggaccagat     120
tacgtgttcc acagagccca cgagcggatg ttgtttcaga catcatacac acttgaaaac     180
aatggtagcg tcatttgcat ccctaacaat gggcagtgtt tttgcctggc ctggttgaaa     240
tcgaacggta cgaacgccga gaagctggcg gcgaacattc tgcagtggat cacattcgca     300
ctctcggcgc tctgccttat gttctatggc taccagactt ggaaatccac gtgtggttgg     360
gaagagatct acgtagcaac cattgaaatg atcaagttta tcattgagta tttccatgag     420
tttgacgaac cggccgtaat ctactcatcg aatgggaata agacagtctg gttgaggtat     480
gcgacgtggc tcctcacctg cccggtcctt ctgatccatc tgagcaacct cacaggcctg     540
aaggacgatt atagcaaaag gactatgggc ctgttggttt ctgatgtggg atgcatcgtg     600
tggggcgcaa ccagcgccat gtgtacgggg tggacgaaga tcctgttctt cctcatctca     660
ttgagctatg gtatgtatac ctattttcat gctgctaaag tttatatcga agcattccac     720
acagttccaa aagggatttg tcgagaactg gtccgagtga tggcctggac attctttgtg     780
gcttggggaa tgtttccagt cctgtttctg ctgggcacgg aaggattcgg tcatatcagc     840
ccttatggat ctgccattgg cactccatc ctcgacctga ttgcaaagaa catgtggggt     900
gtgctgggga attacctgcg cgtcaaaatc cacgagcaca tcctgttgta tggcgacatc     960
agaaagaagc agaaaattac gatcgccggc caagagatgg aggttgagac actggtggct    1020
gaagaggagg actaa                                                      1035
```

<210> SEQ ID NO 7
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 7

| | | | | | | | | | | | | | | |
|---|---|---|---|---|---|---|---|---|---|---|---|---|---|---|
|Met|Ser|Arg|Arg|Pro|Trp|Leu|Leu|Ala|Leu|Ala|Leu|Ala|Val|Ala|Leu|
|1| | | |5| | | | |10| | | | |15| |

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 8
<211> LENGTH: 1035
<212> TYPE: DNA
<213> ORGANISM: Artificial Sequence
<220> FEATURE:
<223> OTHER INFORMATION: Synthetic polynucleotide

<400> SEQUENCE: 8
atgtcgcgac gcccgtggct ccttgctctc gcattggcgg tggcgcttgc agcgggatcg    60

-continued

```
gcaggagcgt caaccggaag cgatgcgacc gtccccgtgg ctacgcaaga cggaccagat    120
tacgtgttcc acagagccca cgagcggatg ttgtttcaga catcatacac acttgaaaac    180
aatggtagcg tcatttgcat ccctaacaat gggcagtgtt tttgcctggc ctggttgaaa    240
tcgaacggta cgaacgccga gaagctggcg gcgaacattc tgcagtggat cacattcgca    300
ctctcggcgc tctgccttat gttctatggc taccagactt ggaaatccac gtgtggttgg    360
gaaaccatct acgtagcaac cattgaaatg atcaagttta tcattgagta tttccatgag    420
tttgacgaac cggccgtaat ctactcatcg aatgggaata agacagtctg gttgaggtat    480
gcgacgtggc tcctcacctg cccggtcctt ctgatccatc tgagcaacct acacaggcctg    540 aaggacgatt atagcaaaag gactatgggc ctgttggttt ctgatgtggg atgcatcgtg    600
tggggcgcaa ccagcgccat gtgtacgggg tggacgaaga tcctgttctt cctcatctca    660
ttgagctatg gtatgtatac ctattttcat gctgctaaag tttatatcga agcattccac    720
acagttccaa aagggatttg tcgagaactg gtccgagtga tggcctggac attctttgtg    780
gcttggggaa tgtttccagt cctgtttctg ctgggcacgg aaggattcgg tcatatcagc    840
ccttatggat ctgccattgg gcactccatc ctcgacctga ttgcaaagaa catgtggggt    900
gtgctgggga attacctgcg cgtcaaaatc cacgagcaca tcctgttgta tggcgacatc    960
agaaagaagc agaaaattac gatcgccggc caagagatgg aggttgagac actggtggct    1020
gaagaggagg actaa                                                     1035
```

<210> SEQ ID NO 9
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 9

```
Met Ser Arg Arg Pro Trp Leu Leu Ala Leu Ala Leu Ala Val Ala Leu
  1               5                  10                  15

Ala Ala Gly Ser Ala Gly Ala Ser Thr Gly Ser Asp Ala Thr Val Pro
             20                  25                  30

Val Ala Thr Gln Asp Gly Pro Asp Tyr Val Phe His Arg Ala His Glu
         35                  40                  45

Arg Met Leu Phe Gln Thr Ser Tyr Thr Leu Glu Asn Asn Gly Ser Val
     50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Thr Leu Trp Leu Ser Ser Gly Asn Gly Val Val Trp Met Arg Tyr
145                 150                 155                 160

Gly Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190
```

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 10
<211> LENGTH: 1032
<212> TYPE: DNA
<213> ORGANISM: Artificial Sequence
<220> FEATURE:
<223> OTHER INFORMATION: Synthetic polynucleotide

<400> SEQUENCE: 10
atgagcagac ggccctggct gctggccctg gctctcgctg tggccctggc cgccggcagc     60
gccggagcca gcaccggcag cgacgccacc gtgcccgttg ccacacagga cggccccgac    120
tacgtgttcc accgggccca cgagcggatg ctgttccaga ccagctacac ccttgaaaac    180
aacggcagcg tgatctgcat ccccaacaac ggccagtgct tctgcctggc ctggctgaag    240
tccaacggca ccaacgccga aagctggccg ccaacatcc tgcagtggat caccttcgcc    300
ctgtctgccc tgtgcctgat gttctacggc taccagacct ggaagtccac ctgcggctgg    360
gaggaaatct acgtggccac catcgagatg atcaagttca tcatcgagta cttccacgag    420
ttcgacgagc ccgccaccct gtggctgtcc agcgaaacg gcgtggtgtg gatgagatac    480
ggcgagtggc tgctgacctg ccctgtgctg ctgatccacc tgagcaacct gaccggactg    540
aaggatgact acagcaagag aaccatggga ctgctggtgt ccgatgtggg atgcatcgtg    600
tggggagcca cctccgccat gtgcaccgga tggaccaaga tcctgttctt cctgatcagc    660
ctgagctacg gaatgtacac ctacttccac gccgccaagg tgtacattga ggcctttcac    720
accgtgccta aggaatctg cagagaactg gtcagagtga tggcctggac cttcttcgtg    780
gcctggggaa tgttccctgt gctgttcctg ctgggaaccg agggattcgg acacatcagc    840
ccttacggaa gcgccatcgg acacagcatc ctggatctga tcgccaagaa catgtgggga    900
gtgctgggaa actacctgag agtgaagatc cacgagcaca tcctgctgta cggcgacatc    960
agaaagaagc agaagatcac catcgccgga caggaaatgg aagtcgagac cctggtggcc   1020
gaggaagagg at                                                       1032

<210> SEQ ID NO 11

<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 11

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 12
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 12

Met Asp Tyr Gly Gly Ala Leu Ser Ala Val Gly Arg Glu Leu Leu Phe

```
               1               5                  10                 15
Val Thr Asn Pro Val Val Asn Gly Ser Val Leu Val Pro Glu Asp
               20                 25                 30

Gln Cys Tyr Cys Ala Gly Trp Ile Glu Ser Arg Gly Thr Asn Gly Ala
               35                 40                 45

Gln Thr Ala Ser Asn Val Leu Gln Trp Leu Ala Ala Gly Phe Ser Ile
               50                 55                 60

Leu Leu Leu Met Phe Tyr Ala Tyr Gln Thr Trp Lys Ser Thr Cys Gly
 65                70                 75                 80

Trp Glu Glu Ile Tyr Val Cys Ala Ile Glu Met Val Lys Val Ile Leu
                   85                 90                 95

Glu Phe Phe Phe Glu Phe Lys Asn Pro Ser Met Leu Tyr Leu Ala Thr
                  100                105                110

Gly His Arg Val Gln Trp Leu Arg Tyr Ala Glu Trp Leu Leu Thr Cys
                  115                120                125

Pro Val Ile Leu Ile Arg Leu Ser Asn Leu Thr Gly Leu Ser Asn Asp
                  130                135                140

Tyr Ser Arg Arg Thr Met Gly Leu Leu Val Ser Asp Ile Gly Thr Ile
145                150                155                160

Val Trp Gly Ala Thr Ser Ala Met Ala Thr Gly Tyr Val Lys Val Ile
                  165                170                175

Phe Phe Cys Leu Gly Leu Cys Tyr Gly Ala Asn Thr Phe Phe His Ala
                  180                185                190

Ala Lys Ala Tyr Ile Glu Gly Tyr His Thr Val Pro Lys Gly Arg Cys
                  195                200                205

Arg Gln Val Val Thr Gly Met Ala Trp Leu Phe Phe Val Ser Trp Gly
                  210                215                220

Met Phe Pro Ile Leu Phe Ile Leu Gly Pro Glu Gly Phe Gly Val Leu
225                230                235                240

Ser Val Tyr Gly Ser Thr Val Gly His Thr Ile Ile Asp Leu Met Ser
                  245                250                255

Lys Asn Cys Trp Gly Leu Leu Gly His Tyr Leu Arg Val Leu Ile His
                  260                265                270

Glu His Ile Leu Ile His Gly Asp Ile Arg Lys Thr Thr Lys Leu Asn
                  275                280                285

Ile Gly Gly Thr Glu Ile Glu Val Glu Thr Leu Val Glu Asp Glu Ala
                  290                295                300

Glu Ala Gly Ala Val Pro
305                310

<210> SEQ ID NO 13
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 13

Met Asp Tyr Gly Gly Ala Leu Ser Ala Val Gly Arg Glu Leu Leu Phe
 1               5                  10                 15

Val Thr Asn Pro Val Val Asn Gly Ser Val Leu Val Pro Glu Asp
               20                 25                 30

Gln Cys Tyr Cys Ala Gly Trp Ile Glu Ser Arg Gly Thr Asn Gly Ala
               35                 40                 45

Gln Thr Ala Ser Asn Val Leu Gln Trp Leu Ala Ala Gly Phe Ser Ile
```

```
Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro
305                 310

<210> SEQ ID NO 14
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 14

Met Asp Tyr Gly Gly Ala Leu Ser Ala Val Gly Arg Glu Leu Leu Phe
  1               5                  10                  15

Val Thr Asn Pro Val Val Val Asn Gly Ser Val Leu Val Pro Glu Asp
                 20                  25                  30

Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Gly Phe Ser Ile
         50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
```

```
            100                 105                 110
Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Thr Leu Val Glu Asp Glu Ala
    290                 295                 300

Glu Ala Gly Ala Val Pro
305                 310

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide

<400> SEQUENCE: 15

Lys Ser Arg Ile Thr Ser Glu Gly Glu Tyr Ile Pro Leu Asp Gln Ile
1               5                   10                  15

Asp Ile Asn Val
            20

<210> SEQ ID NO 16
<211> LENGTH: 344
<212> TYPE: PRT
<213> ORGANISM: Chlamydomonas reinhardtii

<400> SEQUENCE: 16

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65              70                  75                  80
```

-continued

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Arg Val Ile Leu Ile His Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
                260                 265                 270

Pro Glu Gly Phe Gly His Ile Asn Gln Phe Asn Ser Ala Ile Ala His
            275                 280                 285

Ala Ile Leu Asp Leu Ala Ser Lys Asn Ala Trp Ser Met Met Gly His
290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp
            340

<210> SEQ ID NO 17
<211> LENGTH: 300
<212> TYPE: PRT
<213> ORGANISM: Volvox carteri

<400> SEQUENCE: 17

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
                20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val

-continued

```
            100                 105                 110
Trp Met Arg Tyr Gly Glu Trp Leu Leu Thr Cys Pro Val Leu Leu Ile
        115                 120             125

His Leu Ser Asn Leu Thr Gly Leu Lys Asp Asp Tyr Ser Lys Arg Thr
        130             135             140

Met Gly Leu Leu Val Ser Asp Val Gly Cys Ile Val Trp Gly Ala Thr
145             150             155                 160

Ser Ala Met Cys Thr Gly Trp Thr Lys Ile Leu Phe Phe Leu Ile Ser
                165             170             175

Leu Ser Tyr Gly Met Tyr Thr Tyr Phe His Ala Ala Lys Val Tyr Ile
            180             185             190

Glu Ala Phe His Thr Val Pro Lys Gly Ile Cys Arg Glu Leu Val Arg
        195             200             205

Val Met Ala Trp Thr Phe Phe Val Ala Trp Gly Met Phe Pro Val Leu
        210             215             220

Phe Leu Leu Gly Thr Glu Gly Phe Gly His Ile Ser Pro Tyr Gly Ser
225             230             235             240

Ala Ile Gly His Ser Ile Leu Asp Leu Ile Ala Lys Asn Met Trp Gly
                245             250             255

Val Leu Gly Asn Tyr Leu Arg Val Lys Ile His Glu His Ile Leu Leu
            260             265             270

Tyr Gly Asp Ile Arg Lys Lys Gln Lys Ile Thr Ile Ala Gly Gln Glu
            275             280             285

Met Glu Val Glu Thr Leu Val Ala Glu Glu Asp
        290             295             300
```